(12) United States Patent
Timm et al.

(10) Patent No.: US 8,979,843 B2
(45) Date of Patent: Mar. 17, 2015

(54) ELECTROSURGICAL CUTTING AND SEALING INSTRUMENT

(75) Inventors: Richard W. Timm, Cincinnati, OH (US); Robert J. Laird, Morrow, OH (US); Omar J. Vakharia, Cincinnati, OH (US); Suzanne E. Thompson, West Chester, OH (US); Gavin M. Monson, Oxford, OH (US); John V. Hunt, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1051 days.

(21) Appl. No.: 12/842,476

(22) Filed: Jul. 23, 2010

(65) Prior Publication Data

US 2012/0022524 A1    Jan. 26, 2012

(51) Int. Cl.
| | |
|---|---|
| *A61B 18/12* | (2006.01) |
| *A61B 18/14* | (2006.01) |
| *A61B 17/29* | (2006.01) |
| *A61B 18/00* | (2006.01) |
| *A61B 19/00* | (2006.01) |

(52) U.S. Cl.
CPC ..... *A61B 18/1445* (2013.01); *A61B 2017/2912* (2013.01); *A61B 2018/00196* (2013.01); *A61B 2018/1455* (2013.01); *A61B 2019/2292* (2013.01)
USPC .............................................. 606/51; 606/52

(58) Field of Classification Search
CPC ................... A61B 2018/1452; A61B 18/1442; A61B 18/1445; A61B 2018/1455; A61B 17/115; A61B 2017/1125; A61B 17/1152; A61B 17/1155
USPC ...................................... 606/50–52, 205–209
See application file for complete search history.

(56) References Cited

U.S. PATENT DOCUMENTS

| | | | |
|---|---|---|---|
| 2,366,274 | A | 1/1945 | Luth et al. |
| 2,458,152 | A | 1/1949 | Eakins |
| 2,510,693 | A | 6/1950 | Green |
| 3,166,971 | A | 1/1965 | Stoecker |
| 3,580,841 | A | 5/1971 | Cadotte et al. |
| 3,703,651 | A | 11/1972 | Blowers |
| 3,777,760 | A | 12/1973 | Essner |
| 4,005,714 | A | 2/1977 | Hiltebrandt |
| 4,034,762 | A | 7/1977 | Cosens et al. |
| 4,058,126 | A | 11/1977 | Leveen |

(Continued)

FOREIGN PATENT DOCUMENTS

| | | |
|---|---|---|
| DE | 29623113 U1 | 10/1997 |
| DE | 20004812 U1 | 9/2000 |

(Continued)

OTHER PUBLICATIONS

International Search Report for PCT/US2011/044916, Oct. 25, 2011 (7 pages).

(Continued)

*Primary Examiner* — Jaymi Della

(57) ABSTRACT

A surgical instrument for supplying energy to tissue can comprise a jaw member comprising an electrode, wherein the electrode is configured to supply energy from a power source to captured tissue. The surgical instrument comprises a tissue-cutting element to transect the captured tissue. The rate of distal translation of the tissue-cutting element during the operational stroke may be regulated by a linear actuator, for example.

19 Claims, 32 Drawing Sheets

(56) References Cited

U.S. PATENT DOCUMENTS

| | | | |
|---|---|---|---|
| 4,220,154 A | 9/1980 | Semm | |
| 4,237,441 A | 12/1980 | van Konynenburg et al. | |
| 4,281,785 A | 8/1981 | Brooks | |
| 4,304,987 A | 12/1981 | van Konynenburg | |
| 4,535,773 A * | 8/1985 | Yoon | 606/185 |
| 4,545,926 A | 10/1985 | Fouts, Jr. et al. | |
| 4,550,870 A | 11/1985 | Krumme et al. | |
| 4,582,236 A | 4/1986 | Hirose | |
| 4,761,871 A | 8/1988 | O'Connor et al. | |
| 4,849,133 A | 7/1989 | Yoshida et al. | |
| 4,910,389 A | 3/1990 | Sherman et al. | |
| 5,104,025 A | 4/1992 | Main et al. | |
| 5,106,538 A | 4/1992 | Barma et al. | |
| 5,108,383 A | 4/1992 | White | |
| 5,190,541 A | 3/1993 | Abele et al. | |
| 5,205,459 A | 4/1993 | Brinkerhoff et al. | |
| 5,285,945 A | 2/1994 | Brinkerhoff et al. | |
| 5,309,927 A | 5/1994 | Welch | |
| 5,318,589 A | 6/1994 | Lichtman | |
| 5,339,723 A | 8/1994 | Huitema | |
| 5,361,583 A | 11/1994 | Huitema | |
| 5,387,207 A | 2/1995 | Dyer et al. | |
| 5,389,098 A | 2/1995 | Tsuruta et al. | |
| 5,395,312 A | 3/1995 | Desai | |
| 5,395,364 A | 3/1995 | Anderhub et al. | |
| 5,403,312 A | 4/1995 | Yates et al. | |
| 5,417,709 A | 5/1995 | Slater | |
| 5,428,504 A | 6/1995 | Bhatla | |
| 5,429,131 A | 7/1995 | Scheinman et al. | |
| 5,451,227 A | 9/1995 | Michaelson | |
| 5,496,317 A | 3/1996 | Goble et al. | |
| 5,504,650 A | 4/1996 | Katsui et al. | |
| 5,511,556 A | 4/1996 | DeSantis | |
| 5,520,704 A | 5/1996 | Castro et al. | |
| 5,522,839 A | 6/1996 | Pilling | |
| 5,558,671 A | 9/1996 | Yates | |
| 5,563,179 A | 10/1996 | Stone et al. | |
| 5,571,121 A | 11/1996 | Heifetz | |
| 5,599,350 A | 2/1997 | Schulze et al. | |
| 5,618,307 A | 4/1997 | Donlon et al. | |
| 5,624,452 A | 4/1997 | Yates | |
| 5,647,871 A | 7/1997 | Levine et al. | |
| 5,662,667 A | 9/1997 | Knodel | |
| 5,665,085 A | 9/1997 | Nardella | |
| 5,665,100 A | 9/1997 | Yoon | |
| 5,674,220 A | 10/1997 | Fox et al. | |
| 5,688,270 A | 11/1997 | Yates et al. | |
| 5,693,051 A | 12/1997 | Schulze et al. | |
| 5,709,680 A | 1/1998 | Yates et al. | |
| 5,716,366 A | 2/1998 | Yates | |
| 5,735,848 A | 4/1998 | Yates et al. | |
| 5,752,973 A | 5/1998 | Kieturakis | |
| 5,755,717 A | 5/1998 | Yates et al. | |
| 5,762,255 A | 6/1998 | Chrisman et al. | |
| 5,782,834 A | 7/1998 | Lucey et al. | |
| 5,797,941 A | 8/1998 | Schulze et al. | |
| 5,800,432 A | 9/1998 | Swanson | |
| 5,807,393 A | 9/1998 | Williamson, IV et al. | |
| 5,810,811 A | 9/1998 | Yates et al. | |
| 5,817,033 A | 10/1998 | DeSantis et al. | |
| 5,817,093 A | 10/1998 | Williamson, IV et al. | |
| 5,876,401 A | 3/1999 | Schulze et al. | |
| 5,880,668 A | 3/1999 | Hall | |
| 5,906,625 A | 5/1999 | Bito et al. | |
| 5,984,938 A | 11/1999 | Yoon | |
| 6,003,517 A | 12/1999 | Sheffield et al. | |
| 6,013,052 A | 1/2000 | Durman et al. | |
| 6,024,741 A | 2/2000 | Williamson, IV et al. | |
| 6,063,098 A | 5/2000 | Houser et al. | |
| 6,068,629 A | 5/2000 | Haissaguerre et al. | |
| 6,074,389 A | 6/2000 | Levine et al. | |
| 6,099,483 A | 8/2000 | Palmer et al. | |
| 6,099,550 A | 8/2000 | Yoon | |
| H1904 H | 10/2000 | Yates et al. | |
| 6,174,309 B1 | 1/2001 | Wrublewski et al. | |
| 6,206,876 B1 | 3/2001 | Levine et al. | |
| 6,292,700 B1 | 9/2001 | Morrison et al. | |
| 6,340,878 B1 | 1/2002 | Oglesbee | |
| H2037 H | 7/2002 | Yates et al. | |
| 6,443,968 B1 | 9/2002 | Holthaus et al. | |
| 6,458,128 B1 | 10/2002 | Schulze | |
| 6,464,702 B2 | 10/2002 | Schulze et al. | |
| 6,500,176 B1 | 12/2002 | Truckai et al. | |
| 6,503,248 B1 | 1/2003 | Levine | |
| 6,514,252 B2 | 2/2003 | Nezhat et al. | |
| 6,517,565 B1 | 2/2003 | Whitman et al. | |
| 6,533,784 B2 | 3/2003 | Truckai et al. | |
| 6,554,829 B2 | 4/2003 | Schulze et al. | |
| 6,558,376 B2 | 5/2003 | Bishop | |
| 6,572,639 B1 | 6/2003 | Ingle et al. | |
| 6,575,969 B1 | 6/2003 | Rittman, III et al. | |
| 6,589,200 B1 | 7/2003 | Schwemberger et al. | |
| 6,602,252 B2 | 8/2003 | Mollenauer | |
| 6,620,161 B2 | 9/2003 | Schulze et al. | |
| 6,623,482 B2 | 9/2003 | Pendekanti et al. | |
| 6,635,057 B2 | 10/2003 | Harano et al. | |
| 6,656,177 B2 | 12/2003 | Truckai et al. | |
| 6,656,198 B2 | 12/2003 | Tsonton et al. | |
| 6,673,248 B2 | 1/2004 | Chowdhury | |
| 6,679,882 B1 | 1/2004 | Kornerup | |
| 6,695,840 B2 | 2/2004 | Schulze | |
| 6,722,552 B2 | 4/2004 | Fenton, Jr. | |
| 6,770,072 B1 | 8/2004 | Truckai et al. | |
| 6,773,409 B2 | 8/2004 | Truckai et al. | |
| 6,773,435 B2 | 8/2004 | Schulze et al. | |
| 6,789,939 B2 | 9/2004 | Schrödinger et al. | |
| 6,800,085 B2 | 10/2004 | Selmon et al. | |
| 6,802,843 B2 | 10/2004 | Truckai et al. | |
| 6,811,842 B1 | 11/2004 | Ehrnsperger et al. | |
| 6,821,273 B2 | 11/2004 | Mollenauer | |
| 6,835,199 B2 | 12/2004 | McGuckin, Jr. et al. | |
| 6,840,938 B1 | 1/2005 | Morley et al. | |
| 6,860,880 B2 | 3/2005 | Treat et al. | |
| 6,905,497 B2 | 6/2005 | Truckai et al. | |
| 6,908,463 B2 | 6/2005 | Treat et al. | |
| 6,913,579 B2 | 7/2005 | Truckai et al. | |
| 6,926,716 B2 | 8/2005 | Baker et al. | |
| 6,929,622 B2 | 8/2005 | Chian | |
| 6,929,644 B2 | 8/2005 | Truckai et al. | |
| 6,953,461 B2 | 10/2005 | McClurken et al. | |
| 7,000,818 B2 | 2/2006 | Shelton, IV et al. | |
| 7,011,657 B2 | 3/2006 | Truckai et al. | |
| 7,041,102 B2 | 5/2006 | Truckai et al. | |
| 7,055,731 B2 | 6/2006 | Shelton, IV et al. | |
| 7,063,699 B2 | 6/2006 | Hess et al. | |
| 7,066,936 B2 | 6/2006 | Ryan | |
| 7,070,597 B2 | 7/2006 | Truckai et al. | |
| 7,083,619 B2 | 8/2006 | Truckai et al. | |
| 7,087,054 B2 | 8/2006 | Truckai et al. | |
| 7,094,235 B2 | 8/2006 | Francischelli et al. | |
| 7,101,371 B2 | 9/2006 | Dycus et al. | |
| 7,101,372 B2 | 9/2006 | Dycus et al. | |
| 7,112,201 B2 | 9/2006 | Truckai et al. | |
| 7,125,409 B2 | 10/2006 | Truckai et al. | |
| 7,131,970 B2 | 11/2006 | Moses et al. | |
| 7,137,980 B2 | 11/2006 | Buysse et al. | |
| 7,143,925 B2 | 12/2006 | Shelton, IV et al. | |
| 7,147,138 B2 | 12/2006 | Shelton, IV | |
| 7,156,846 B2 | 1/2007 | Dycus et al. | |
| 7,169,146 B2 | 1/2007 | Truckai et al. | |
| 7,169,156 B2 | 1/2007 | Hart | |
| 7,186,253 B2 | 3/2007 | Truckai et al. | |
| 7,189,233 B2 | 3/2007 | Truckai et al. | |
| 7,207,471 B2 | 4/2007 | Heinrich et al. | |
| 7,220,951 B2 | 5/2007 | Truckai et al. | |
| 7,225,964 B2 | 6/2007 | Mastri et al. | |
| 7,232,440 B2 | 6/2007 | Dumbauld et al. | |
| 7,235,073 B2 | 6/2007 | Levine et al. | |
| 7,241,294 B2 | 7/2007 | Reschke | |
| 7,252,667 B2 | 8/2007 | Moses et al. | |
| 7,267,685 B2 | 9/2007 | Butaric et al. | |
| 7,287,682 B1 | 10/2007 | Ezzat et al. | |
| 7,300,450 B2 | 11/2007 | Vleugels et al. | |
| 7,307,313 B2 | 12/2007 | Ohyanagi et al. | |

(56) References Cited

U.S. PATENT DOCUMENTS

| | | |
|---|---|---|
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckal et al. |
| 7,371,227 B2 | 5/2008 | Zeiner |
| 7,381,209 B2 | 6/2008 | Truckai et al. |
| 7,396,356 B2 | 7/2008 | Mollenauer |
| 7,404,508 B2 | 7/2008 | Smith et al. |
| 7,407,077 B2 | 8/2008 | Ortiz et al. |
| 7,422,139 B2 | 9/2008 | Shelton, IV et al. |
| 7,435,582 B2 | 10/2008 | Zimmermann et al. |
| 7,445,621 B2 | 11/2008 | Dumbauld et al. |
| 7,464,846 B2 | 12/2008 | Shelton, IV et al. |
| 7,488,319 B2 | 2/2009 | Yates |
| 7,491,201 B2 | 2/2009 | Shields et al. |
| 7,510,107 B2 | 3/2009 | Timm et al. |
| 7,513,025 B2 | 4/2009 | Fischer |
| 7,517,349 B2 | 4/2009 | Truckai et al. |
| 7,540,872 B2 | 6/2009 | Schechter et al. |
| 7,550,216 B2 | 6/2009 | Ofer et al. |
| 7,559,452 B2 | 7/2009 | Wales et al. |
| 7,582,086 B2 | 9/2009 | Privitera et al. |
| 7,588,176 B2 | 9/2009 | Timm et al. |
| 7,597,693 B2 | 10/2009 | Garrison |
| 7,604,150 B2 | 10/2009 | Boudreaux |
| 7,628,791 B2 | 12/2009 | Garrison et al. |
| 7,628,792 B2 | 12/2009 | Guerra |
| 7,632,269 B2 | 12/2009 | Truckai et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,703,459 B2 | 4/2010 | Saadat et al. |
| 7,708,751 B2 | 5/2010 | Hughes et al. |
| 7,722,607 B2 | 5/2010 | Dumbauld et al. |
| 7,753,904 B2 | 7/2010 | Shelton, IV et al. |
| 7,762,445 B2 | 7/2010 | Heinrich et al. |
| 7,766,910 B2 | 8/2010 | Hixson et al. |
| 7,776,037 B2 | 8/2010 | Odom |
| 7,780,663 B2 | 8/2010 | Yates et al. |
| 7,784,663 B2 | 8/2010 | Shelton, IV |
| 7,803,156 B2 | 9/2010 | Eder et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,832,408 B2 | 11/2010 | Shelton, IV et al. |
| 7,832,612 B2 | 11/2010 | Baxter, III et al. |
| 7,879,035 B2 | 2/2011 | Garrison et al. |
| 7,879,070 B2 | 2/2011 | Ortiz et al. |
| 7,931,649 B2 | 4/2011 | Couture et al. |
| 7,935,114 B2 | 5/2011 | Takashino et al. |
| 7,955,331 B2 | 6/2011 | Truckai et al. |
| 7,963,963 B2 | 6/2011 | Francischelli et al. |
| 7,967,602 B2 | 6/2011 | Lindquist |
| 7,981,113 B2 | 7/2011 | Truckai et al. |
| 8,020,743 B2 | 9/2011 | Shelton, IV |
| 8,070,036 B1 | 12/2011 | Knodel et al. |
| 8,128,624 B2 | 3/2012 | Couture et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,221,415 B2 | 7/2012 | Francischelli |
| 8,246,618 B2 | 8/2012 | Bucciaglia et al. |
| 8,277,446 B2 | 10/2012 | Heard |
| 8,282,669 B2 | 10/2012 | Gerber et al. |
| 8,292,886 B2 | 10/2012 | Kerr et al. |
| 8,298,232 B2 | 10/2012 | Unger |
| 8,323,310 B2 | 12/2012 | Kingsley |
| 8,414,577 B2 | 4/2013 | Boudreaux et al. |
| 8,453,906 B2 | 6/2013 | Huang et al. |
| 8,460,292 B2 | 6/2013 | Truckai et al. |
| 8,613,383 B2 | 12/2013 | Beckman et al. |
| 8,628,529 B2 | 1/2014 | Aldridge et al. |
| 2002/0115997 A1* | 8/2002 | Truckai et al. ............ 606/51 |
| 2002/0165541 A1 | 11/2002 | Whitman |
| 2003/0014053 A1 | 1/2003 | Nguyen et al. |
| 2003/0105474 A1 | 6/2003 | Bonutti |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0216722 A1 | 11/2003 | Swanson |
| 2004/0019350 A1 | 1/2004 | O'Brien et al. |
| 2004/0138621 A1 | 7/2004 | Jahns et al. |
| 2004/0193150 A1 | 9/2004 | Sharkey et al. |
| 2004/0232196 A1 | 11/2004 | Shelton, IV et al. |
| 2004/0260273 A1 | 12/2004 | Wan |
| 2005/0033278 A1 | 2/2005 | McClurken et al. |
| 2005/0085809 A1 | 4/2005 | Mucko et al. |
| 2005/0090817 A1 | 4/2005 | Phan |
| 2005/0165429 A1 | 7/2005 | Douglas et al. |
| 2005/0171522 A1 | 8/2005 | Christopherson |
| 2005/0203507 A1 | 9/2005 | Truckai et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0293654 A1* | 12/2006 | Morrison et al. ............ 606/41 |
| 2006/0293656 A1 | 12/2006 | Shadduck et al. |
| 2007/0027469 A1 | 2/2007 | Smith et al. |
| 2007/0073185 A1 | 3/2007 | Nakao |
| 2007/0073341 A1 | 3/2007 | Smith et al. |
| 2007/0106158 A1 | 5/2007 | Madan et al. |
| 2007/0146113 A1 | 6/2007 | Truckai et al. |
| 2007/0173813 A1 | 7/2007 | Odom |
| 2007/0175956 A1* | 8/2007 | Swayze et al. ............ 227/178.1 |
| 2007/0191713 A1 | 8/2007 | Eichmann et al. |
| 2007/0208312 A1 | 9/2007 | Norton et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0236213 A1 | 10/2007 | Paden et al. |
| 2007/0239025 A1 | 10/2007 | Wiener et al. |
| 2007/0260242 A1 | 11/2007 | Dycus et al. |
| 2007/0265613 A1 | 11/2007 | Edelstein et al. |
| 2008/0071269 A1 | 3/2008 | Hilario et al. |
| 2008/0147062 A1 | 6/2008 | Truckai et al. |
| 2008/0167522 A1 | 7/2008 | Giordano et al. |
| 2008/0188851 A1 | 8/2008 | Truckai et al. |
| 2008/0221565 A1 | 9/2008 | Eder et al. |
| 2008/0262491 A1 | 10/2008 | Swoyer et al. |
| 2008/0294158 A1 | 11/2008 | Pappone et al. |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0099582 A1 | 4/2009 | Isaacs et al. |
| 2009/0125026 A1* | 5/2009 | Rioux et al. ............ 606/45 |
| 2009/0125027 A1 | 5/2009 | Fischer |
| 2009/0138003 A1 | 5/2009 | Deville et al. |
| 2009/0138006 A1 | 5/2009 | Bales et al. |
| 2009/0171354 A1* | 7/2009 | Deville et al. ............ 606/51 |
| 2009/0206140 A1 | 8/2009 | Scheib et al. |
| 2009/0209979 A1 | 8/2009 | Yates et al. |
| 2009/0248002 A1 | 10/2009 | Takashino et al. |
| 2009/0320268 A1 | 12/2009 | Cunningham et al. |
| 2009/0326530 A1 | 12/2009 | Orban, III et al. |
| 2010/0010299 A1 | 1/2010 | Bakos et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0036405 A1 | 2/2010 | Giordano et al. |
| 2010/0076433 A1 | 3/2010 | Taylor et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |

(56) References Cited

U.S. PATENT DOCUMENTS

| | | | |
|---|---|---|---|
| 2010/0094323 A1 | 4/2010 | Isaacs et al. | |
| 2010/0237132 A1 | 9/2010 | Measamer et al. | |
| 2010/0256635 A1* | 10/2010 | McKenna et al. | 606/45 |
| 2010/0264194 A1 | 10/2010 | Huang et al. | |
| 2010/0274278 A1 | 10/2010 | Fleenor et al. | |
| 2011/0087208 A1 | 4/2011 | Boudreaux et al. | |
| 2011/0087209 A1 | 4/2011 | Boudreaux et al. | |
| 2011/0087218 A1 | 4/2011 | Boudreaux et al. | |
| 2011/0087219 A1 | 4/2011 | Boudreaux et al. | |
| 2011/0087220 A1 | 4/2011 | Felder et al. | |
| 2011/0155781 A1 | 6/2011 | Swensgard et al. | |
| 2011/0224668 A1 | 9/2011 | Johnson et al. | |
| 2011/0238065 A1 | 9/2011 | Hunt et al. | |
| 2011/0251608 A1 | 10/2011 | Timm et al. | |
| 2011/0251609 A1 | 10/2011 | Johnson et al. | |
| 2011/0251612 A1 | 10/2011 | Faller et al. | |
| 2011/0251613 A1 | 10/2011 | Guerra et al. | |
| 2011/0264093 A1 | 10/2011 | Schall | |
| 2011/0276057 A1 | 11/2011 | Conlon et al. | |
| 2011/0282339 A1 | 11/2011 | Weizman et al. | |
| 2011/0301605 A1 | 12/2011 | Horner | |
| 2011/0306963 A1 | 12/2011 | Dietz et al. | |
| 2011/0306964 A1 | 12/2011 | Stulen et al. | |
| 2011/0306965 A1 | 12/2011 | Norvell et al. | |
| 2011/0306966 A1 | 12/2011 | Dietz et al. | |
| 2011/0306967 A1 | 12/2011 | Payne et al. | |
| 2011/0306968 A1 | 12/2011 | Beckman et al. | |
| 2011/0306972 A1 | 12/2011 | Widenhouse et al. | |
| 2011/0306973 A1 | 12/2011 | Cummings et al. | |
| 2012/0010615 A1 | 1/2012 | Cummings et al. | |
| 2012/0010616 A1 | 1/2012 | Huang et al. | |
| 2012/0016413 A1 | 1/2012 | Timm et al. | |
| 2012/0022519 A1 | 1/2012 | Huang et al. | |
| 2012/0022525 A1 | 1/2012 | Dietz et al. | |
| 2012/0022526 A1 | 1/2012 | Aldridge et al. | |
| 2012/0022527 A1 | 1/2012 | Woodruff et al. | |
| 2012/0022528 A1 | 1/2012 | White et al. | |
| 2012/0022529 A1 | 1/2012 | Shelton, Iv et al. | |
| 2012/0022530 A1 | 1/2012 | Woodruff et al. | |
| 2012/0083783 A1 | 4/2012 | Davison et al. | |
| 2012/0116379 A1 | 5/2012 | Yates et al. | |
| 2012/0116391 A1 | 5/2012 | Houser et al. | |
| 2012/0136353 A1 | 5/2012 | Romero | |
| 2012/0150176 A1 | 6/2012 | Weizman | |
| 2013/0023875 A1 | 1/2013 | Harris et al. | |
| 2013/0030433 A1 | 1/2013 | Heard | |
| 2013/0053831 A1 | 2/2013 | Johnson et al. | |
| 2013/0079762 A1 | 3/2013 | Twomey et al. | |

FOREIGN PATENT DOCUMENTS

| | | | |
|---|---|---|---|
| DE | 10201569 A1 | 7/2003 | |
| EP | 0340803 B1 | 8/1993 | |
| EP | 0630612 A1 | 12/1994 | |
| EP | 0705571 A1 | 4/1996 | |
| EP | 0640317 B1 | 9/1999 | |
| EP | 1749479 A1 | 2/2007 | |
| EP | 1767157 A1 | 3/2007 | |
| EP | 1878399 A1 | 1/2008 | |
| EP | 1915953 A1 | 4/2008 | |
| EP | 1532933 B1 | 5/2008 | |
| EP | 1707143 B1 | 6/2008 | |
| EP | 1943957 A2 | 7/2008 | |
| EP | 1849424 B1 | 4/2009 | |
| EP | 2042117 A1 | 4/2009 | |
| EP | 2060238 A1 | 5/2009 | |
| EP | 1810625 B1 | 8/2009 | |
| EP | 2090238 A1 | 8/2009 | |
| EP | 2090256 A2 * | 8/2009 | A61B 17/072 |
| EP | 2092905 A1 | 8/2009 | |
| EP | 2105104 A2 | 9/2009 | |
| EP | 1747761 B1 | 10/2009 | |
| EP | 1769766 B1 | 2/2010 | |
| EP | 2151204 A1 | 2/2010 | |
| EP | 2153791 A1 | 2/2010 | |
| EP | 2243439 A1 | 10/2010 | |
| EP | 1728475 B1 | 8/2011 | |
| EP | 2353518 A1 | 8/2011 | |
| WO | WO 93/22973 A1 | 11/1993 | |
| WO | WO 96/35382 A1 | 11/1996 | |
| WO | WO 98/00069 A1 | 1/1998 | |
| WO | WO 98/40020 A1 | 9/1998 | |
| WO | WO 98/57588 A1 | 12/1998 | |
| WO | WO 99/23960 A1 | 5/1999 | |
| WO | WO 99/40861 A1 | 8/1999 | |
| WO | WO 00/25691 A1 | 5/2000 | |
| WO | WO 01/28444 A1 | 4/2001 | |
| WO | WO 03/013374 A1 | 2/2003 | |
| WO | WO 03/020339 A2 | 3/2003 | |
| WO | WO 03/028541 A2 | 4/2003 | |
| WO | WO 03/030708 A2 | 4/2003 | |
| WO | WO 03/068046 A2 | 8/2003 | |
| WO | WO 2004/011037 A2 | 2/2004 | |
| WO | WO 2005/052959 A2 | 6/2005 | |
| WO | WO 2006/021269 A1 | 3/2006 | |
| WO | WO 2006/036706 A1 | 4/2006 | |
| WO | WO 2006/055166 A2 | 5/2006 | |
| WO | WO 2008/020964 A2 | 2/2008 | |
| WO | WO 2008/045348 A2 | 4/2008 | |
| WO | WO 2008/099529 A1 | 8/2008 | |
| WO | WO 2008/101356 A1 | 8/2008 | |
| WO | WO 2009/022614 A1 | 2/2009 | |
| WO | WO 2009/036818 A1 | 3/2009 | |
| WO | WO 2009/039179 A1 | 3/2009 | |
| WO | WO 2009/059741 A1 | 5/2009 | |
| WO | WO 2009/082477 A2 | 7/2009 | |
| WO | WO 2009/149234 A1 | 12/2009 | |
| WO | WO 2010/017266 A1 | 2/2010 | |
| WO | WO 2010/104755 A1 | 9/2010 | |
| WO | WO 2011/089717 A1 | 7/2011 | |
| WO | WO 03/001986 A2 | 1/2013 | |

OTHER PUBLICATIONS

U.S. Appl. No. 13/221,410, filed Aug. 30, 2011.
U.S. Appl. No. 13/189,169, filed Jul. 22, 2011.
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Hörmann et al., "Reversible and irreversible denaturation of collagen fibers." Biochemistry, 10, pp. 932-937 (1971).
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-induced changes in the mechanics of a collagenous tissue: pseudoelastic behavior at 37° C," Journal of Biomechanics, 31, pp. 211-216 (1998).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Hayashi et al., "The Effect of Thermal Heating on the Length and Histologic Properties of the Glenohumeral Joint Capsule," American

(56) References Cited

OTHER PUBLICATIONS

Journal of Sports Medicine, vol. 25, Issue 1, 11 pages (Jan. 1997), URL: http://www.mdconsult.com/das/article/body/156183648-2/jorg=journal&source=MI&sp=1..., accessed Aug. 25, 2009.

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

Wall et al., "Thermal modification of collagen," J Shoulder Elbow Surg, No. 8, pp. 339-344 (Jul./Aug. 1999).

Wells et al., "Altered Mechanical Behavior of Epicardium Under Isothermal Biaxial Loading," Transactions of the ASME, Journal of Biomedical Engineering, vol. 126, pp. 492-497 (Aug. 2004).

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Humphrey, J.D., "Continuum Thermomechanics and the Clinical Treatment of Disease and Injury," Appl. Mech. Rev., vol. 56, No. 2 pp. 231-260 (Mar. 2003).

Kurt Gieck & Reiner Gieck, *Engineering Formulas* § Z.7 (7th ed. 1997).

National Semiconductors Temperature Sensor Handbook—http://www.national.com/appinfo/tempsensors/files/temphb.pdf; accessed online: Apr. 1, 2011.

U.S. Appl. No. 12/576,756, filed Oct. 9, 2009.
U.S. Appl. No. 12/576,776, filed Oct. 9, 2009.
U.S. Appl. No. 12/576,789, filed Oct. 9, 2009.
U.S. Appl. No. 12/576,808, filed Oct. 9, 2009.
U.S. Appl. No. 12/576,831, filed Oct. 9, 2009.
U.S. Appl. No. 12/836,366, filed Jul. 14, 2010.
U.S. Appl. No. 12/836,383, filed Jul. 14, 2010.
U.S. Appl. No. 12/836,396, filed Jul. 14, 2010.
U.S. Appl. No. 12/842,464, filed Jul. 23, 2010.
U.S. Appl. No. 12/842,507, filed Jul. 23, 2010.
U.S. Appl. No. 12/842,518, filed Jul. 23, 2010.
U.S. Appl. No. 12/842,538, filed Jul. 23, 2010.
U.S. Appl. No. 12/842,565, filed Jul. 23, 2010.
U.S. Appl. No. 12/758,253, filed Apr. 12, 2010.
U.S. Appl. No. 12/758,268, filed Apr. 12, 2010.
U.S. Appl. No. 12/758,284, filed Apr. 12, 2010.
U.S. Appl. No. 12/758,298, filed Apr. 12, 2010.
U.S. Appl. No. 12/765,175, filed Apr. 22, 2010.
U.S. Appl. No. 12/911,943, filed Oct. 26, 2010.
U.S. Appl. No. 12/841,480, filed Jul. 22, 2010.
U.S. Appl. No. 12/963,001, filed Dec. 8, 2010.
U.S. Appl. No. 12/732,992, filed Mar. 26, 2010.
U.S. Appl. No. 12/797,207, filed Jun. 9, 2010.
U.S. Appl. No. 12/797,252, filed Jun. 9, 2010.
U.S. Appl. No. 12/797,288, filed Jun. 9, 2010.
U.S. Appl. No. 12/797,305, filed Jun. 9, 2010.
U.S. Appl. No. 12/841,370, filed Jul. 22, 2010.
U.S. Appl. No. 12/797,844, filed Jun. 10, 2010.
U.S. Appl. No. 12/797,853, filed Jun. 10, 2010.
U.S. Appl. No. 12/797,861, filed Jun. 10, 2010.
U.S. Appl. No. 12/797,866, filed Jun. 10, 2010.
U.S. Appl. No. 12/832,345, filed Jul. 8, 2010.
U.S. Appl. No. 12/832,361, filed Jul. 8, 2010.
U.S. Appl. No. 12/781,243, filed May 17, 2010.
U.S. Appl. No. 12/775,724, filed May 7, 2010.
U.S. Appl. No. 12/622,113, filed Nov. 19, 2009.
U.S. Appl. No. 12/635,415, filed Dec. 10, 2009.
U.S. Appl. No. 12/647,134, filed Dec. 24, 2009.
Written Opinion for PCT/US2011/044916, Oct. 25, 2011 (8 pages).
Wright, et al., "Time-Temperature Equivalence of Heat-Induced Changes in Cells and Proteins," Feb. 1998. ASME Journal of Biomechanical Engineering, vol. 120, pp. 22-26.
U.S. Appl. No. 14/171,035, filed Feb. 3, 2014.
U.S. Appl. No. 14/158,248, filed Jan. 17, 2014.

\* cited by examiner

ELECTROSURGICAL CUTTING AND SEALING INSTRUMENT

BACKGROUND

The present invention relates to medical devices and methods. More particularly, the present invention relates to electrosurgical instruments and methods for sealing and transecting tissue.

In various circumstances, a surgical instrument can be configured to apply energy to tissue in order to treat and/or destroy the tissue. In certain circumstances, a surgical instrument can comprise one or more electrodes which can be positioned against and/or positioned relative to the tissue such that electrical current can flow from one electrode, through the tissue, and to the other electrode. The surgical instrument can comprise an electrical input, a supply conductor electrically coupled with the electrodes, and/or a return conductor which can be configured to allow current to flow from the electrical input, through the supply conductor, through the electrodes and the tissue, and then through the return conductor to an electrical output, for example. In various circumstances, heat can be generated by the current flowing through the tissue, wherein the heat can cause one or more hemostatic seals to form within the tissue and/or between tissues. Such embodiments may be particularly useful for sealing blood vessels, for example. The surgical instrument can also comprise a cutting element that can be moved relative to the tissue and the electrodes in order to transect the tissue.

By way of example, energy applied by a surgical instrument may be in the form of radio frequency ("RF") energy. RF energy is a form of electrical energy that may be in the frequency range of 300 kilohertz (kHz) to 1 megahertz (MHz). In application, RF surgical instruments transmit low frequency radio waves through electrodes, which cause ionic agitation, or friction, increasing the temperature of the tissue. Since a sharp boundary is created between the affected tissue and that surrounding it, surgeons can operate with a high level of precision and control, without much sacrifice to the adjacent normal tissue. The low operating temperatures of RF energy enables surgeons to remove, shrink or sculpt soft tissue while simultaneously sealing blood vessels. RF energy works particularly well on connective tissue, which is primarily comprised of collagen and shrinks when contacted by heat.

In various open, endoscopic, and/or laparoscopic surgeries, for example, it may be necessary to coagulate, seal, and/or fuse tissue. One means of sealing tissue relies upon the application of electrical energy to tissue captured within an end effector of a surgical instrument in order to cause thermal effects within the tissue. Various mono-polar and bi-polar radio frequency (RF) surgical instruments and surgical techniques have been developed for such purposes. In general, the delivery of RF energy to the captured tissue elevates the temperature of the tissue and, as a result, the energy can at least partially denature proteins within the tissue. Such proteins, such as collagen, for example, may be denatured into a proteinaceous amalgam that intermixes and fuses, or "welds", together as the proteins renature. As the treated region heals over time, this biological "weld" may be reabsorbed by the body's wound healing process.

In certain arrangements of a bi-polar radio frequency (RF) surgical instrument, the surgical instrument can comprise opposing first and second jaws, wherein the face of each jaw can comprise an electrode. In use, the tissue can be captured between the jaw faces such that electrical current can flow between the electrodes in the opposing jaws and through the tissue positioned therebetween. Such instruments may have to seal or "weld" many types of tissues, such as anatomic structures having walls with irregular or thick fibrous content, bundles of disparate anatomic structures, substantially thick anatomic structures, and/or tissues with thick fascia layers such as large diameter blood vessels, for example. With particular regard to sealing large diameter blood vessels, for example, such applications may require a high strength tissue weld immediately post-treatment.

The foregoing discussion is intended only to illustrate various aspects of the related art in the field of the invention at the time, and should not be taken as a disavowal of claim scope.

SUMMARY

In one embodiment, an electrosurgical instrument may comprise a handle, an elongate shaft extending distally from the handle, where the elongate shaft defines a longitudinal axis, and a trigger coupled to the elongate shaft. The electrosurgical instrument may also comprise an end effector coupled to the distal end of the elongate shaft that comprises a first jaw member and a second jaw member. The first jaw member may be movable relative to the second jaw member between an open and a closed position. The electrosurgical instrument may also comprise an axially movable member configured to open and close the jaws and a tissue-cutting element positioned at a distal end of the axially movable member configured to translate with respect to the first jaw and the second jaw, and an electrode. The electrosurgical instrument may also comprise a spring operably coupled to the trigger, the spring to release energy and distally translate the axially movable member.

In another embodiment, an electrosurgical instrument may comprise a handle, an elongate shaft extending distally from the handle, where the elongate shaft defines a longitudinal axis, and a trigger coupled to the elongate shaft. The electrosurgical instrument may further comprise an internal shaft, where the internal shaft defines a longitudinal axis that is substantially perpendicular to the longitudinal axis of the elongate shaft, and an end effector coupled to the distal end of the elongate shaft. The end effector may comprise a first jaw member and a second jaw member, where the first jaw member is movable relative to the second jaw member between an open and a closed position, an electrode, and a tissue-cutting element configured to translate with respect to the first jaw and the second jaw. The electrosurgical instrument may further comprise an axially moveable member configured to open and close the jaws. The tissue-cutting element may be positioned at a distal end of the axially movable member. The electrosurgical instrument may further comprise a spring operably connected to the trigger to regulate the distal translation the moveable cutting member.

In yet another embodiment, an electrosurgical instrument may comprise a handle, an elongate shaft extending distally from the handle, and an end effector coupled to the distal end of the elongate shaft. The end effector may comprise a first jaw member and a second jaw member, where the first jaw member is movable relative to the second jaw member between an open and a closed position. The end effector may also comprise a tissue-cutting element configured to translate with respect to the first jaw and the second jaw and an electrode. The electrosurgical instrument may further comprise an axially moveable member configured to open and close the jaws with the tissue-cutting element be positioned at a distal end of the axially movable member and a trigger coupled to the moveable cutting member. The electrosurgical instrument may further comprise an advance biasing member operably connected to the trigger and the moveable cutting member, and a return biasing member operably connected to the moveable cutting member and the handle.

In one embodiment, an electrosurgical instrument may comprise a handle, an elongate shaft extending distally from the handle, and an end effector coupled to the distal end of the elongate shaft. The end effector may comprise a first jaw member and a second jaw member, where the first jaw member is movable relative to the second jaw member between an open and a closed position. The end effector may also comprise a tissue-cutting element configured to translate with respect to the first jaw and the second jaw and an electrode. The electrosurgical instrument may further comprise an axially moveable cutting member configured to open and close the jaws and a trigger coupled to the axially moveable cutting member. The tissue-cutting element may be positioned at a distal end of the axially moveable member. The electrosurgical instrument may further comprise a linear actuator coupled to the axially moveable cutting member.

In another embodiment, an electrosurgical instrument may comprise a handle, an elongate shaft extending distally from the handle, and an end effector coupled to the distal end of the elongate shaft. The end effector may comprise a first jaw member and a second jaw member, where the first jaw member is movable relative to the second jaw member between an open and a closed position. The end effector may also comprise a tissue-cutting element configured to translate with respect to the first jaw and the second jaw and an electrode. The electrosurgical instrument may further comprise an axially moveable cutting member configured to open and close the jaws, where the moveable cutting member comprises a distal stop and a proximate stop, and a trigger coupled to the axially moveable cutting member movable between a first position, a second position, and a third position. The tissue-cutting element may be positioned at a distal end of the axially movable member. The electrosurgical instrument may further comprise a linear actuator coupled to a nut, where the nut is coupled to the axially moveable cutting member intermediate the distal stop and the proximate stop.

In yet another embodiment, an electrosurgical instrument may comprise a handle, an elongate shaft extending distally from the handle, and an end effector coupled to the distal end of the elongate shaft. The end effector may comprise a first jaw member and a second jaw member, where the first jaw member is movable relative to the second jaw member between an open and a closed position. The end effector may also comprise a tissue-cutting element configured to translate with respect to the first jaw and the second jaw and an electrode. The electrosurgical instrument may further comprise an axially moveable cutting member configured to open and close the jaws and a trigger coupled to the axially moveable cutting member, where the trigger is movable between a first position and a second position. The tissue-cutting element may be positioned at a distal end of the axially movable member. The electrosurgical instrument may further comprise a linear actuator coupled to the axially moveable cutting member and a load cell coupled to the axially moveable cutting member, where the load cell is configured to output a load signal, and where the linear actuator distally drives the axially moveable cutting member at a variable speed, where the variable speed is at least partially based on the load signal.

In one embodiment, an electrosurgical instrument may comprise a handle, an elongate shaft extending distally from the handle, a trigger moveable between a first position and a second position, and an end effector coupled to the distal end of the elongate shaft. The end effector may comprise a first jaw member and a second jaw member, where the first jaw member is movable relative to the second jaw member between an open and a closed position. The end effector may also comprise a tissue-cutting element configured to translate with respect to the first jaw and the second jaw, and an electrode. The electrosurgical instrument may further comprise an axially moveable cutting member configured to open and close the jaws, and a damper coupled to the trigger and the axially moveable cutting member. The tissue-cutting element may be positioned at a distal end of the axially movable member.

In another embodiment, an electrosurgical instrument may comprise a handle, an elongate shaft extending distally from the handle, and an end effector coupled to the distal end of the elongate shaft. The end effector may comprise a first jaw member and a second jaw member, where the first jaw member is movable relative to the second jaw member between an open and a closed position. The end effector may also comprise a tissue-cutting element configured to translate with respect to the first jaw and the second jaw and an electrode. The electrosurgical instrument may further comprise an axially moveable cutting member configured to open and close the jaws and a trigger moveable between a first position and a second position, where the trigger is coupled to the axially moveable cutting member. The tissue-cutting element may be positioned at a distal end of the axially movable member. The electrosurgical instrument may further comprise a damper positioned in the handle, where the damper is positioned to engage the trigger and oppose movement of the trigger from the first position to the second position.

In yet another embodiment, an electrosurgical instrument may a handle, an elongate shaft extending distally from the handle, and an end effector coupled to the distal end of the elongate shaft. The end effector may comprise a first jaw member, a second jaw member, where the first jaw member is movable relative to the second jaw member between an open and a closed position. The end effector may also comprise a tissue-cutting element configured to translate with respect to the first jaw and the second jaw, and an electrode. The electrosurgical instrument may further comprise an axially moveable cutting member configured to open and close the jaws, a trigger moveable between a first position and a second position, and a damper, where the damper comprises a barrel and a plunger, where the plunger is coupled to the axially moveable cutting member and the trigger. The tissue-cutting element may be positioned at a distal end of the axially movable member.

In one embodiment, an electrosurgical instrument may comprise a handle, an elongate shaft extending distally from the handle, a trigger moveable between a first position and a second position, an electromagnetic brake, and an end effector coupled to the distal end of the elongate shaft. The end effector may comprise a first jaw member, a second jaw member, where the first jaw member is movable relative to the second jaw member between an open and a closed position, and a tissue-cutting element configured to translate with respect to the first jaw and the second jaw. The end effector may also comprise an axially moveable cutting member configured to open and close the jaws, and an electrode. The tissue-cutting element may be positioned at a distal end of the axially movable member.

In another embodiment, an electrosurgical instrument may comprise a handle, an elongate shaft extending distally from the handle, a trigger moveable between a first position and a second position, and an electrically activated brake comprising an engaging portion. The engaging portion may be configured to move from a non-engaged position to an engaged position. The electrosurgical instrument may further comprise a controller and an end effector coupled to the distal end of the elongate shaft. The end effector may comprise a first jaw member, a second jaw member, where the first jaw member is movable relative to the second jaw member between an open and a closed position, a tissue-cutting element configured to translate with respect to the first jaw and the second jaw, and a sensor in electrical communication with the controller. The electrosurgical instrument may further comprise an axially moveable cutting member configured to open and close the jaws. The tissue-cutting element may be positioned at a distal end of the axially movable member.

In yet another embodiment, an electrosurgical instrument may comprise a handle, an elongate shaft extending distally from the handle, a trigger comprising a rotor moveable between a first position and a second position, and an electromagnetic brake configured to selectively engage the rotor. The electrosurgical instrument may further comprise an end effector coupled to the distal end of the elongate shaft. The end effector may comprise a first jaw member and a second jaw member, where the first jaw member is movable relative to the second jaw member between an open and a closed position. The end effector may also comprise a tissue-cutting element configured to translate with respect to the first jaw and the second jaw, and an electrode. The electrosurgical instrument may further comprise an axially moveable cutting member configured to open and close the jaws. The tissue-cutting element may be positioned at a distal end of the axially movable member.

In one embodiment, an electrosurgical instrument may comprise a handle, an elongate shaft extending distally from the handle, a trigger, and an end effector coupled to the distal end of the elongate shaft. The end effector may comprise a first jaw member and a second jaw member, where the first jaw member is movable relative to the second jaw member between an open and a closed position. The end effector may also comprise a tissue-cutting element configured to translate with respect to the first jaw and the second jaw, and an electrode. The electrosurgical instrument may further comprise an axially moveable cutting member configured to open and close the jaws, an electromagnet positioned proximate to the trigger, and an electromagnet engaging surface positioned proximate to the trigger. The tissue-cutting element may be positioned at a distal end of the axially movable member.

In another embodiment, an electrosurgical instrument may comprise a handle, an elongate shaft extending distally from the handle, a trigger movable between a plurality of positions, and an end effector coupled to the distal end of the elongate shaft. The end effector may comprise a first jaw member and a second jaw member, where the first jaw member is movable relative to the second jaw member between an open and a closed position. The end effector may also comprise a tissue-cutting element configured to translate with respect to the first jaw and the second jaw, and an electrode. The electrosurgical instrument may further comprise an axially moveable cutting member configured to open and close the jaws and a plurality of electromagnetic gates. The tissue-cutting element may be positioned at a distal end of the axially movable member.

In yet another embodiment, an electrosurgical instrument may comprise a handle, an elongate shaft extending distally from the handle, a trigger movable between a plurality of positions during a trigger stroke, and a first electromagnetic gate and a second electromagnetic gate. The first electromagnetic gate and a second electromagnetic gate may each be positioned to sequentially pass proximate to an electromagnet engaging surface during the trigger stroke. The electrosurgical instrument may further comprise an end effector coupled to the distal end of the elongate shaft that comprises a first jaw member and a second jaw member, where the first jaw member is movable relative to the second jaw member between an open and a closed position. The end effector may also comprise a tissue-cutting element configured to translate with respect to the first jaw and the second jaw and an electrode. The electrosurgical instrument may further comprise an axially moveable cutting member configured to close the jaws during the trigger stroke. The tissue-cutting element may be positioned at a distal end of the axially movable member.

In one embodiment, an electrosurgical instrument may comprise a handle with an indicator configured to provide a serial series of feedback signals during an operational stroke and an elongate shaft extending distally from the handle. The electrosurgical instrument may further comprise an end effector coupled to the distal end of the elongate shaft. The end effector may comprise a first jaw member and a second jaw member, where the first jaw member is movable relative to the second jaw member between an open and a closed position. The end effector may also comprise a tissue-cutting element configured to translate with respect to the first jaw and the second jaw, an electrode, and a sensor. The electrosurgical instrument may further comprise an axially moveable cutting member configured to open and close the jaws and a trigger coupled to the axially moveable cutting member. The tissue-cutting element may be positioned at a distal end of the axially movable member.

In another embodiment, an electrosurgical instrument may comprise a handle, an elongate shaft extending distally from the handle, and an indicator configured to provide a sequence of feedback signals during the operational stroke. The electrosurgical instrument may further comprise an end effector coupled to the distal end of the elongate shaft. The end effector may comprise a first jaw member and a second jaw member, where the first jaw member is movable relative to the second jaw member between an open and a closed position. The end effector may also comprise a tissue-cutting element configured to translate with respect to the first jaw and the second jaw, an electrode, and an impedance sensor. The electrosurgical instrument may further comprise an axially moveable cutting member configured to close the jaws during the operational stroke and a ratcheting trigger coupled to the axially moveable cutting member, where the ratcheting trigger is movable between a plurality of discrete positions during an operational stroke. The tissue-cutting element may be positioned at a distal end of the axially movable member.

In yet another embodiment, an electrosurgical instrument may comprise a handle, an elongate shaft extending distally from the handle, and an end effector coupled to the distal end of the elongate shaft. The end effector may comprise a first jaw member and a second jaw member, where the first jaw member is movable relative to the second jaw member between an open and a closed position to clamp tissue in the closed position. The end effector may also comprise a tissue-cutting element configured to translate with respect to the first jaw and the second jaw and an electrode. The electrosurgical instrument may further comprise an axially moveable member configured to distally translate during the operational stroke to close the jaws and a ratcheting trigger coupled to the axially moveable cutting member, where the ratcheting trigger is movable between a plurality of discrete positions during an operational stroke. The tissue-cutting element may be positioned at a distal end of the axially movable member. The electrosurgical instrument may further comprise an indicator configured to verify an independence level in a section of the clamped tissue during the operational stroke.

The foregoing discussion should not be taken as a disavowal of claim scope.

FIGURES

Various features of the embodiments described herein are set forth with particularity in the appended claims. The various embodiments, however, both as to organization and methods of operation, together with advantages thereof, may be understood in accordance with the following description taken in conjunction with the accompanying drawings as follows.

Figure 7:
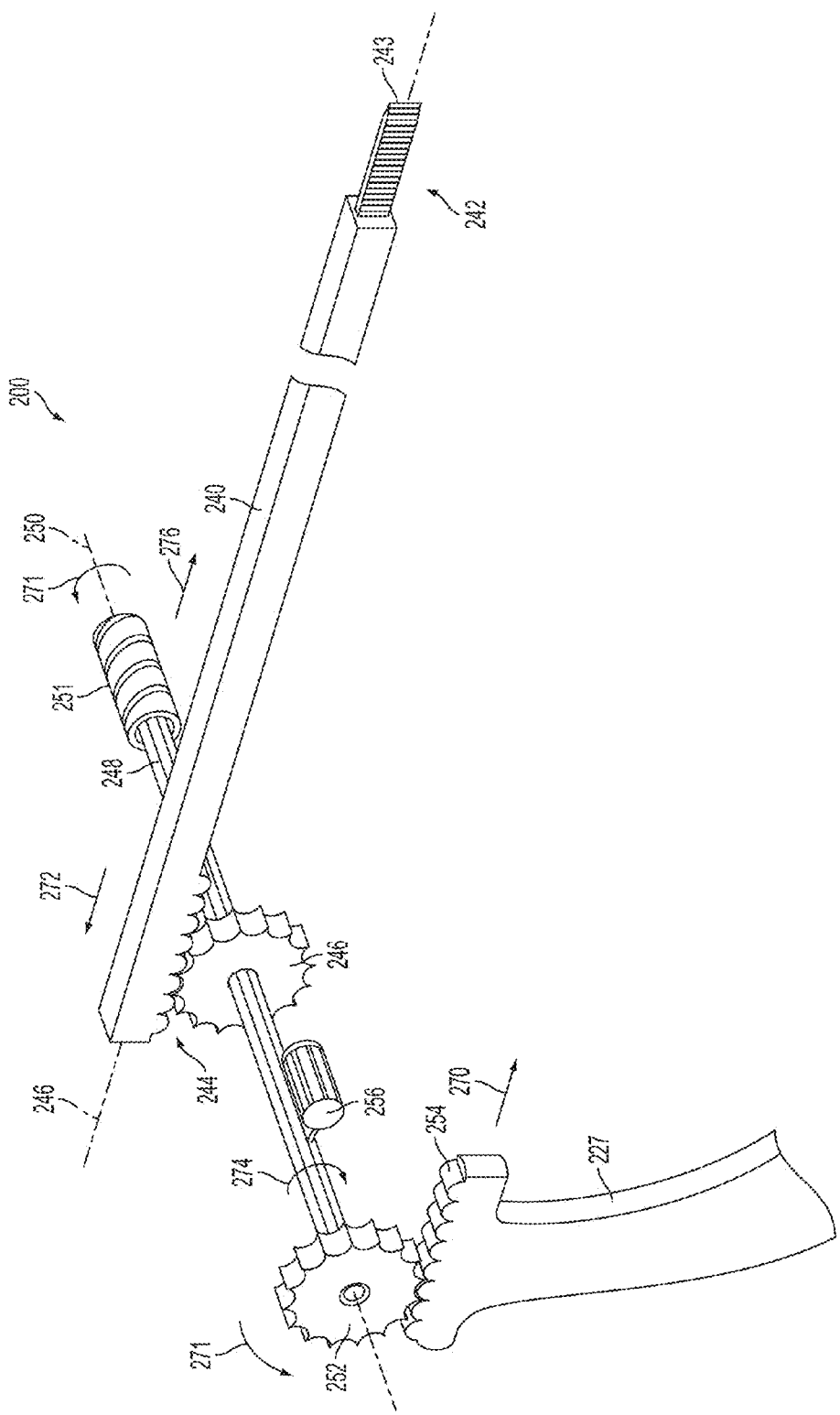
FIG. 7 is a schematic representation of an actuation assembly in accordance with one non-limiting embodiment.
Figure 8:
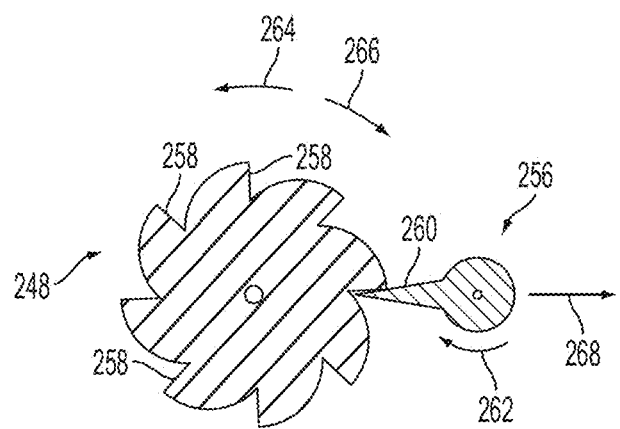

FIG. 8 a cross-sectional view of the engagement between the internal shaft of FIG. 7 and the moveable locking member in accordance with one non-limiting embodiment.

Figure 9:
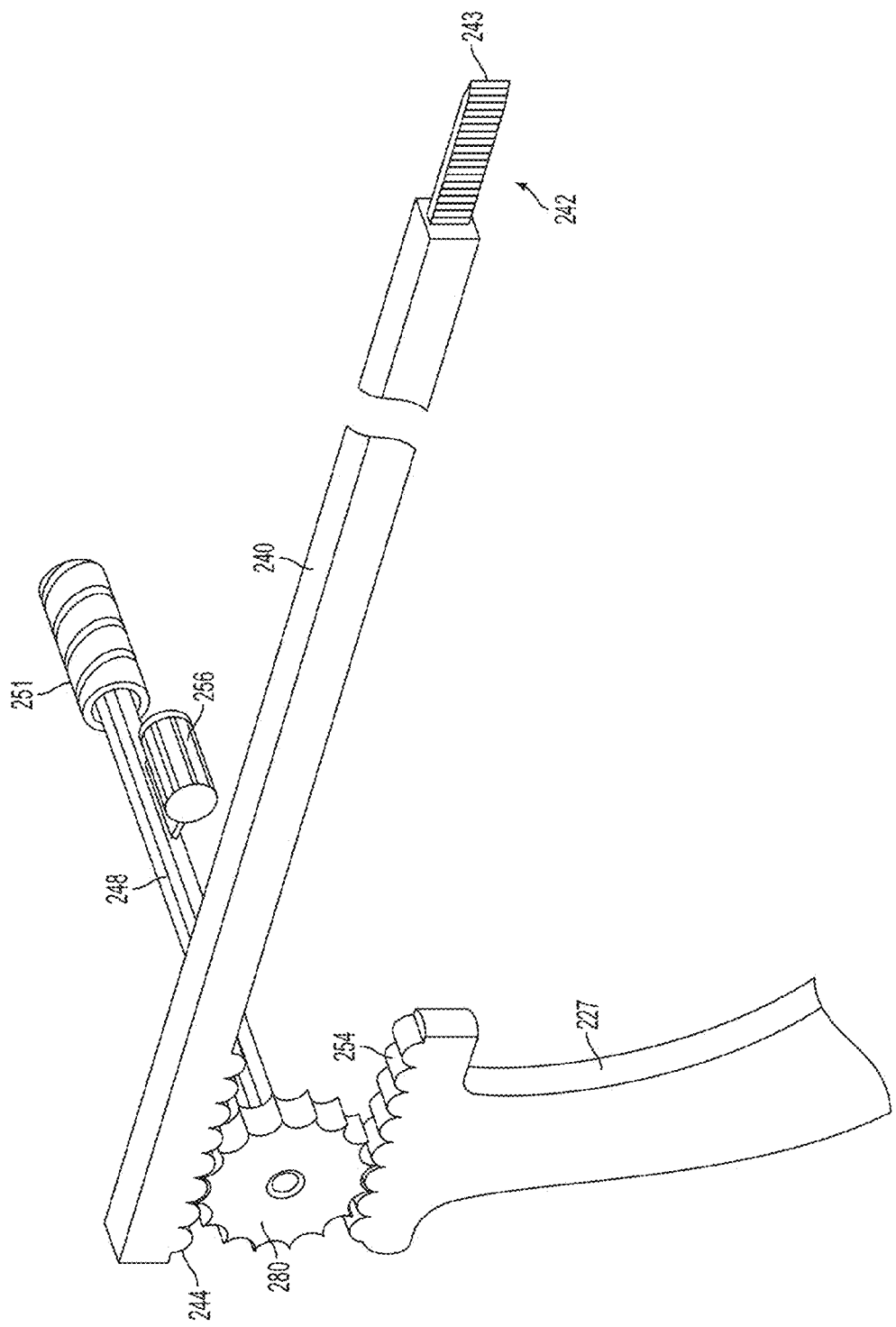

FIG. 9 is a schematic representation of an actuation assembly in accordance with one non-limiting embodiment.

Figure 10:
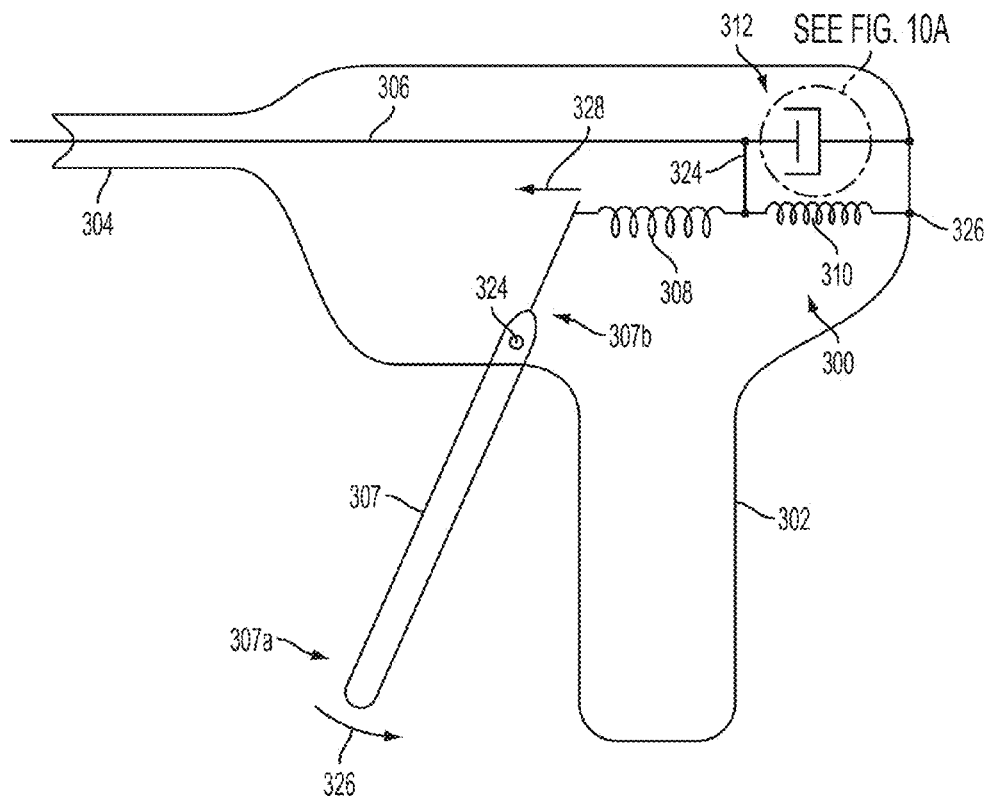

FIG. 10 is a simplified representation of an actuation assembly in accordance with one non-limiting embodiment.

Figure 10A:
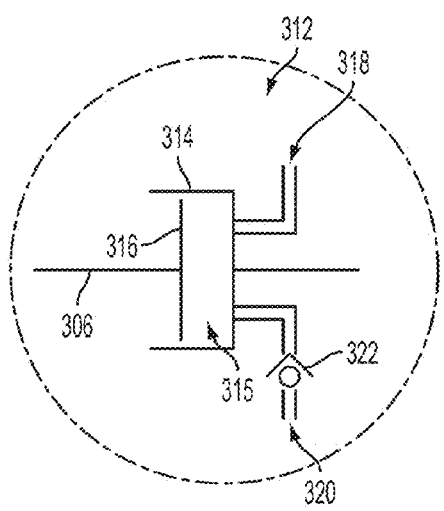

FIG. 10A is a close-up view of the damper of FIG. 10 in accordance with one non-limiting embodiment.

Figure 11:
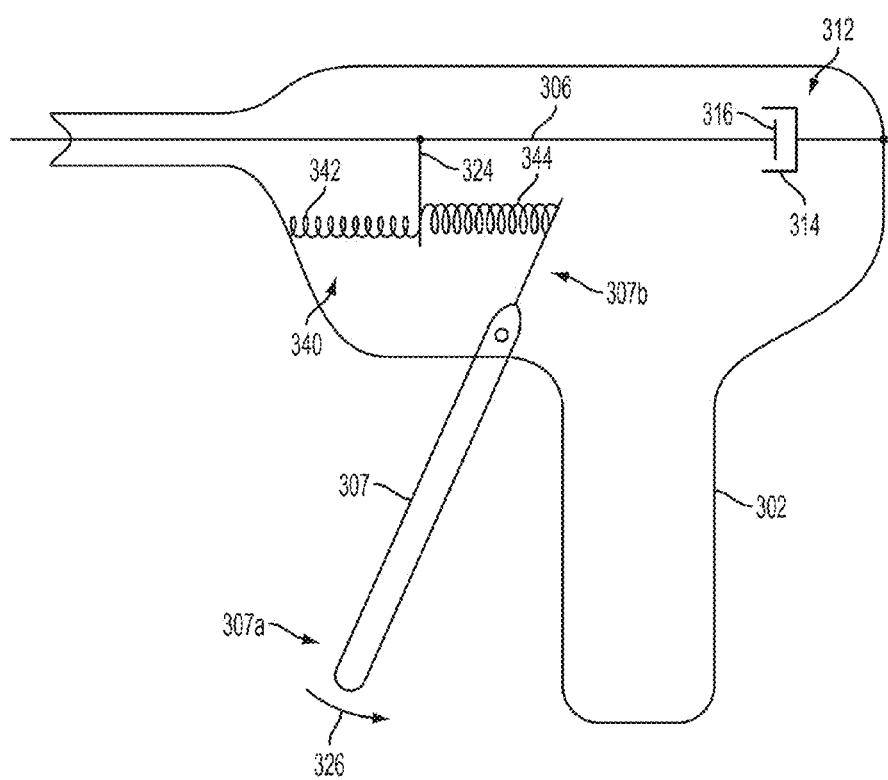

FIG. 11 is a simplified representation of an actuation assembly in accordance with one non-limiting embodiment.

FIGS. 12-15 illustrate a representation of an electrosurgical instrument comprising a linear actuator in accordance with one non-limiting embodiment.

Figure 16:
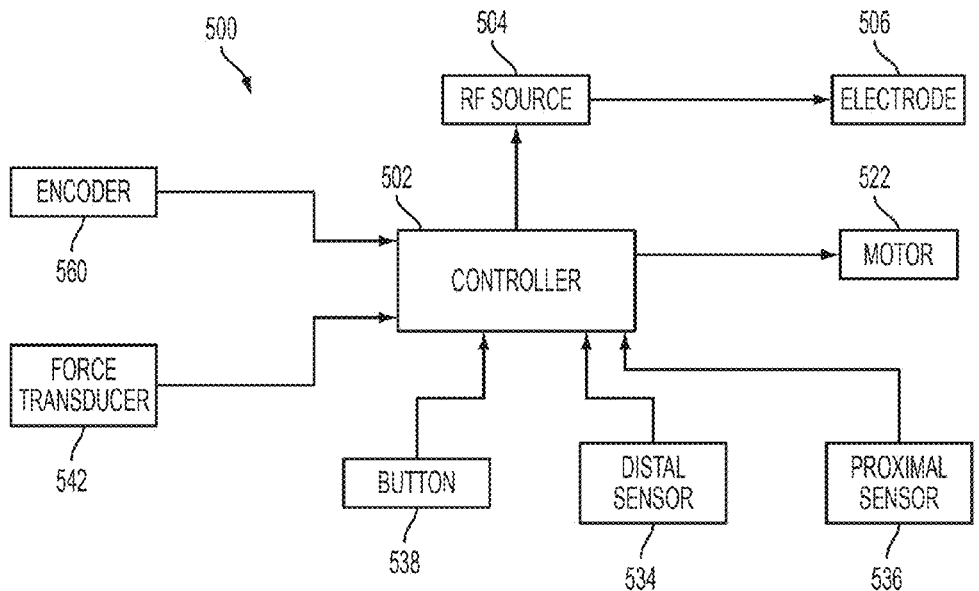

FIG. 16 is a block diagram of a control system of an electrosurgical instrument in accordance with one non-limiting embodiment.

Figure 17:
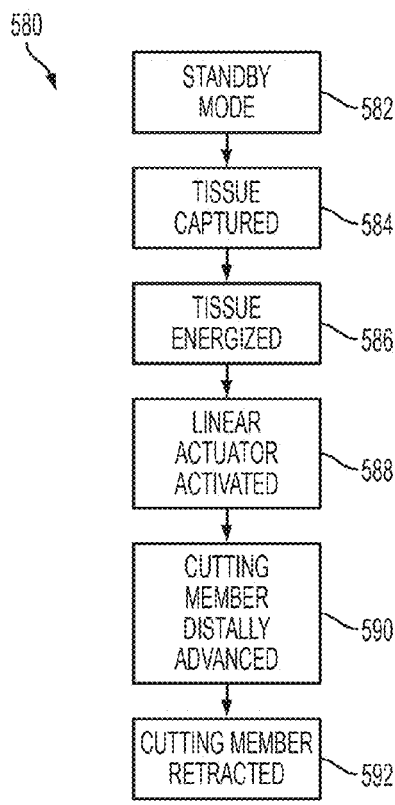

FIG. 17 is a flow chart of the operation of an electrosurgical instrument having a linear actuator in accordance with one non-limiting embodiment.

FIGS. 18-21 illustrate an electrosurgical instrument having a damper in accordance with one non-limiting embodiment.

Figure 18:
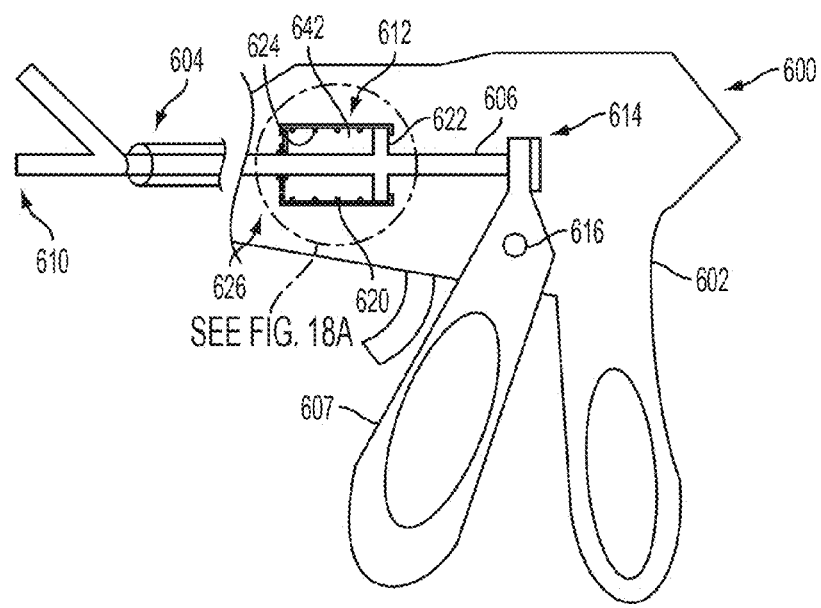
Figure 18A:
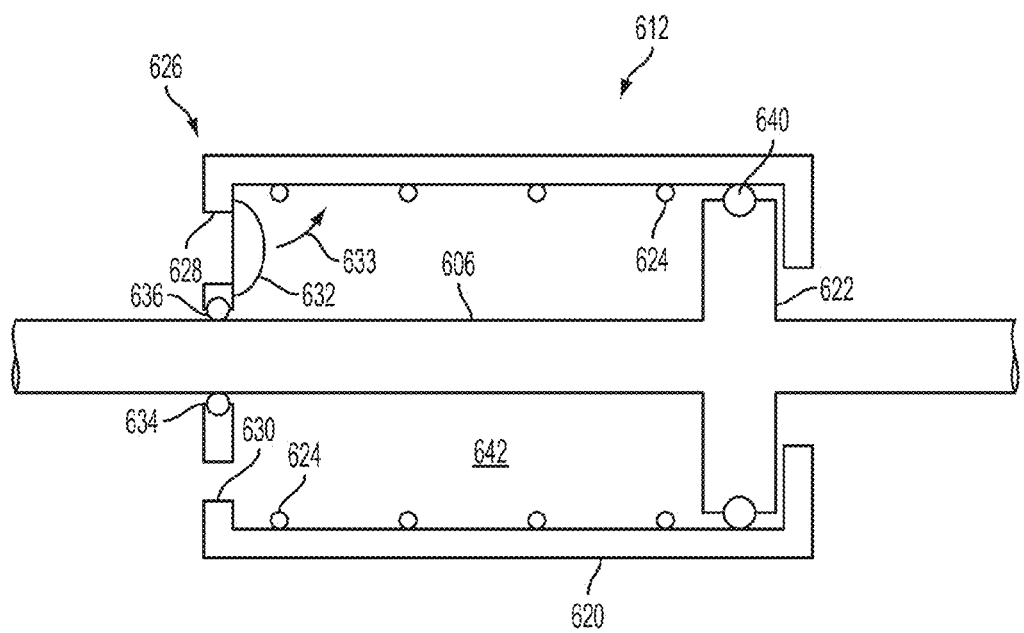

FIG. 18A is an enlarged cross-sectional view of the damper in FIGS. 18-21.

Figure 22:
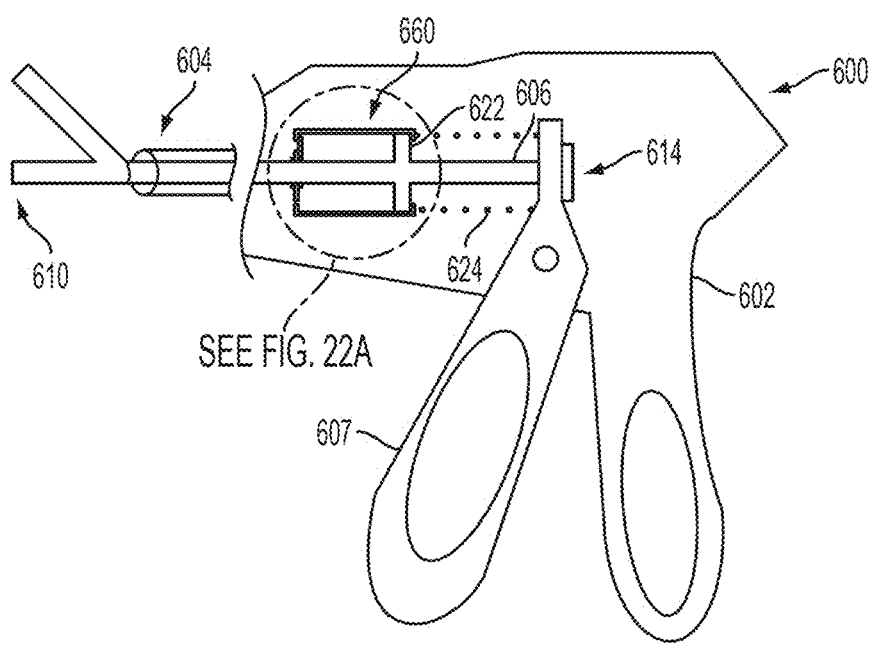
Figure 22A:
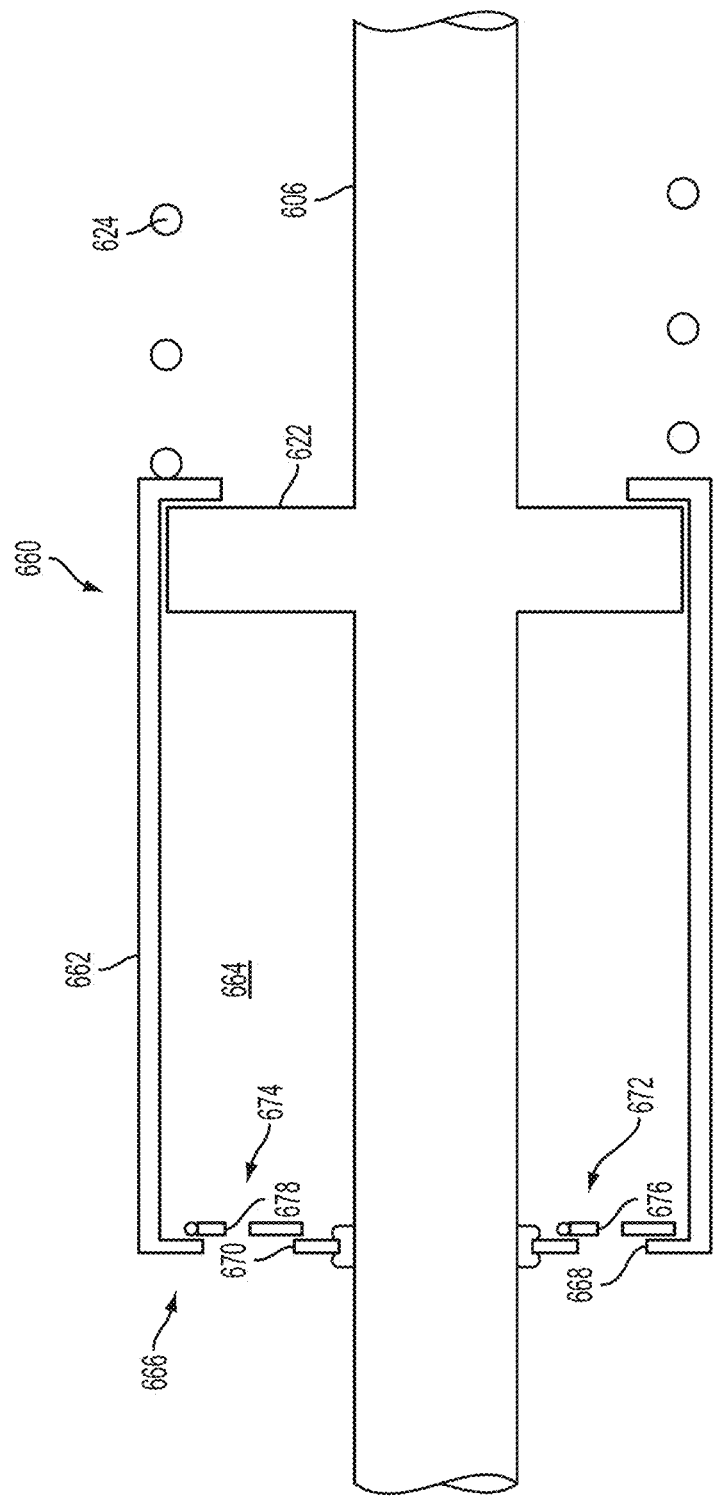
Figure 23:
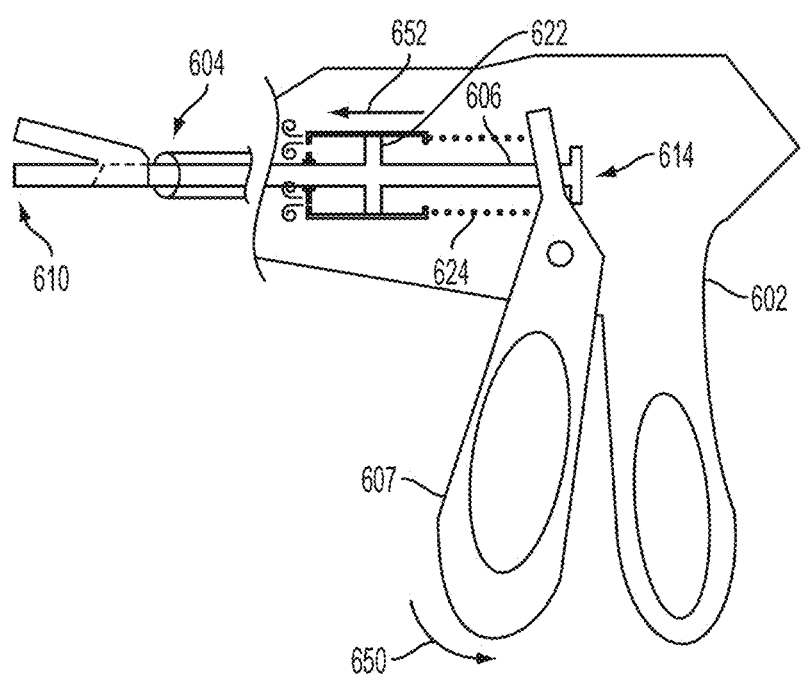
Figure 24:
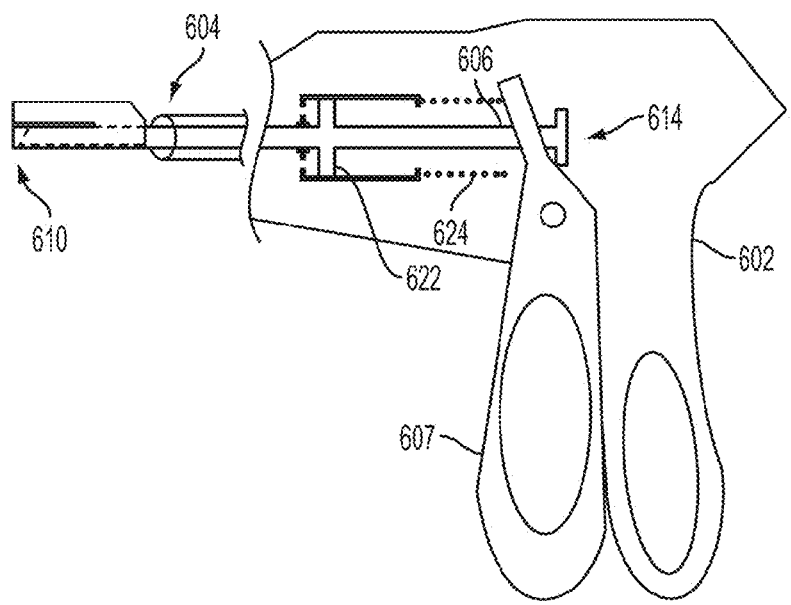
Figure 25:
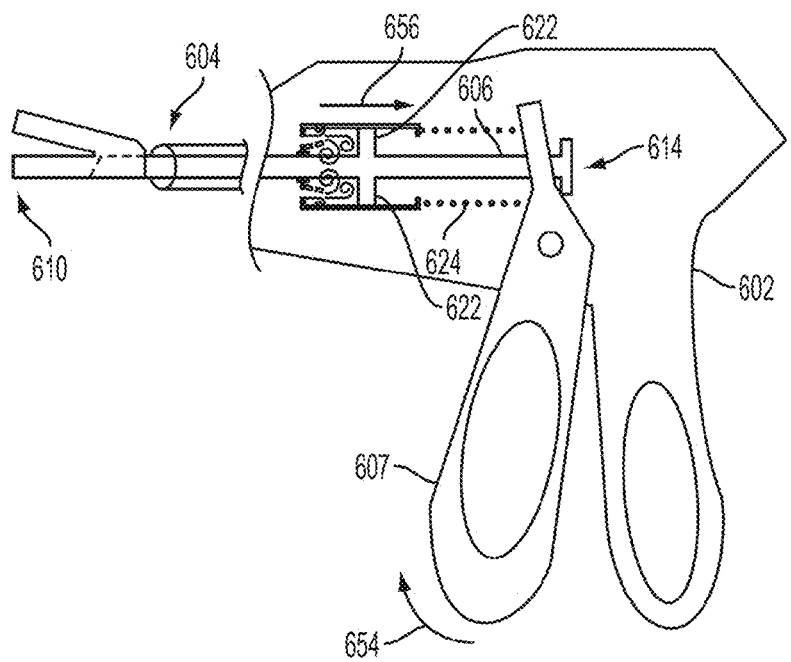

FIGS. 22-25 illustrate an electrosurgical instrument with a damper having two check valves FIG. 22A is an enlarged cross-sectional view of the damper in FIGS. 22-25.

Figure 26:
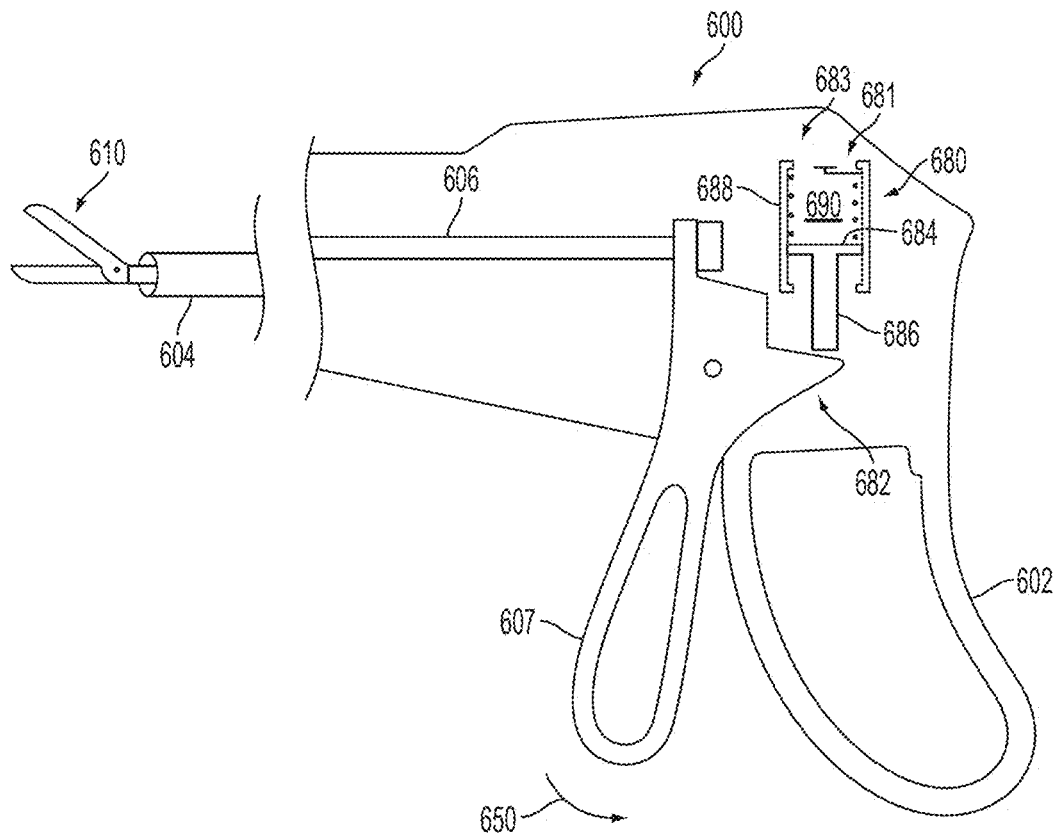

FIG. 26 illustrates a damper that is coupled to a tab of a trigger in accordance with one non-limiting embodiment.

Figure 26A:
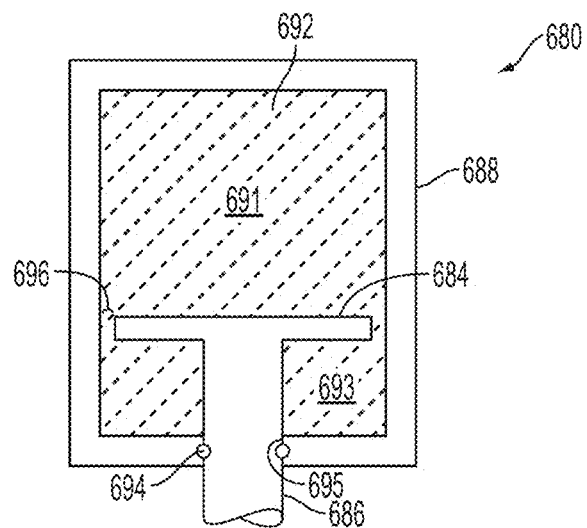

FIG. 26A is an enlarged view of the damper in FIG. 26.

Figure 27:
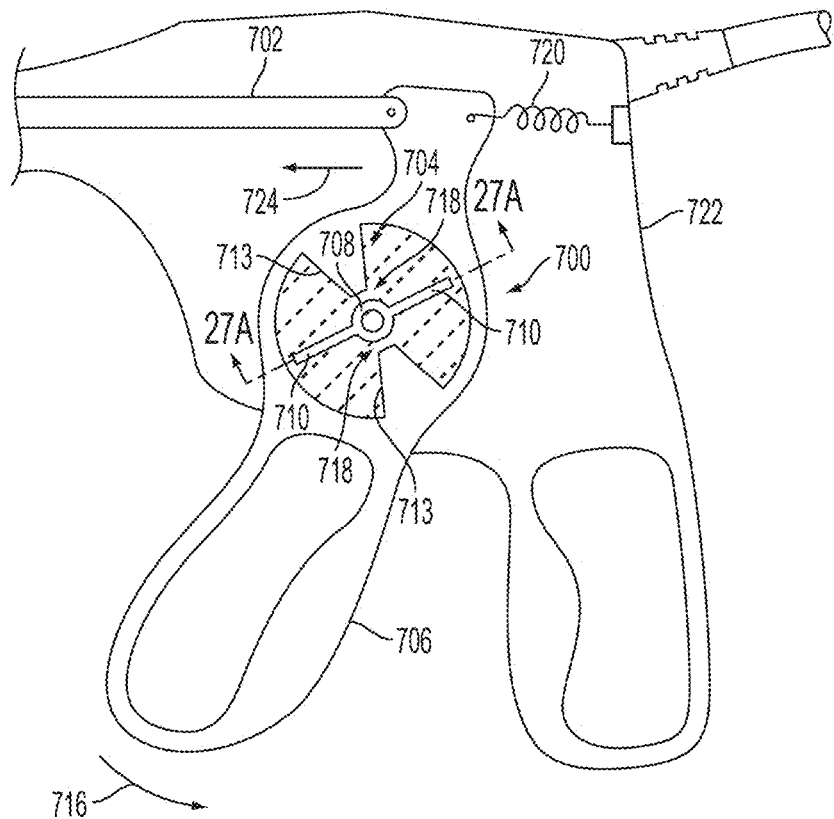

FIG. 27 illustrates a rotary damper in accordance with one non-limiting embodiment.

Figure 27A:
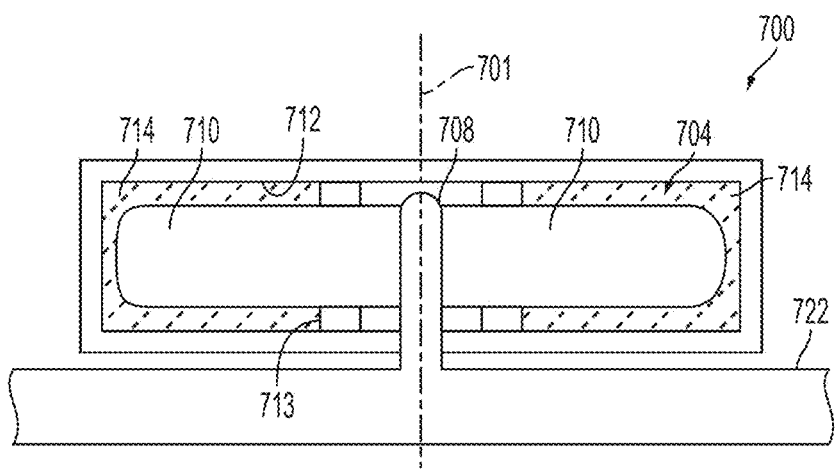

FIG. 27A is a cross-sectional view of the damper in FIG. 27 taken along line 27A-27A.

Figure 28:
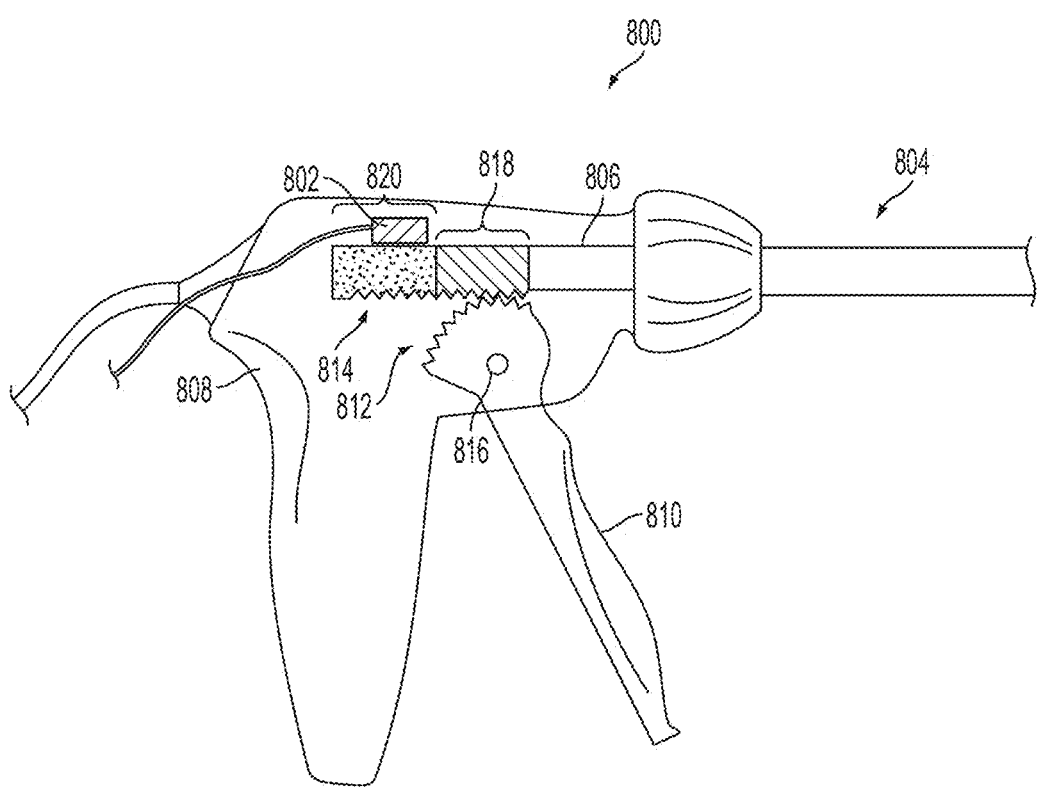

FIG. 28 illustrates an electrosurgical instrument incorporating an electromagnetic brake assembly in accordance with one non-limiting embodiment.

Figure 29:
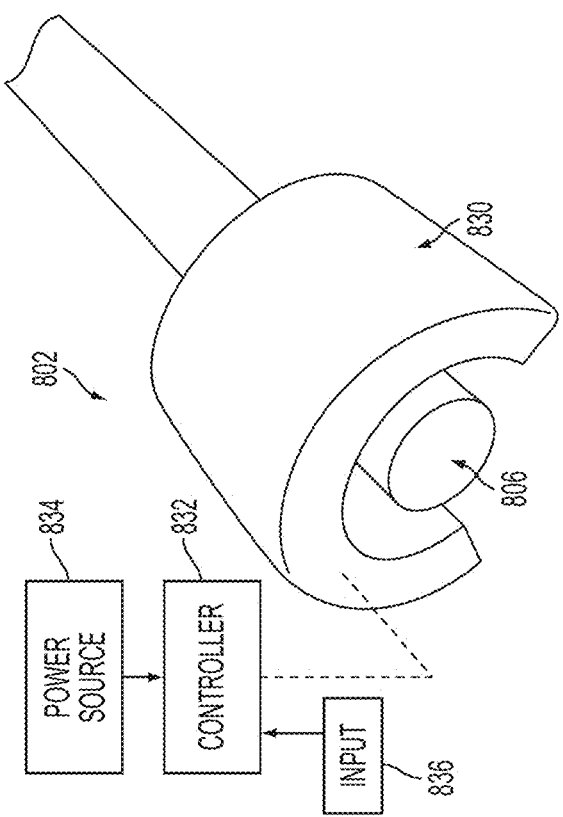

FIG. 29 illustrates an electromagnetic brake assembly in accordance with one non-limiting embodiment.

Figure 30:
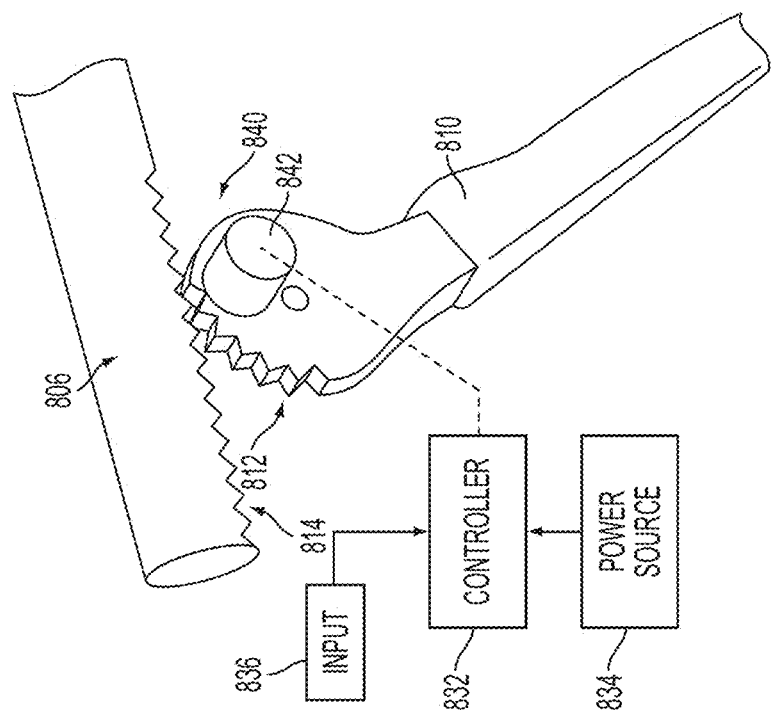

FIG. 30 illustrates an electromagnetic brake assembly in accordance with one non-limiting embodiment.

Figure 31:
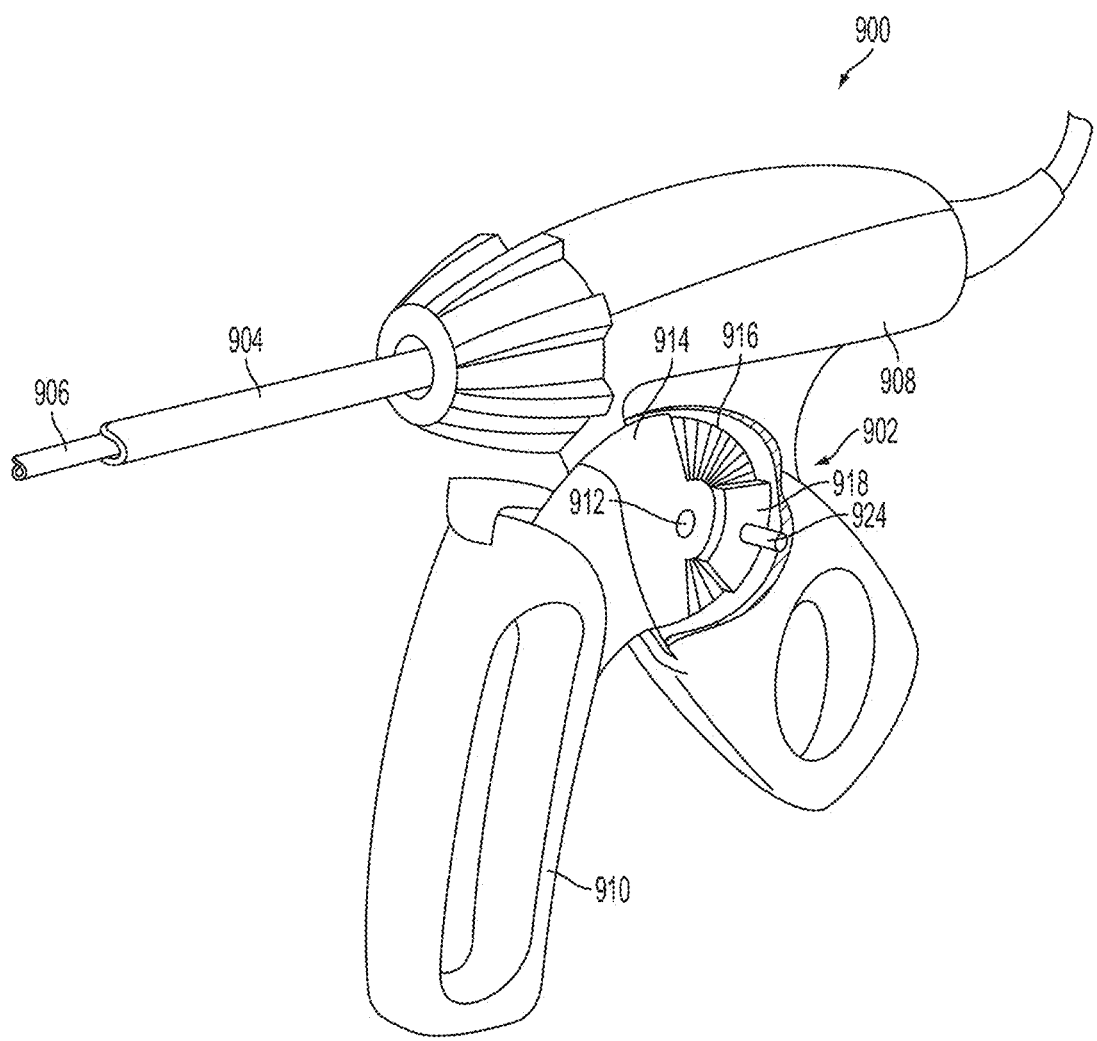

FIG. 31 is a partial cut-away view of an electrosurgical instrument having an electromagnetic brake assembly in accordance with one non-limiting embodiment.

Figure 32:
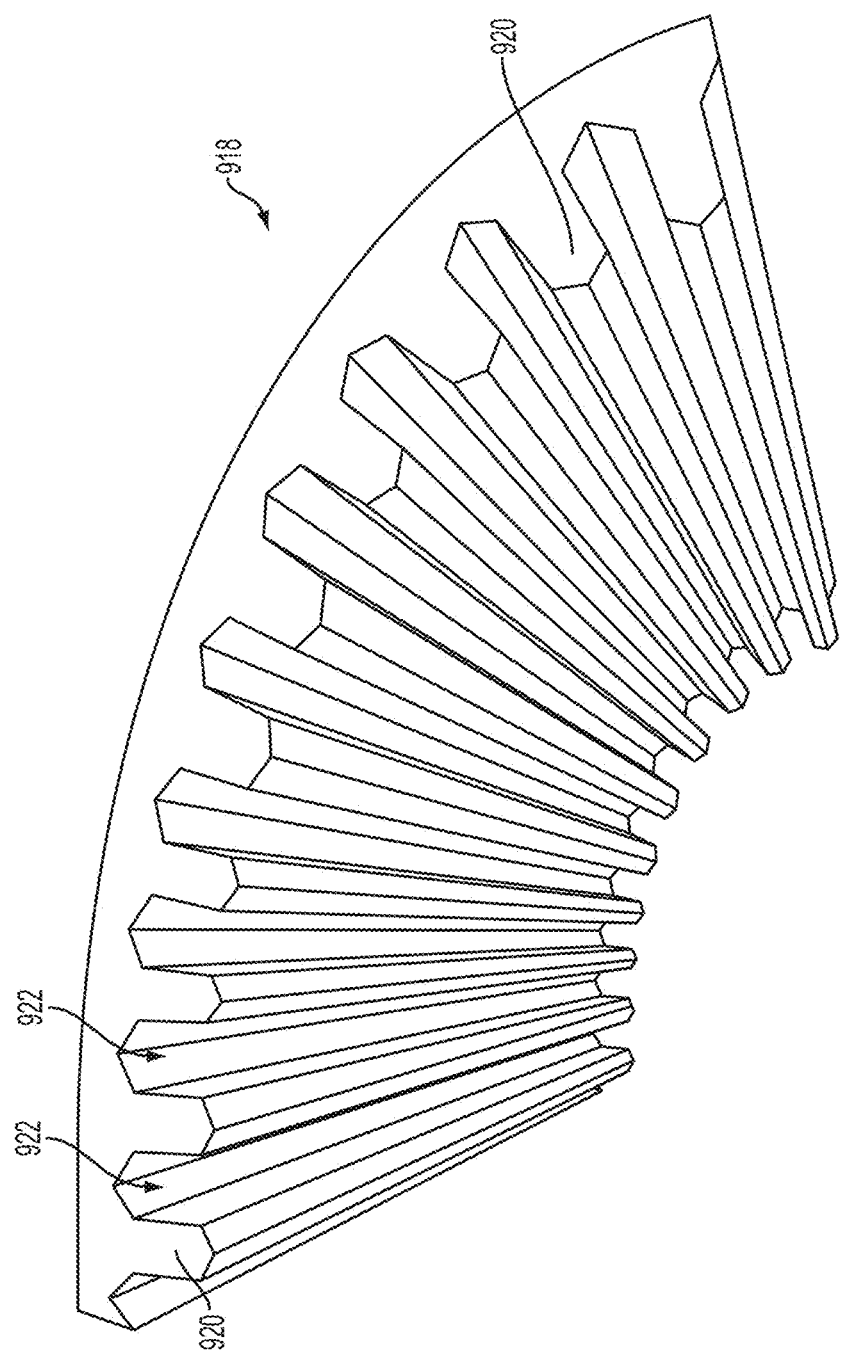

FIG. 32 illustrates an enlarged view of a brake pad in accordance with one non-limiting embodiment.

Figure 33A:
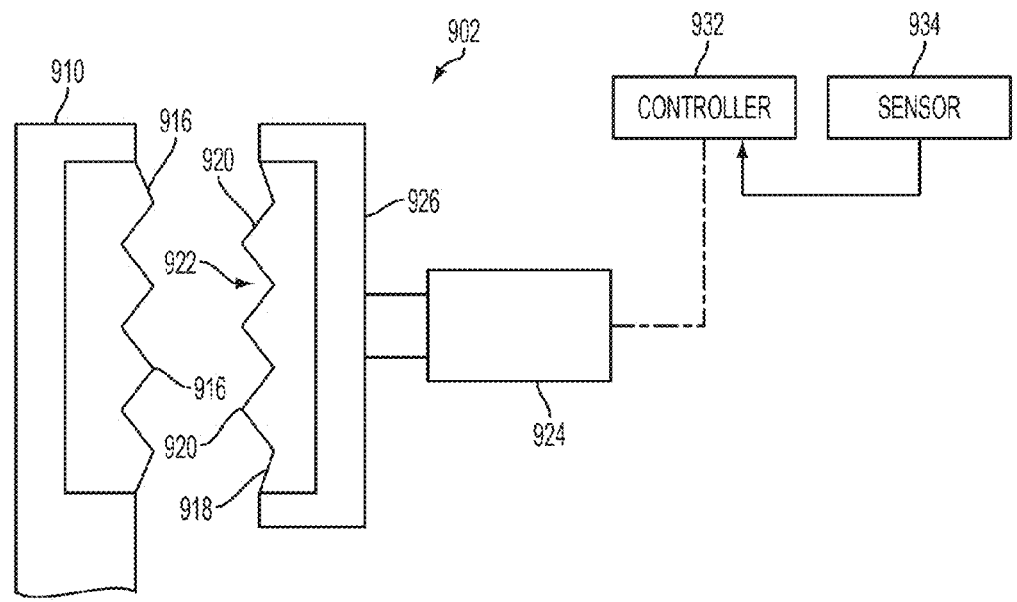
Figure 33B:
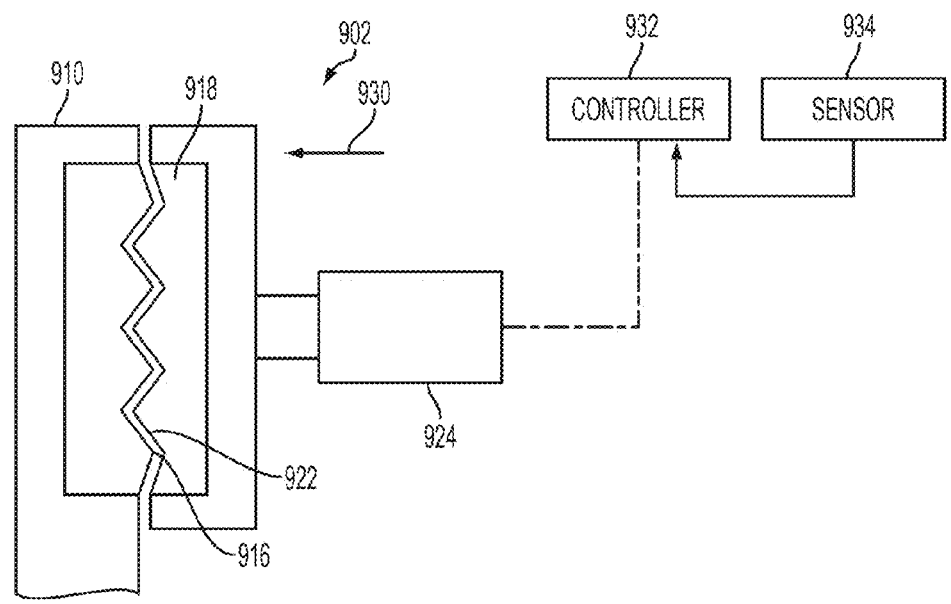

FIGS. 33A and 33B, illustrate the electromagnetic brake assembly in FIG. 31 in various stages of operation.

Figure 34:
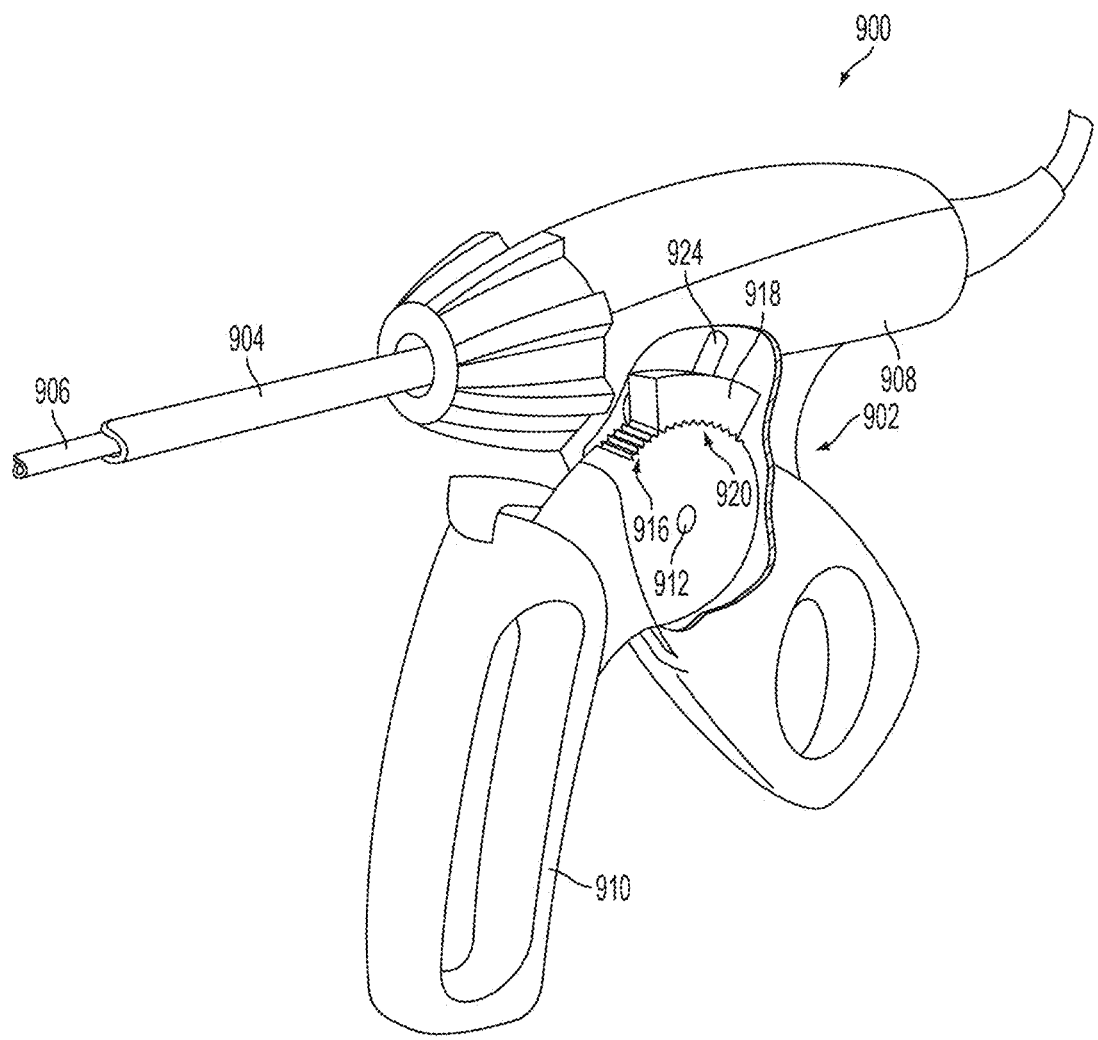

FIG. 34 is a partial cut-away view of an electrosurgical instrument having an electromagnetic brake assembly in accordance with one non-limiting embodiment.

Figure 35:
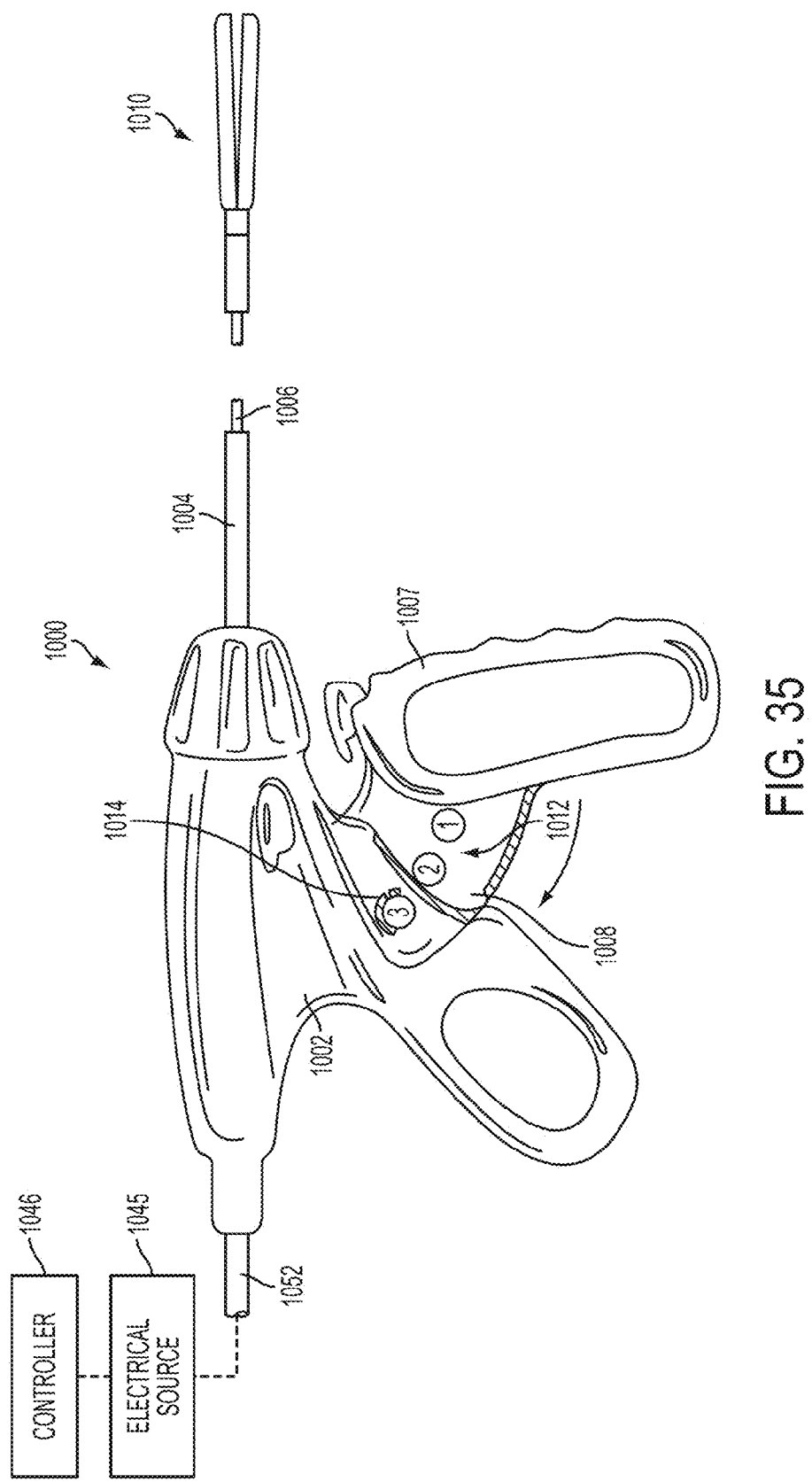

FIG. 35 illustrates an electrosurgical instrument having electromagnetic gates to regulate the operational stroke in accordance with one non-limiting embodiment.

Figure 36A:
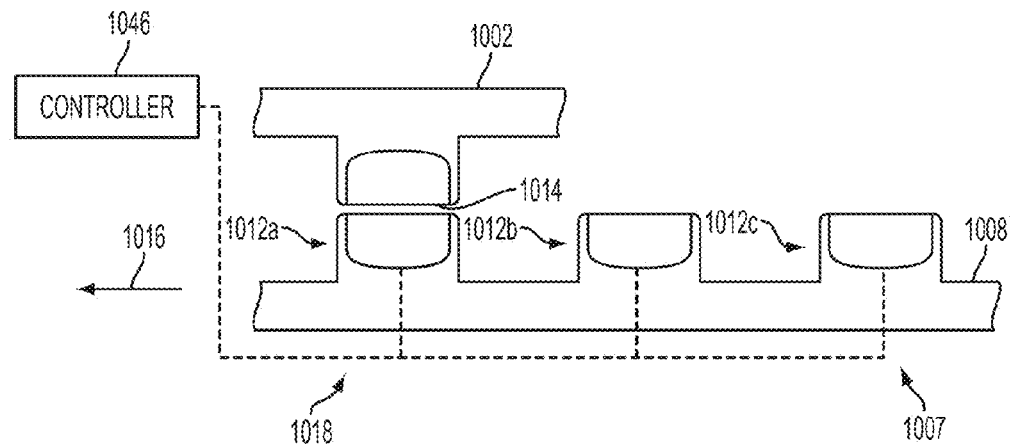
Figure 36B:
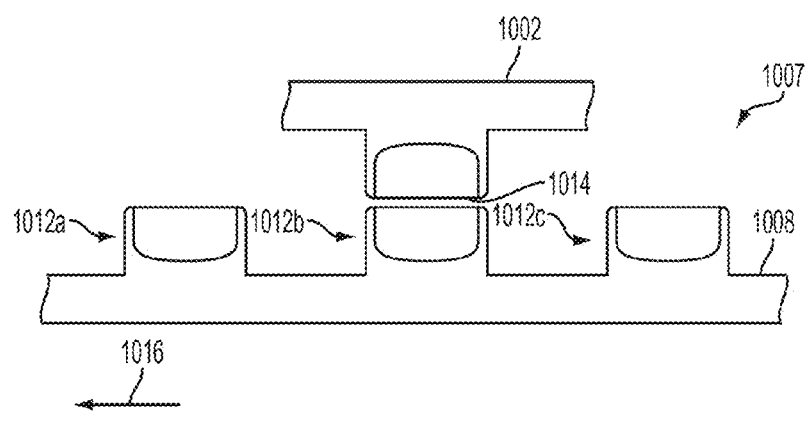
Figure 36C:
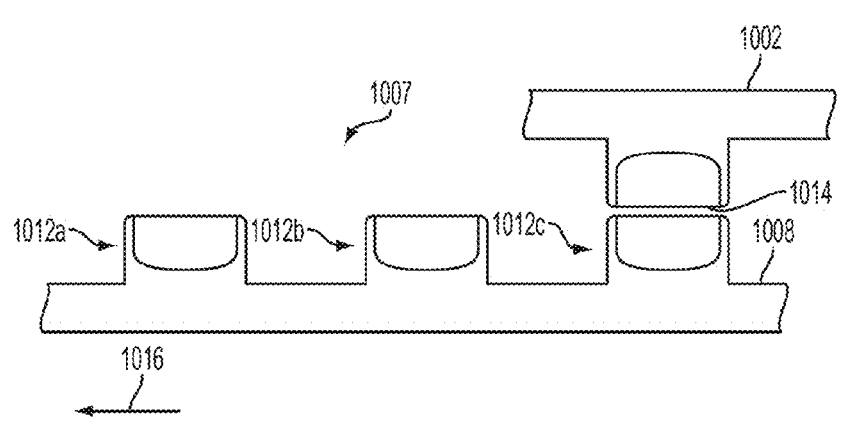

FIGS. 36A, 36B, and 36C are enlarged side views of the trigger web and the electromagnet engaging surface in FIG. 35 during an operational stroke in accordance with one non-limiting embodiment.

Figure 37:
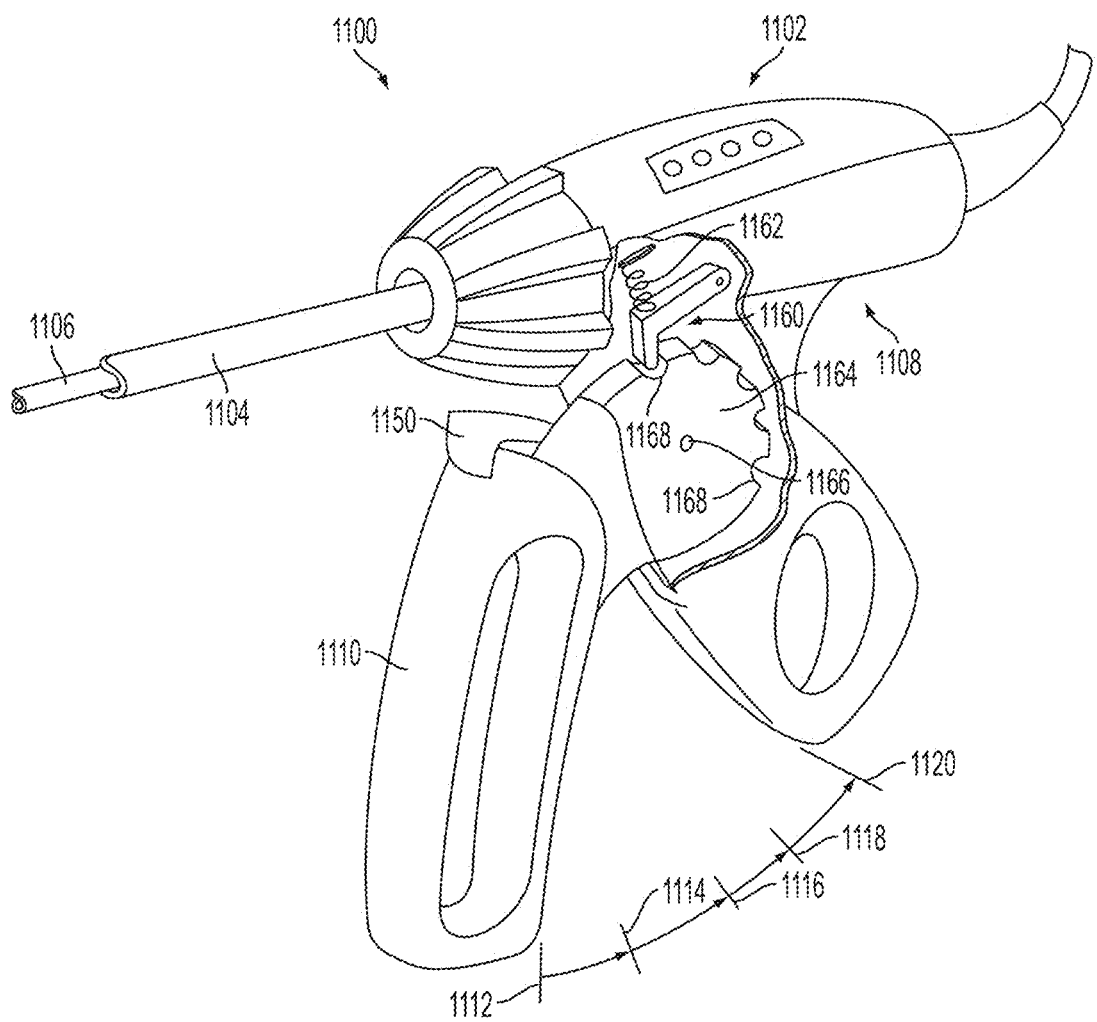

FIG. 37 is a partial cut-away view of an electrosurgical instrument having a feedback indicator in accordance with one non-limiting embodiment.

FIGS. 38A, 38B, 38C, and 38D illustrate the progression of feedback signals provided by the feedback indicator in FIG. 37 in accordance with one non-limiting embodiment.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Various embodiments are directed to apparatuses, systems, and methods for the treatment of tissue. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and illustrative. Variations and changes thereto may be made without departing from the scope of the claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

The entire disclosures of the following non-provisional United States patents are hereby incorporated by reference herein:

U.S. Pat. No. 7,381,209, entitled ELECTROSURGICAL INSTRUMENT;

U.S. Pat. No. 7,354,440, entitled ELECTROSURGICAL INSTRUMENT AND METHOD OF USE;

U.S. Pat. No. 7,311,709, entitled ELECTROSURGICAL INSTRUMENT AND METHOD OF USE;

U.S. Pat. No. 7,309,849, entitled POLYMER COMPOSITIONS EXHIBITING A PTC PROPERTY AND METHODS OF FABRICATION;

U.S. Pat. No. 7,220,951, entitled SURGICAL SEALING SURFACES AND METHODS OF USE;

U.S. Pat. No. 7,189,233, entitled ELECTROSURGICAL INSTRUMENT;

U.S. Pat. No. 7,186,253, entitled ELECTROSURGICAL JAW STRUCTURE FOR CONTROLLED ENERGY DELIVERY;

U.S. Pat. No. 7,169,146, entitled ELECTROSURGICAL PROBE AND METHOD OF USE;

U.S. Pat. No. 7,125,409, entitled ELECTROSURGICAL WORKING END FOR CONTROLLED ENERGY DELIVERY; and U.S. Pat. No. 7,112,201, entitled ELECTROSURGICAL INSTRUMENT AND METHOD OF USE.

Various embodiments of systems and methods of the invention relate to creating thermal "welds" or "fusion" within native tissue volumes. The alternative terms of tissue "welding" and tissue "fusion" may be used interchangeably herein to describe thermal treatments of a targeted tissue volume that result in a substantially uniform fused-together tissue mass, for example, in welding blood vessels that exhibit substantial burst strength immediately post-treatment. The strength of such welds is particularly useful for (i) permanently sealing blood vessels in vessel transection procedures; (ii) welding organ margins in resection procedures; (iii) welding other anatomic ducts wherein permanent closure is required; and also (iv) for performing vessel anastomosis, vessel closure or other procedures that join together anatomic structures or portions thereof. The welding or fusion of tissue as disclosed herein is to be distinguished from "coagulation", "hemostasis" and other similar descriptive terms that generally relate to the collapse and occlusion of blood flow within small blood vessels or vascularized tissue. For example, any surface application of thermal energy can cause coagulation or hemostasis—but does not fall into the category of "welding" as the term is used herein. Such surface coagulation does not create a weld that provides any substantial strength in the treated tissue.

At the molecular level, the phenomena of truly "welding" tissue as disclosed herein may result from the thermally-induced denaturation of collagen and other protein molecules in a targeted tissue volume to create a transient liquid or gel-like proteinaceous amalgam. A selected energy density is provided in the targeted tissue to cause hydrothermal breakdown of intra- and intermolecular hydrogen crosslinks in collagen and other proteins. The denatured amalgam is maintained at a selected level of hydration—without desiccation—for a selected time interval which can be very brief. The targeted tissue volume is maintained under a selected very high level of mechanical compression to insure that the unwound strands of the denatured proteins are in close proximity to allow their intertwining and entanglement. Upon thermal relaxation, the intermixed amalgam results in protein entanglement as re-crosslinking or renaturation occurs to thereby cause a uniform fused-together mass.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Various embodiments disclosed herein provide electrosurgical jaw structures adapted for transecting captured tissue between the jaws and for contemporaneously welding the captured tissue margins with controlled application of RF energy. The jaw structures may comprise a scoring element which may cut or score tissue independently of the tissue capturing and welding functions of the jaw structures. The jaw structures may comprise first and second opposing jaws that carry positive temperature coefficient (PTC) bodies for modulating RF energy delivery to the engaged tissue.

A surgical instrument can be configured to supply energy, such as electrical energy and/or heat energy, to the tissue of a patient. For example, various embodiments disclosed herein provide electrosurgical jaw structures adapted for transecting captured tissue between the jaws and for contemporaneously welding the captured tissue margins with controlled application of RF energy. In some embodiments, the electrosurgical jaw structures may be adapted to coagulate the captured tissue rather than weld the captured tissue. All such arrangements and implementations are intended to be within the scope of this disclosure.

Figure 1:
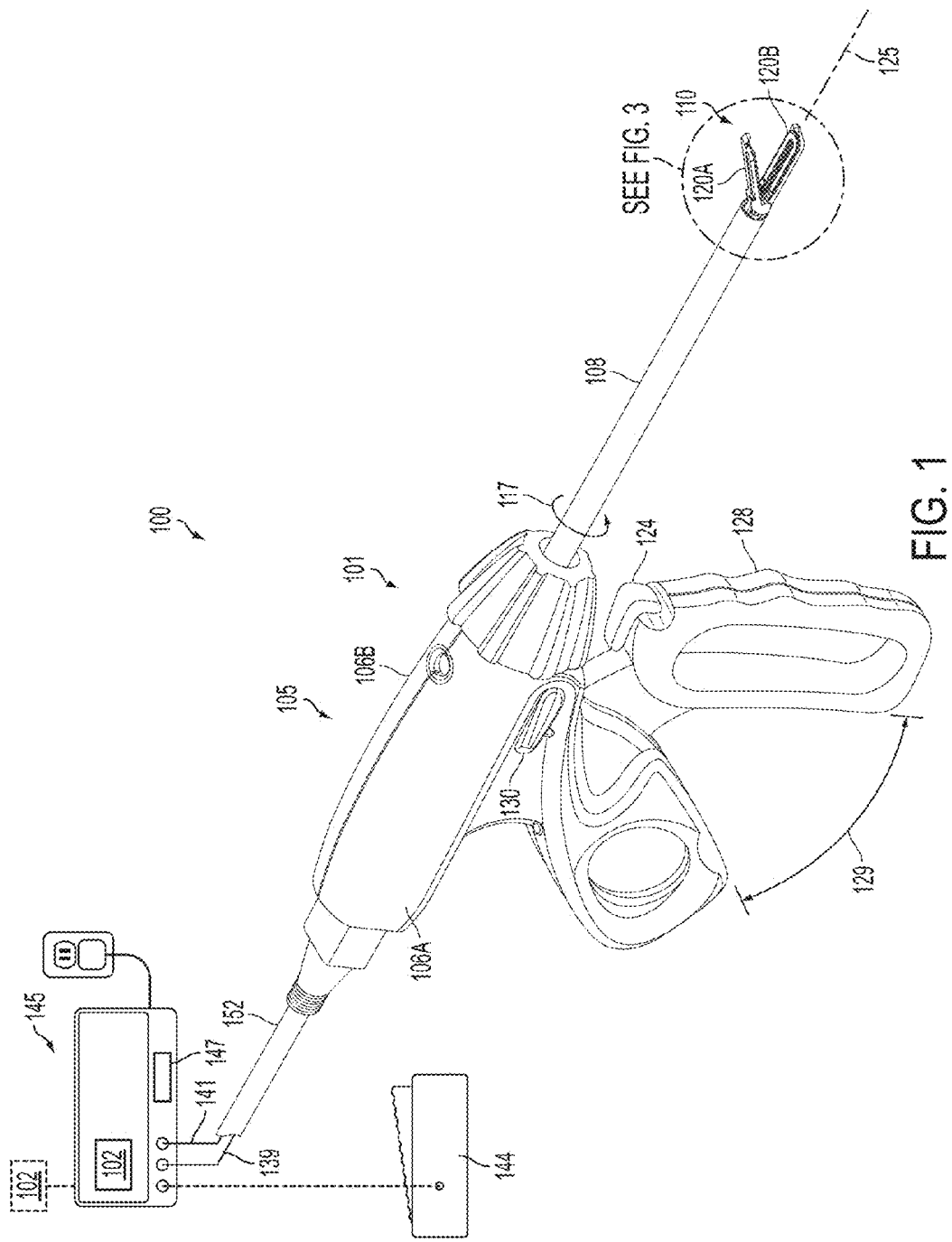
FIG. 1 is a perspective view of a surgical instrument according to a non-limiting embodiment.

Referring now to FIG. 1, an electrosurgical system 100 is shown in accordance with various embodiments. The electrosurgical system 100 includes an electrosurgical instrument 101 that may comprise a proximal handle 105, a distal working end or end effector 110 and an introducer or elongate shaft 108 disposed in-between. The end effector 110 may comprise a set of openable-closeable jaws with straight or curved jaws—an upper first jaw 120A and a lower second jaw 120B. The first jaw 120A and the second jaw 120B may each comprise an elongate slot or channel 142A and 142B (see FIG. 3), respectively, disposed outwardly along their respective middle portions.

The electrosurgical system 100 can be configured to supply energy, such as electrical energy, ultrasonic energy, and/or heat energy, for example, to the tissue of a patient. In one embodiment, the electrosurgical system 100 includes a generator 145 in electrical communication with the electrosurgical instrument 101. The generator 145 is connected to electrosurgical instrument 101 via a suitable transmission medium such as a cable 152. In one embodiment, the generator 145 is coupled to a controller, such as a control unit 102, for example. In various embodiments, the control unit 102 may be formed integrally with the generator 145 or may be provided as a separate circuit module or device electrically coupled to the generator 145 (shown in phantom to illustrate this option). Although in the presently disclosed embodiment, the generator 145 is shown separate from the electrosurgical instrument 101, in one embodiment, the generator 145 (and/or or the control unit 102) may be formed integrally with the electrosurgical instrument 101 to form a unitary electrosurgical system 100.

The generator 145 may comprise an input device 147 located on a front panel of the generator 145 console. The input device 147 may comprise any suitable device that generates signals suitable for programming the operation of the generator 145, such as a keyboard, or input port, for example. In one embodiment, various electrodes in the first jaw 120A and the second jaw 120B may be coupled to the generator 145. A cable 152 may comprise multiple electrical conductors for the application of electrical energy to positive (+) and negative (−) electrodes of the electrosurgical instrument 101. The control unit 102 may be used to activate electrical source 145. In various embodiments, the generator 145 may comprise an RF source, an ultrasonic source, a direct current source, and/or any other suitable type of electrical energy source, for example.

In various embodiments, the electrosurgical system 100 may comprise at least one supply conductor 139 and at least one return conductor 141, wherein current can be supplied to electrosurgical instrument 101 via the supply conductor 139 and wherein the current can flow back to the generator 145 via return conductor 141. In various embodiments, the supply conductor 139 and the return conductor 141 may comprise insulated wires and/or any other suitable type of conductor. In certain embodiments, as described below, the supply conductor 139 and the return conductor 141 may be contained within and/or may comprise the cable 152 extending between, or at least partially between, the generator 145 and the end effector 110 of the electrosurgical instrument 101. In any event, the generator 145 can be configured to apply a sufficient voltage differential between the supply conductor 139 and the return conductor 141 such that sufficient current can be supplied to the end effector 110.

Figure 2:
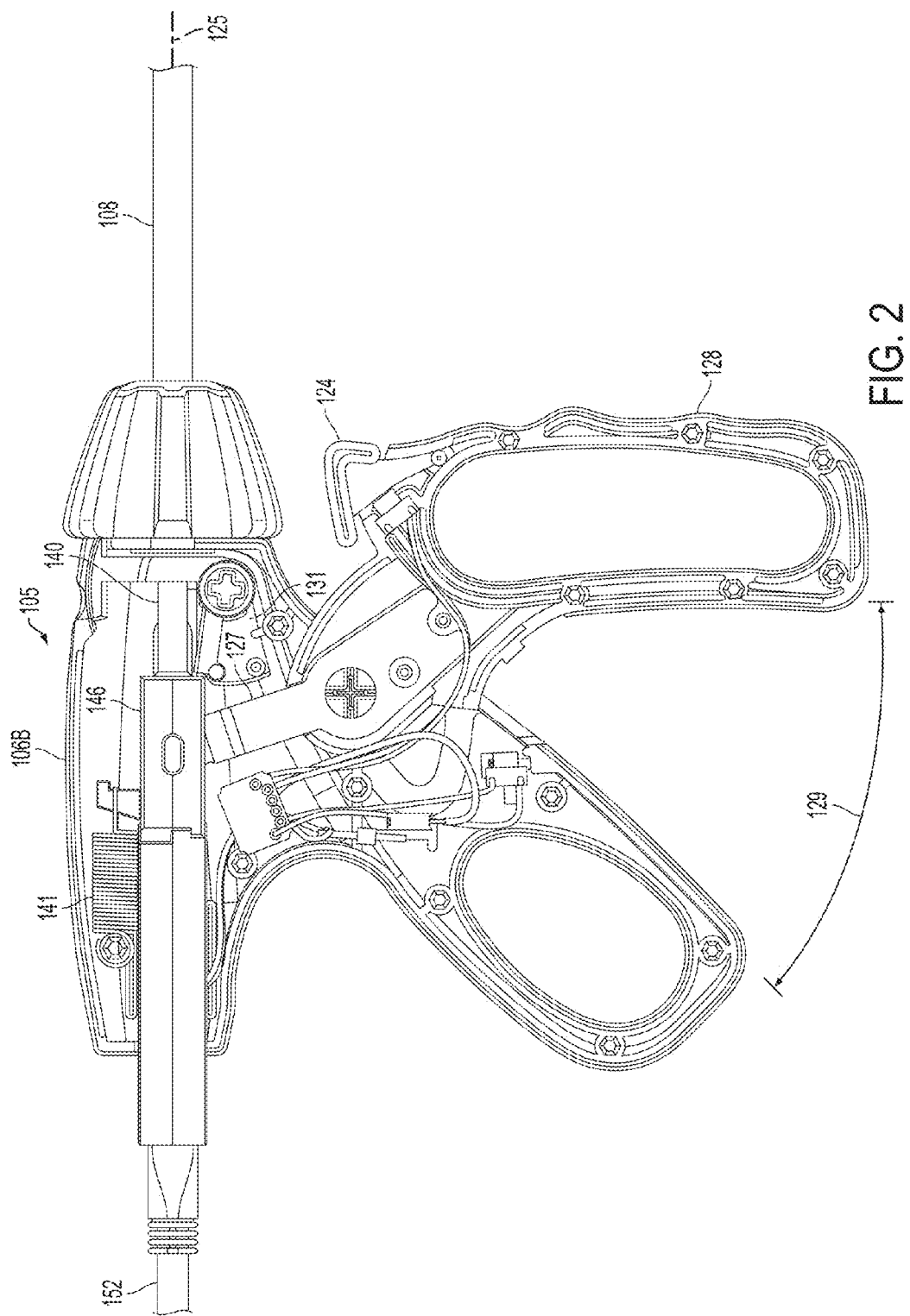
FIG. 2 is a side view of a handle of the surgical instrument of FIG. 1 with a half of a handle body removed to illustrate some of the components therein.

Moving now to FIG. 2, a side view of the handle 105 is shown with half of a first handle body 106A (see FIG. 1) removed to illustrate various components within second handle body 106B. The handle 105 may comprise a lever arm 128 (e.g., a trigger) which may be pulled along a path 129. The lever arm 128 may be coupled to an axially moveable member 140 disposed within elongate shaft 108 by a shuttle 146 operably engaged to an extension 127 of lever arm 128. The shuttle 146 may further be connected to a biasing device, such as a spring 141, which may also be connected to the second handle body 106B, to bias the shuttle 146 and thus the axially moveable member 140 in a proximal direction, thereby urging the jaws 120A and 120B to an open position as seen in FIG. 1. Also, referring to FIGS. 1 and 2, a locking member 131 (see FIG. 2) may be moved by a locking switch 130 (see FIG. 1) between a locked position, where the shuttle 146 is substantially prevented from moving distally as illustrated, and an unlocked position, where the shuttle 146 may be allowed to freely move in the distal direction, toward the elongate shaft 108. The handle 105 can be any type of pistol-grip or other type of handle known in the art that is configured to carry actuator levers, triggers or sliders for actuating the first jaw 120A and the second jaw 120B. The elongate shaft 108 may have a cylindrical or rectangular cross-section, for example, and can comprise a thin-wall tubular sleeve that extends from handle 105. The elongate shaft 108 may include a bore extending therethrough for carrying actuator mechanisms, for example, the axially moveable member 140, for actuating the jaws and for carrying electrical leads for delivery of electrical energy to electrosurgical components of the end effector 110.

The end effector 110 may be adapted for capturing and transecting tissue and for the contemporaneously welding the captured tissue with controlled application of energy (e.g., RF energy). The first jaw 120A and the second jaw 120B may close to thereby capture or engage tissue about a longitudinal axis 125 defined by the axially moveable member 140. The first jaw 120A and second jaw 120B may also apply compression to the tissue. In some embodiments, the elongate shaft 108, along with first jaw 120A and second jaw 120B, can be rotated a full 360° degrees, as shown by arrow 117 (FIG. 1), relative to handle 105 through, for example, a rotary triple contact. The first jaw 120A and the second jaw 120B can remain openable and/or closeable while rotated.

Figure 3:
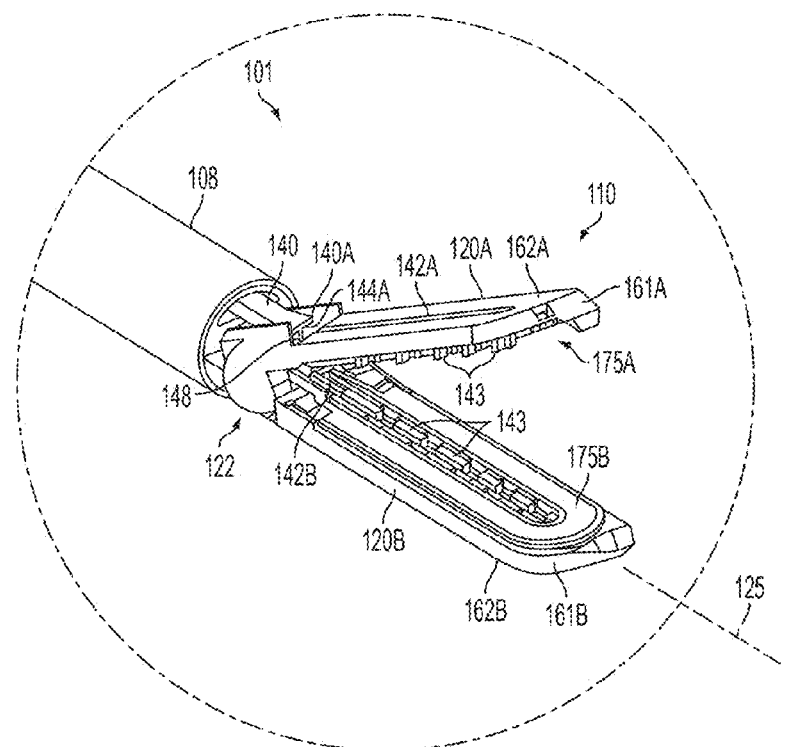
FIG. 3 is a perspective view of an end effector of the surgical instrument of FIG. 1 illustrated in an open configuration; the distal end of an axially moveable member is illustrated in a retracted position.
Figure 4:
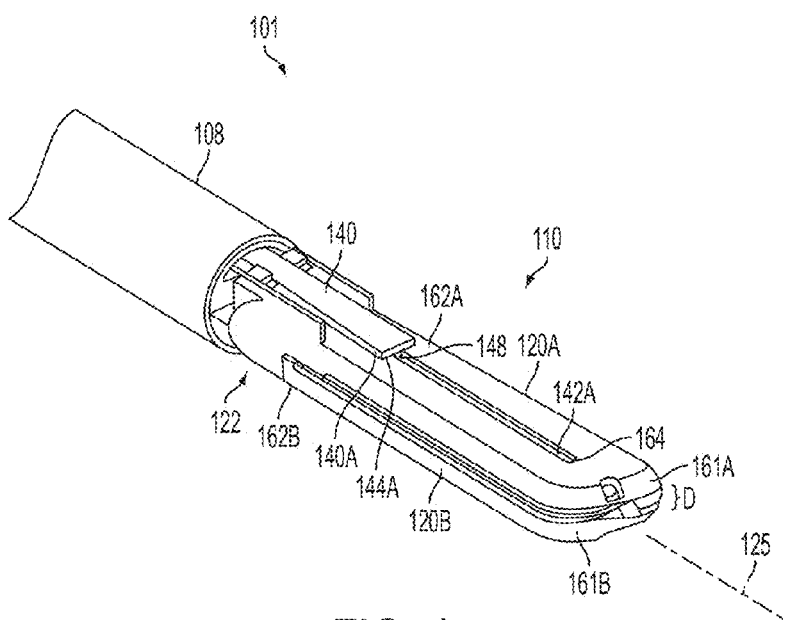
FIG. 4 is a perspective view of the end effector of the surgical instrument of FIG. 1 illustrated in a closed configuration; the distal end of the axially moveable member is illustrated in a partially advanced position.

FIGS. 3 and 4 illustrate perspective views of the end effector 110 in accordance with one non-limiting embodiment. FIG. 3 shows end the effector 110 in an open configuration and FIG. 4 shows the end effector 110 in a closed configuration. As noted above, the end effector 110 may comprise the upper first jaw 120A and the lower second jaw 120B. Further, the first jaw 120A and second jaw 120B may each have tissue-gripping elements, such as teeth 143, disposed on the inner portions of first jaw 120A and second jaw 120B. The first jaw 120A may comprise an upper first jaw body 161A with an upper first outward-facing surface 162A and an upper first energy delivery surface 175A. The second jaw 120B may comprise a lower second jaw body 161B with a lower second outward-facing surface 162B and a lower second energy delivery surface 175B. The first energy delivery surface 175A and the second energy delivery surface 175B may both extend in a "U" shape about the distal end of the end effector 110.

Figure 5:
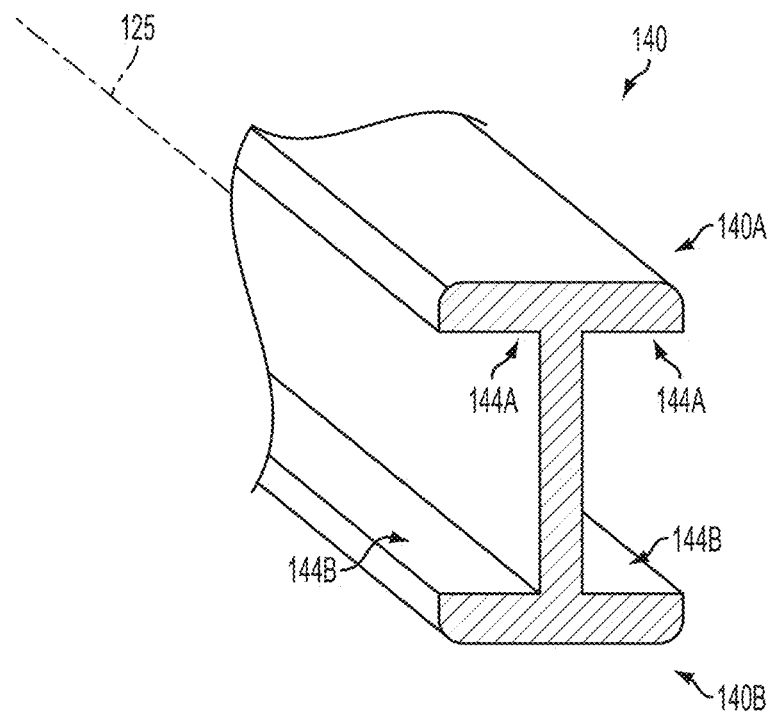
FIG. 5 is a perspective sectional view of a portion of an axially moveable member of the surgical instrument of FIG. 1; the axially moveable member is shown at least partially shaped like an I-beam.

Referring briefly now to FIG. 5, a portion of the axially moveable member 140 is shown. The lever arm 128 of the handle 105 (FIG. 2) may be adapted to actuate the axially moveable member 140 which also functions as a jaw-closing mechanism. For example, the axially moveable member 140 may be urged distally as the lever arm 128 is pulled proximally along the path 129 via the shuttle 146, as shown in FIG. 2 and discussed above. The axially moveable member 140 may comprise one or several pieces, but in any event, may be movable or translatable with respect to the elongate shaft 108 and/or the jaws 120A, 120B. Also, in at least one embodiment, the axially moveable member 140 may be made of 17-4 precipitation hardened stainless steel. The distal end of axially moveable member 140 may comprise a flanged "I"-beam configured to slide within the channels 142A and 142B in jaws 120A and 120B. The axially moveable member 140 may slide within the channels 142A, 142B to open and close first jaw 120A and second jaw 120B. The distal end of the axially moveable member 140 may also comprise an upper flange or "c"-shaped portion 140A and a lower flange or "c"-shaped portion 140B. The flanges 140A and 140B respectively define inner cam surfaces 144A and 144B for engaging outward facing surfaces of first jaw 120A and second jaw 120B. The opening-closing of jaws 120A and 120B can apply very high compressive forces on tissue using cam mechanisms which may include movable "I-beam" axially moveable member 140 and the outward facing surfaces 162A, 162B of jaws 120A, 120B.

More specifically, referring now to FIGS. 3-5, collectively, the inner cam surfaces 144A and 144B of the distal end of axially moveable member 140 may be adapted to slidably engage the first outward-facing surface 162A and the second outward-facing surface 162B of the first jaw 120A and the second jaw 120B, respectively. The channel 142A within first jaw 120A and the channel 142B within the second jaw 120B may be sized and configured to accommodate the movement of the axially moveable member 140, which may comprise a tissue-cutting element 148, for example, comprising a sharp distal edge. FIG. 4, for example, shows the distal end of the axially moveable member advanced at least partially through channels 142A and 142B (FIG. 3). The advancement of the axially moveable member 140 may close the end effector 110 from the open configuration shown in FIG. 3. In the closed position shown by FIG. 4, the upper first jaw 120A and lower second jaw 120B define a gap or dimension D between the first energy delivery surface 175A and second energy delivery surface 175B of first jaw 120A and second jaw 120B, respectively. In various embodiments, dimension D can equal from about 0.0005" to about 0.040", for example, and in some embodiments, between about 0.001" to about 0.010", for example. Also, the edges of the first energy delivery surface 175A and the second energy delivery surface 175B may be rounded to prevent the dissection of tissue.

Figure 6:
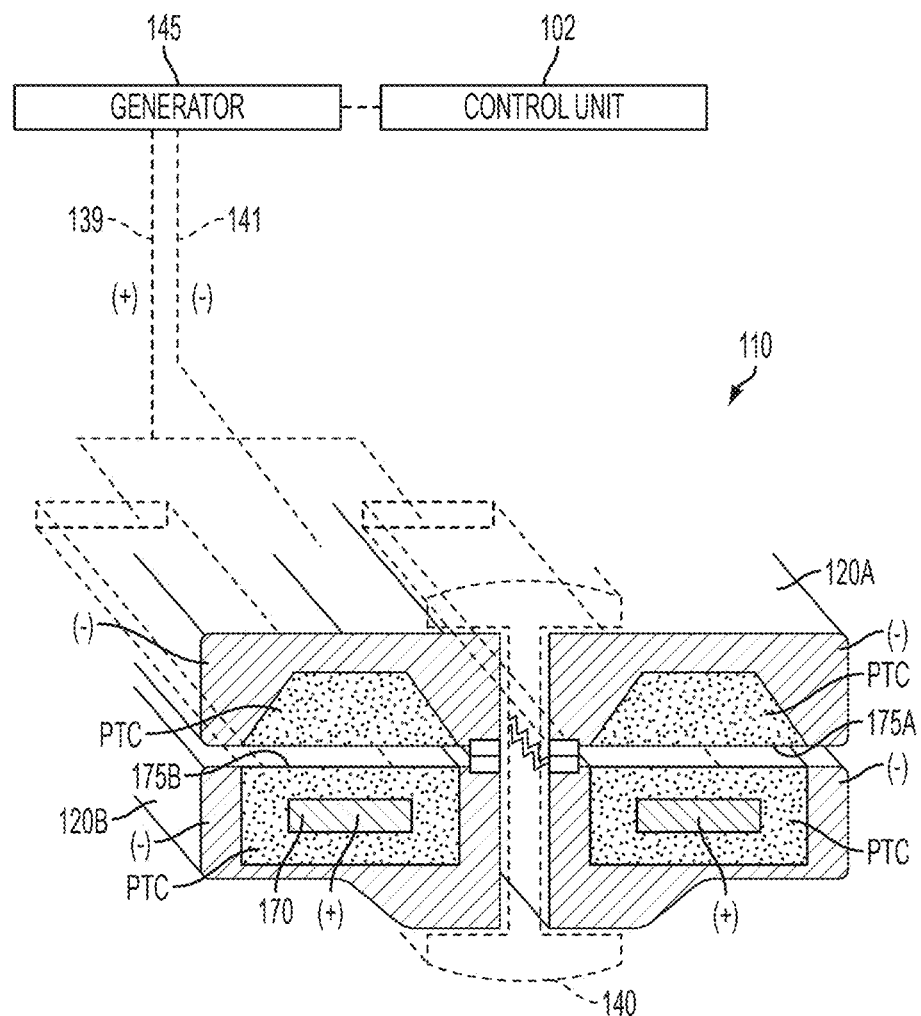
FIG. 6 is a sectional view of the end effector of FIG. 1

FIG. 6 is a sectional view of the end effector 110 in accordance with one non-limiting embodiment. In one embodiment, the engagement, or tissue-contacting, surface 175B of the lower jaw 120B is adapted to deliver energy to tissue, at least in part, through a conductive-resistive matrix, such as a variable resistive positive temperature coefficient (PTC) body, as discussed in more detail below. At least one of the upper and lower jaws 120A, 120B may carry at least one electrode 170 configured to deliver the energy from the generator 145 to the captured tissue. The engagement, or tissue-contacting, surface 175A of upper jaw 120A may carry a similar conductive-resistive matrix (i.e., a PTC material), or in some embodiments the surface may be a conductive electrode or an insulative layer, for example. Alternatively, the engagement surfaces of the jaws can carry any of the energy delivery components disclosed in U.S. Pat. No. 6,773,409, filed Sep. 19, 2001, entitled SURGICAL SYSTEM FOR APPLYING ULTRASONIC ENERGY TO TISSUE, the entire disclosure of which is incorporated herein by reference.

The first energy delivery surface 175A and the second energy delivery surface 175B may each be in electrical communication with the generator 145. The first energy delivery surface 175A and the second energy delivery surface 175B may be configured to contact tissue and deliver electrosurgical energy to captured tissue which are adapted to seal or weld the tissue. The control unit 102 regulates the electrical energy delivered by electrical generator 145 which in turn delivers electrosurgical energy to the first energy delivery surface 175A and the second energy delivery surface 175B. The energy delivery may be initiated by an activation button 124 (FIG. 2) operably engaged with the lever arm 128 and in electrical communication with the generator 145 via cable 152. In one embodiment, the electrosurgical instrument 101 may be energized by the generator 145 by way of a foot switch 144 (FIG. 1). When actuated, the foot switch 144 triggers the generator 145 to deliver electrical energy to the end effector 110, for example. The control unit 102 may regulate the power generated by the generator 145 during activation. Although the foot switch 144 may be suitable in many circumstances, other suitable types of switches can be used.

As mentioned above, the electrosurgical energy delivered by electrical generator 145 and regulated, or otherwise controlled, by the control unit 102 may comprise radio frequency (RF) energy, or other suitable forms of electrical energy. Further, the opposing first and second energy delivery surfaces 175A and 175B may carry variable resistive positive temperature coefficient (PTC) bodies that are in electrical communication with the generator 145 and the control unit 102. Additional details regarding electrosurgical end effectors, jaw closing mechanisms, and electrosurgical energy-delivery surfaces are described in the following U.S. patents and published patent applications: U.S. Pat. Nos. 7,087,054; 7,083,619; 7,070,597; 7,041,102; 7,011,657; 6,929,644; 6,926,716; 6,913,579; 6,905,497; 6,802,843; 6,770,072; 6,656,177; 6,533,784; and 6,500,176; and U.S. Pat. App. Pub. Nos. 2010/0036370 and 2009/0076506, all of which are incorporated herein in their entirety by reference and made a part of this specification.

In one embodiment, the generator 145 may be implemented as an electrosurgery unit (ESU) capable of supplying power sufficient to perform bipolar electrosurgery using radio frequency (RF) energy. In one embodiment, the ESU can be a bipolar ERBE ICC 350 sold by ERBE USA, Inc. of Marietta, Ga. In some embodiments, such as for bipolar electrosurgery applications, a surgical instrument having an active electrode and a return electrode can be utilized, wherein the active electrode and the return electrode can be positioned against, adjacent to and/or in electrical communication with, the tissue to be treated such that current can flow from the active electrode, through the positive temperature coefficient (PTC) bodies and to the return electrode through the tissue. Thus, in various embodiments, the electrosurgical system 100 may comprise a supply path and a return path, wherein the captured tissue being treated completes, or closes, the circuit. In one embodiment, the generator 145 may be a monopolar RF ESU and the electrosurgical instrument 101 may comprise a monopolar end effector 110 in which one or more active electrodes are integrated. For such a system, the generator 145 may require a return pad in intimate contact with the patient at a location remote from the operative site and/or other suitable return path. The return pad may be connected via a cable to the generator 145.

During operation of electrosurgical instrument 101, the user generally grasps tissue, supplies energy to the captured tissue to form a weld or a seal, and then drives a tissue-cutting element 148 at the distal end of the axially moveable member 140 through the captured tissue. According to various embodiments, the translation of the axial movement of the axially moveable member 140 may be paced, or otherwise controlled, to aid in driving the axially moveable member 140 at a suitable rate of travel. By controlling the rate of the travel, the likelihood that the captured tissue has been properly and functionally sealed prior to transection with the cutting element 148 is increased.

FIG. 7 is a schematic representation of an actuation assembly 200 in accordance with one non-limiting embodiment with some of the components thereof omitted for clarity. Additionally various components of the actuation assembly 200 have been expanded or altered in scale for convenience. The actuation assembly 200 may be used, for example, with instruments similar to electrosurgical instrument 101 in order to regulate or otherwise control the axial movement of an axially moveable member 240. The actuation assembly 200 may comprise an axially moveable member 240 which has at its distal end 242 a tissue-cutting element, such as a sharp distal edge 243, for example. The axially moveable member 240 may define a longitudinal axis 246. The axially moveable member 240 may also comprise a rack 244 configured to engage a drive gear 246. The drive gear 246 may be coupled to an internal shaft 248, which may define a longitudinal axis 250. In one embodiment the longitudinal axis 250 of the internal shaft 248 is substantially perpendicular to the longitudinal axis 246 of the axially moveable member 240. In some embodiments, a trigger gear 252 may also be coupled to the internal shaft 248. A portion of a trigger assembly 227 may comprise a rack 254 that is configured to engage the trigger gear 252. The actuation assembly 200 may also comprise a moveable locking member 256 this is selectably engagable with the internal shaft 248 or other component of the actuation assembly 200. The actuation assembly 200 may also comprise a spring, such as torsional spring 251, which distally drives the axially moveable member 240. One end of the torsional spring 251 may be coupled to the internal shaft 248 when the other end the torsional spring 251 may be attached to a portion of the actuation assembly 200 that remains stationary relative to the rotating internal shaft 248. Rotation of the internal shaft 248 winds the torsional spring 251 to generate potential energy which may be selectably transferred to the internal shaft 248, as described in more detail below.

Referring briefly to FIG. 8, a cross-sectional view of the engagement between the internal shaft 248 and the moveable locking member 256 is provided in accordance with one non-limiting embodiment. The internal shaft 248 may comprise a plurality of facets 258 positioned around its circumference. The facets 258 may longitudinally span the entire internal shaft 248, or may be positioned on a portion of the internal shaft 248, such as the portion proximate the moveable locking member 256. The movable locking member 256 may comprise a pawl 260 that engages the facets 258 of the internal shaft 248. The movable locking member 256 may be able to pivot in the direction indicated by arrow 262 to allow the internal shaft 248 to rotate in a first direction indicated by arrow 264. When the pawl 260 is engaged with a facet 258, the internal shaft 248 is prohibited from rotating in a second direction indicated by arrow 266. When the pawl 260 is disengaged from the facet 248, such as by movement of the pawl in the direction indicated by arrow 268, the internal shaft 248 may rotate in the directions indicated by arrow 266 and arrow 264.

Referring again to FIG. 7, the operation of the actuation assembly 200 allows for a controlled distal translation of the axially moveable member 240. In accordance with one embodiment, at the beginning of the operational stroke, the portion of a trigger assembly 227 comprising the rack 254 is moved in the direction indicated by arrow 270. As the rack 254 translates relative to the trigger gear 252, the trigger gear 252 rotates in the direction indicated by arrow 271. As the trigger gear 252 rotates, the internal shaft 248 rotates as well, which winds the torsional spring 251. The drive gear 246 also rotates in the direction indicated by arrow 271, which due to its engagement with the rack 244 of the axially moveable member 240, draws the axially moveable member 240 in the proximal direction indicated by arrow 272. The moveable locking member 256 keeps the internal shaft 248 from rotating in the direction indicated by arrow 274, despite the rotational force of the torsional spring 251 bearing on the internal shaft 248. When the activation button 124 (FIG. 2) is pressed, the movable locking member 256 may withdraw from engagement with the internal shaft 248. The coupling of the activation button 124 to the movable locking member 256 may be made using any suitable technique, such as a mechanical linkage, for example. In some embodiments, a tab on the trigger assembly 227 contacts the movable locking member 256 to move it from engagement with the internal shaft 228 once the torsional gear 251 is wound. Accordingly, any suitable technique may be used to disengage the movable locking member 256 from the internal shaft 248.

With the movable locking member 256 no longer locking the internal shaft 248, the internal shaft 248 rotates in the direction indicated by arrow 274 as the torsional spring 251 unwinds. Consequently, the drive gear 246 also rotates, and through its engagement with the rack 244, the axially moveable member 240 is driven in the distal direction indicated by arrow 276. The rate of travel of the axially moveable member 240 is generally dependent on the spring constant of the torsional spring 251, as opposed to the user's interaction with the trigger.

In various embodiments, the parameters of the components of the actuation assembly 200 may be altered to achieve the desired performance. For example, the size or strength of the torsional spring 251 may be changed. In one embodiment the gear ratio between the trigger gear 252 and the drive gear 246 may be a 1:1 ratio, while in other embodiments a different ratio is used. In some embodiments, as shown in FIG. 9, a single gear 280 may engage both the rack 254 of the trigger assembly 257 and the rack 244 of the axially moveable member 240. In some embodiments, a dashpot, such as damper 312 (FIG. 10), may be used to further control the translation of axially moveable member 240.

FIG. 10 is a simplified representation of an actuation assembly 300 in accordance with one non-limiting embodiment with some of the components thereof omitted for clarity. The actuation assembly 300 is associated with a handle 302 and an axially moveable member 306 extending distally from the handle. An end effector similar to the end effector 110 illustrated in FIG. 3 may be coupled to the distal end of an elongate shaft 304. The axially moveable member 306 may extend from the end effector and into the handle 302. As described in more detail below, a trigger 307 is operably coupled to the axially moveable member 306. In various embodiments, an advance spring 308 and a return spring 310 are each operably connected to the axially moveable member 306. The advance spring 308 and the return spring 310 may have different spring constants. In one embodiment, the advance spring 308 has a higher spring constant than the return spring 310. The actuation assembly 300 may further comprise a damper 312 configured to regulate (i.e., slow) the translation of the axially moveable member 306.

FIG. 10A provides a close-up view of the damper 312 in accordance with one non-limiting embodiment. The damper 312 comprises a barrel 314 and a plunger 316, wherein an outer surface of the plunger 316 is in sealing engagement with an inner surface of the barrel 314 to create a variable volume cavity 315. While the damper 312 is illustrated as having a barrel and plunger arrangement, any suitable damping device may be used, such as mechanical or hydraulics dashpots, for example. This disclosure is not limited to any particular damper arrangement. The plunger 316 may be coupled to, for example, the proximal end of the axially moveable member 306. The plunger may be movable between a first and second position within the barrel 314. The damper 312 may define a first port 318 having a first flow path and a second port 320 having a second flow path. In one embodiment, the damper 312 comprises a check valve 322 positioned in the second flow path. During operation, air may flow in both directions through the first flow path, while air may only exit the variable volume cavity 315 through the second flow path. As is to be appreciated, the size and number of ports in the barrel 314 may be varied to achieve the desired dampening.

Referring again to FIG. 10, the trigger 307 may pivot or rotate about a pivot 324 such that as the bottom trigger portion 307a is rotated in the direction indicated by arrow 326, the top trigger portion 307b is rotated in the direction indicated by arrow 328. The top trigger portion 307b may be coupled to an end of the advance spring 308. The other end of the advance spring 308 may be coupled to the axially moveable member 306, such as via a linkage 324. One end of the return spring 310 may also be coupled to the axially moveable member 306, such as via the linkage 324. The other end of the return spring 310 may be fixed to a mount 326. The advance spring 308 and the return spring 310 may exert biasing forces on the axially moveable member 306 in generally opposite longitudinal directions.

When the bottom trigger portion 307a is squeezed by a user, the top trigger portion 307b exerts a longitudinal force on both the advance spring 308 and the return spring 310 in the direction indicated by arrow 328. As described above, the squeezing of the trigger 307 may close the jaws of an associated end effector to capture tissue. As the user squeezes the trigger 307, both springs 308, 310 expand, the axially moveable member 306 distally translates in order to transect the captured tissue. The rate of travel of the axially moveable member 306 is regulated as a function of the spring constants of the springs 308, 310 and the dampening effects of the damper 312. Referring to FIG. 10A, as the plunger 316 distally translates in the barrel 314, the variable volume cavity 315 expands and a low pressure, below atmosphere, is generated. In order to reach equilibrium, ambient air enters the variable volume cavity 315 through the first port 318. In the illustrated embodiment, the check valve 322 prohibits air form entering the variable volume cavity 315 through the second port 320. As is to be appreciated, the damping coefficient of the damper 312 is a function of the rate of the ingress of the air through the first port 318. In some embodiments, the size of the first port 318 may be variable to provide a selectable damping coefficient. As the user continues to squeeze and rotate the bottom trigger portion 307a, the top trigger portion 307b will continue to exert a substantially linearly applied force on the springs 308, 310 which continue to expand. Since the advance spring 308 is stronger (i.e., has a higher spring constant) than the return spring 310, the axially moveable member 306, via the linkage 324, will be drawn distally in order to transect captured tissue. As the axially moveable member 306 is translated distally by the force applied through the advance spring 308, the return spring 310 expands between the linkage 324 and the mount 326.

When the user releases the trigger assembly 307, the expanded return spring 310 exerts a linear force on the linkage 324 to proximally translate axially moveable member 306. The proximal translation of the axially moveable member 306 will drive the plunger 316 (FIG. 10A) into the barrel 314, thus reducing the size of the variable volume chamber 315. Air will be expelled from the variable volume chamber 315 via both the first portion 318 and the second port 320. Thus, when the plunger 316 travels in the proximal direction, the damping coefficient of the damper 312 is less than when the plunger 316 travels distally.

The advance spring 308 and the return spring 310 may be any suitable types of biasing members, such as pistons, coil springs, rubber bands, and/or any other suitable elastic member, for example. In one embodiment, illustrated in FIG. 11, linear compression springs may be used as biasing members. FIG. 11 is a simplified representation of an actuation assembly 340 in accordance with one alternative non-limiting embodiment with some of the components thereof omitted for clarity. As illustrated, the actuation assembly 340 may comprise a return spring 342 and an advance spring 344. The overall operation of the actuation assembly 340 may be generally similar to the operation of the actuation assembly 300 illustrated in FIG. 10, with the exchange of linear compression springs for linear expansion springs. Accordingly, as the lower trigger portion 307a is rotated in the direction indicated by arrow 326, the upper trigger portion 307b compresses the springs 342, 344 similar to the above. The damper 312 serves to regulate the rate of distal and proximal translation of the axially moveable member 306.

According to various embodiments, the pacing of the axial movement of the axially moveable member may driven by an electric motor or any other type of suitable linearly actuating device, such as an electroactive polymer (EAP) actuator, for example. FIGS. 12-15 illustrate a representation of an electrosurgical instrument 400 comprising a linear actuator 402 in accordance with one non-limiting embodiment. For clarity, various components have been omitted. The electrosurgical instrument 400 may comprise a proximal handle 405, a distal working end or end effector 410 and an introducer or elongate shaft 408 disposed in-between. An axially moveable member 440 may couple the end effector 410 and a trigger assembly 407. The end effector 410 may comprise a set of openable-closeable jaws with straight or curved jaws, similar to the end effector 110 illustrated in FIG. 3, for example. In one embodiment, the linear actuator 402 comprises a lead screw 420 and an electric motor 422 coupled to the lead screw 420. The electric motor 422 may be coupled to a power 121 supply 425 via cabling 426. As is to be appreciated, the power supply 425 may be any suitable power source and may be a separate unit (as illustrated), or carried on-board the electrosurgical instrument 400. In some embodiments, other techniques may be used to impart linear motion to the axially moveable member 440. For example, similar to FIG. 9, the axially moveable member 440 may comprise a rack and the motor 422 may rotate a drive gear operably engaged to the rack.

A nut assembly 424 may be slideably engaged to the axially moveable member 440 and the lead screw 420. The nut assembly 424 may interface the axially moveable member 440 at a clearance 429. The clearance 429 may be, for example, a portion of the axially moveable member 440 having a reduced diameter. Either end of clearance 429 may have a proximal stop 428 and a distal stop 430. The proximal and distal stops 428, 430 may each be a lip, as illustrated. It is noted that the clearance 429 illustrated in FIGS. 12-15 has been expanded for clarity and is not necessarily drawn to any particular scale. As discussed in more detail below, the clearance 429 generally allows for the opening and closing of the jaws of the end effector 410, while prohibited the cutting of tissue until the tissue has been properly sealed.

The trigger assembly 407 may be operatively engaged with axially moveable member 440 at a trigger interface 432. The trigger interface 432 may include a distal sensor 434 and a proximal sensor 436. The trigger interface 432 may also include a distal trigger stop 433 and a proximal trigger stop 435. The electrosurgical instrument 400 may also comprise a button 438. When the button 438 is engaged, electrical energy (i.e., RF energy) may be supplied to captured tissue via the end effector 410.

Figure 12:
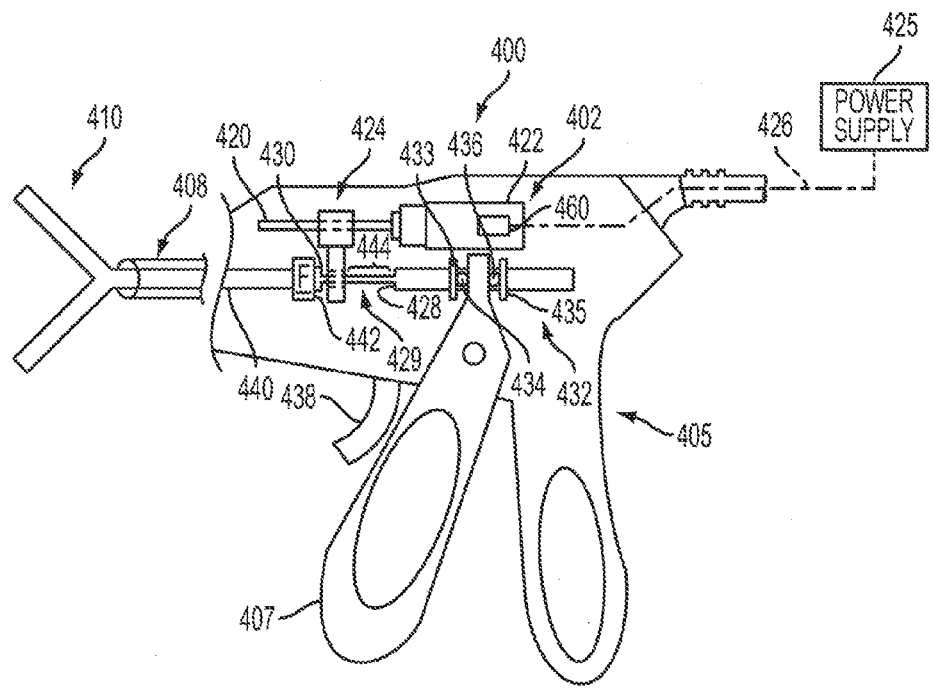
Figure 13:
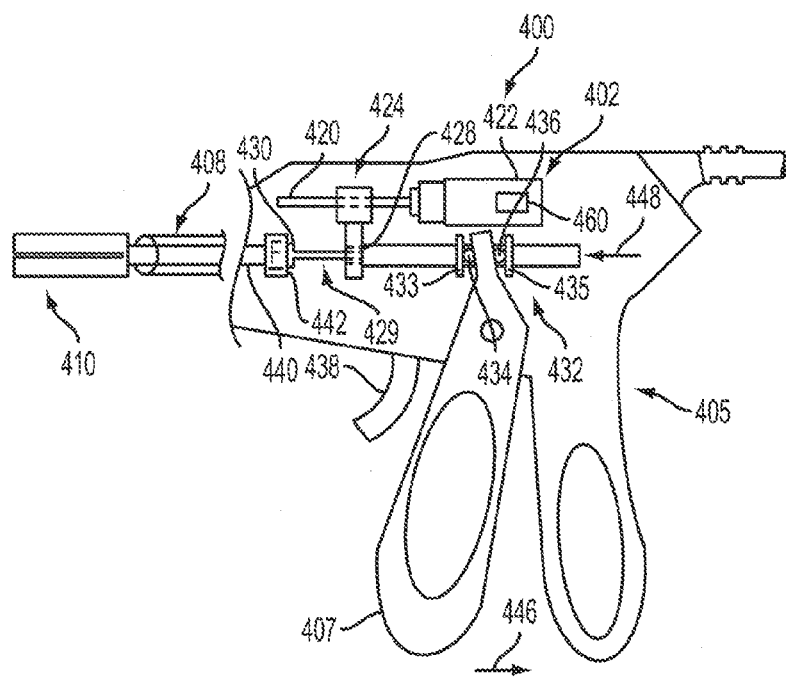

With reference to FIGS. 12-15, the operation of the electrosurgical instrument 400 in accordance with one non-limiting embodiment will be described. In FIG. 12, the jaws of the end effector 410 are in an open position allowing tissue to be captured therebetween. A gap 444 is present between the nut assembly 424 and the proximal stop 428. In FIG. 13, the trigger assembly 407 has been rotated (i.e., squeezed) in the direction indicated by arrow 446. As the trigger assembly 407 rotates it engages the distal trigger stop 433 which is coupled to the axially moveable member 440. As the axially moveable member 440 moves in the direction indicated by arrow 448, the jaws of the end effector 410 are closed, similar to the end effector 110 illustrated in FIG. 4. The progression of the axially moveable member 440 in the direction indicated by arrow 448 is impeded when the proximal stop 428 engages the nut assembly 424. Accordingly, at this stage in the operational stroke, the distance of travel of axially moveable member 440 is generally limited to the length of the gap 444 (FIG. 12). In one embodiment, this distance is long enough to cause the jaws of the end effector 410 to clamp tissue, while keeping a cutting element at the distal end of the axially moveable member 440 from contacting the captured tissue. Generally, by providing the clearance 429 on the axially moveable member 440, a relatively small amount of trigger assembly manipulation may be performed by the user to open and close the jaws of the end effector without distally driving the cutting element into the tissue. The cutting element is only driven through the tissue when the linear actuator 402 is activated. As is to be appreciated, the clearance 429 may sized based on the particular arrangement of the electrosurgical instrument 400. For example, in one embodiment, the clearance 429 may be less than about 0.5 inches in length as measured between the proximal stop 428 and a distal stop 430. In one embodiment, the clearance 429 may be less than about 0.2 inches, for example, in length as measured between the proximal stop 428 and a distal stop 430. As is to be appreciated, the size of the clearance 429 for any electrosurgical instrument 400 will at least partially depend on the relative size of the nut assembly 424 since a gap 444 is required between the nut assembly 424 and the distal stop 430.

Figure 14:
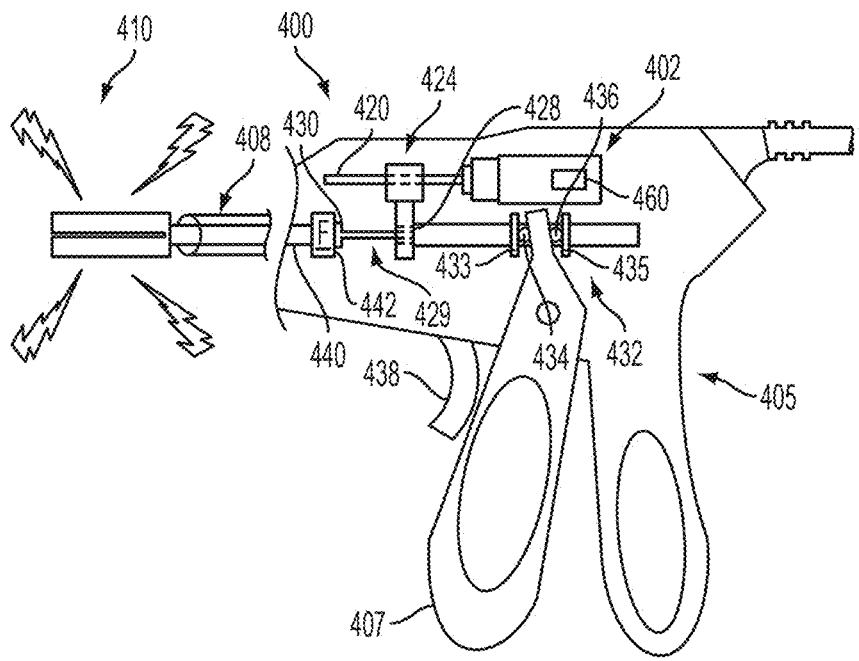
Figure 15:
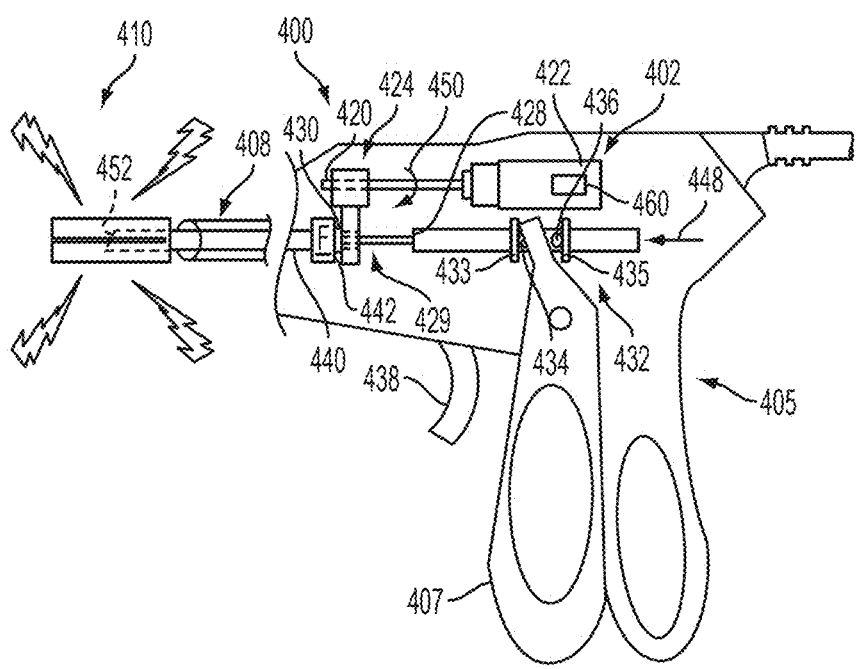

Referring now to FIG. 14, when the button 438 is activated by the user, energy flows through electrodes in the end effector 410 to energize the captured tissue (not illustrated). When the button 438 is activated and the trigger 407 is squeezed, the motor 422 of the linear actuator 402 rotates lead screw 420 in the direction indicated by arrow 450 (FIG. 15). In one embodiment, the motor 422 will only be activated when both the button 438 is activated to deliver the RF energy to the tissue and the trigger 407 is squeezed. By requiring the user to complete both actions before activating the linear actuator 402, the possibility of a "cold cut" (e.g., cutting the tissue before it has been welded) is greatly reduced or eliminated. The squeezing of the trigger 407 may be sensed by the distal sensor 434. The distal sensor 434 may be, for example, a pressure sensor that supplies a signal to an associated controller. As the lead screw 420 rotates, the nut assembly 424 travels in the direction indicated by arrow 448, owing to the operative engagement of threads on the lead screw 420 and a threaded aperture in the nut assembly 424. As the nut assembly 424 travels along the lead screw 420, the nut assembly 424 will engage the axially moveable member 440 at the distal stop 430. The nut assembly 424 will then push the axially moveable member 440 in the distal direction as the user continues to squeeze the trigger 407 and lead screw 420 continues to rotate. A cutting element 452 positioned on the distal end of the axially moveable member 440 progresses through and transects the captured tissue. When the user opens the trigger 407, the trigger 407 can move toward and activate the proximal sensor 436. Activation of the proximal sensor 436 will cause the motor 422 to rotate the lead screw 420 in the opposite direction, and owing to the threaded engagement between the lead screw 420 and the nut assembly 424, the nut assembly 424 will translate through the gap 444 (FIG. 12) and engage the axially moveable member 440 at the proximal stop 428. The nut assembly 424 will then push the axially moveable member 440 in the proximal direction as the user continues to open the trigger 407 and lead screw 420 continues to rotate. In one embodiment, the motor 422 may rotate the lead screw 420 faster during the proximal progression of the axially moveable member 440 as compared to the distal progression. As is to be appreciated, a controller 502 (FIG. 16) may be used to receive the inputs from various components of the electrosurgical instrument 440, such as the button 438 and the sensors 434, 436, and selectively supply energy to the motor 422.

The speed of the motor 422 may be changed based on any particular application. In one embodiment, at least one of the proximal sensor 436 and the distal sensor 434 measures the amount of force exerted by the user during the trigger actuation. In one embodiment, the displacement of the trigger is monitored. In any event, as the force exerted by the user increases (or the displacement of the trigger increases), the speed of the motor 422 is also increased. Therefore, for applications involving large amounts of captured tissue, for example, the user can selectively increase or decrease the speed of the motor through manipulation of the trigger.

The maximum rate of travel of the axially moveable member 440 is determined by the linear actuator 402. In various embodiments, the rate of travel of the axially moveable member 440 may be adjustable by the user. In some embodiments, the electrosurgical instrument 400 may comprise a force transducer 442. The force transducer 442 may be any type of load cell suitable to produce a signal indicative of the force. The force transducer 442 may supply information to the controller indicative to characteristics of the captured tissue. For example, thicker tissue will generally require more time to properly seal and will provide more resistance to the axially moveable member 440 as it passes through the tissue. Comparatively, thinner tissue will generally require less time to properly seal and will provide less resistance to the axially moveable member 440 as it passes through the tissue. Information from the force transducer 442 may be supplied to the controller 502 (FIG. 16) and the speed of the motor 422 may be adjusted to compensate for the tissue characteristics. Accordingly, the rotational speed of the lead screw 420 may be reduced when cutting thicker tissue in order to lengthen the amount of time the captured tissue is exposed to the RF energy. The rotational speed of the lead screw 420 may be increased when cutting thinner tissue to shorten the amount of time the captured tissue is exposed to the RF energy and reduce the likelihood of charring or excess heating. In any event, the use of the linear actuator 402 helps to ensure a steady and regulated translation of the axially moveable member through the tissue, even with end effectors having a relatively long jaw length.

In various embodiments, the electrosurgical instrument 440 may have an encoder 460 associated with the linear actuator 402. The encoder 460 may supply information to an associated controller to aid in the cutting of the captured tissue, such as speed data. The encoder 460 may be any type of suitable encoder, such as a rotary encoder to monitor the rotation of the lead screw 420. The linear displacement of the axially moveable member 440 may then be determined as a function of the threaded coupling between the nut assembly 424 to the lead screw 420.

FIG. 16 is a block diagram of a control system 500 of an electrosurgical instrument in accordance with one non-limiting embodiment. A controller 502 receives various inputs from the components, such as an encoder 560, a force transducer 542, a button 538, a distal sensor 534, and a proximal sensor 536. When an activation signal is received from the button 538, the controller 502 may send a signal to an RF source 504 which, in turn, provides RF energy to an electrode 506. When the controller 502 receives an activation signal from both the button 538 and the distal sensor 534, the controller 502 may supply current to the motor 522. As described above, information received from the encoder 560 and the force transducer 542 may provide a feedback loop to aid in the motor control. For example, the encoder 560 may indicate that the axially moveable member has reached the distal end of its stroke indicating to the controller 502 to cease supplying current to the motor 522. When the proximal sensor 536 supplies a signal to the controller 502, the controller 502 may rotate the motor 522 in an opposite direction. The encoder 560 may indicate that the axially moveable member has reached the proximal of its stroke indicating to the controller 502 to cease supplying current to the motor 522.

FIG. 17 is a flow chart 580 of the operation of an electrosurgical instrument having a linear actuator in accordance with one non-limiting embodiment. At 582, the instrument is in a standby mode. In standby mode, the jaws are in the open position and ready to engage tissue. At 584, a main trigger, such as trigger 407 (FIG. 14) is moved from a first position to a second position in order to capture tissue between the jaws. At 586, a button, such as button 538, for example, or any other type of triggering or activation device, is activated to supply electrical energy to the captured tissue. At 588, while the button is activated, the main trigger is moved from the second position to a third position to activate a linear actuator and cut the captured tissue. At 590, an axially moveable member is distally advanced using a linear actuator. At 592, the main trigger is moved from the third position back to the first position and the linear actuator is activated to move the axially moveable member in the proximal direction to open the jaws of the end effector.

In various embodiments, a dashpot may be coupled to a trigger-actuated axially moveable member in order to regulate the rate of travel of axially moveable member. FIGS. 18-21 illustrate an electrosurgical instrument 600 with various components removed, or otherwise simplified, for clarity. The electrosurgical instrument 600 has a handle 602 and an elongate shaft 604 extending distally from the handle. An end effector 610 similar to the end effector 110 illustrated in FIG. 3 may be coupled to the distal end of the elongate shaft 604. An axially moveable member 606 may extend from the distal end of the elongate shaft 604 into the handle 602. A trigger 607 is coupled to the axially moveable member 606. The electrosurgical instrument 600 may further comprise a damper 612 (shown in cross-section) configured to regulate the translation of the axially moveable member 606. Generally, movement of the trigger 607 corresponds to movement of the axially moveable member 606 in the distal and proximal direction due to a pivot 616 and a linkage 614 connecting the trigger 607 to the axially moveable member 606.

The damper 612 may be associated with the axially moveable member 606 such that it controls the speed of the axially moveable member 606 during the operational stroke of the electrosurgical instrument 600. FIG. 18A is an enlarged cross-sectional view of the damper 612 in accordance with one non-limiting embodiment. In one embodiment, the damper 612 comprises a barrel 620 and a plunger 622, wherein an outer diameter of the plunger 622 is in sealing engagement with an inner diameter of the barrel 620. As is to be appreciated, an o-ring 640, or other type of sealing device may be positioned around the periphery of the plunger 622 to aid in creating a seal with the barrel 620. Furthermore, as illustrated, the plunger 622 may be coupled to the axially moveable member 606. The plunger 622 may be formed unitary with the axially moveable member 606 or otherwise coupled thereto. The damper 612 may also have a spring 624, or other biasing element, to bias the axially moveable member 606 in the proximal direction. In the illustrated embodiment, a spring 624 is positioned intermediate the plunger 622 and a distal end 626 of the damper 612.

Still referring to FIG. 18A, the distal end 626 may have at least one inlet orifice 628 and at least one outlet orifice 630. The inlet orifice 628 may have a check valve 632 which permits air to flow into the barrel 620 while restricting air to flow out of the barrel 620 through that orifice. The check valve 632 may pivot in the direction indicated by arrow 633. In one embodiment, the outlet orifice 630 is an open aperture allowing free flow of air (or other fluid) in and out of the barrel 620. The inlet orifice 628 and the outlet orifice 630 may have different cross sectional areas, with the outlet orifice 630 being smaller than the inlet orifice 630. In some embodiments, the area of the outlet orifice 630 is variable. The distal end 626 may also have a center orifice 634 which is sized to accommodate the axially moveable member 606. In various embodiments, a o-ring 636, or other sealing device, may be used to maintain a seal between the distal end 626 of the damper 612 and the axially moveable member 606. The barrel 620 and the distal surface of the plunger 622 define a variable volume cavity 642. The volume of the variable volume cavity 642 decreases as the plunger 622 is distally translated and increases in volume as the plunger 622 is proximally translated.

Figure 19:
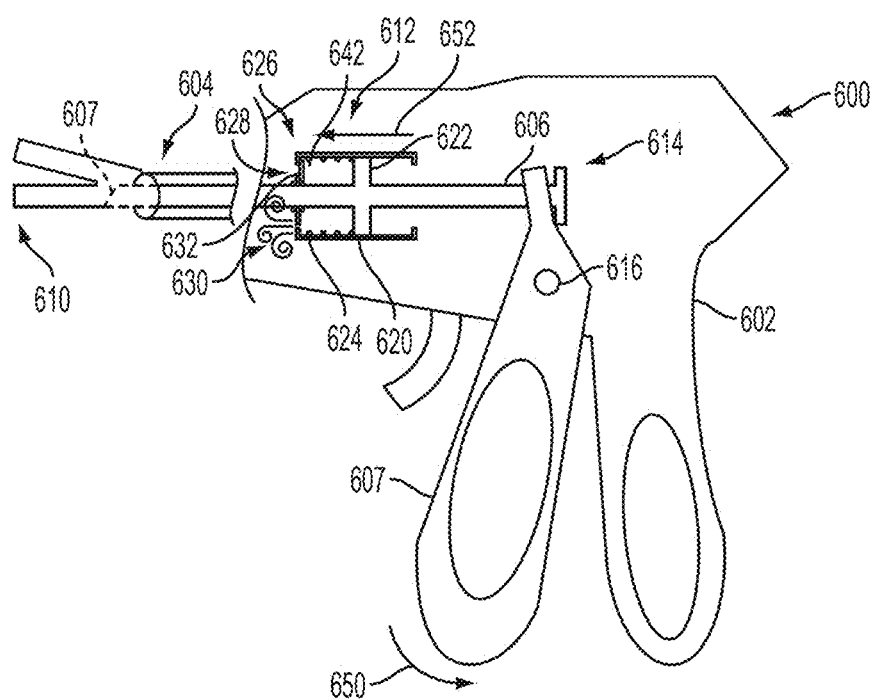

Referring again to FIGS. 18-21, the operation of the electrosurgical instrument 600 in accordance with one non-limiting embodiment will now be described. In FIG. 18 the electrosurgical instrument 600 is configured to begin the operational stroke. The plunger 622 is positioned at the proximal end of the barrel 620 and the jaws of the end effector 610 are in an open position. FIG. 19 illustrates the electrosurgical instrument 600 as the trigger 607 is rotated (or squeezed) in the direction indicated by arrow 650. As the trigger 607 is rotated, the plunger 622 is translated in the direction indicated by arrow 652. The biasing force of the spring 624 is overcome and the variable volume cavity 642 is reduced in the volume. Air is expelled from the variable volume cavity via the outlet port 630 (FIG. 18A). Due to the operation of the check valve 632, air is not expelled, or substantially expelled, through the inlet port 628 (FIG. 18A). Thus, when the user actuates the trigger 607, the speed of the axially moveable member 606 is controlled by the cross sectional area of the outlet port 630. The expelling of air (or other fluid) from the variable volume cavity 642 acts as a resistive force to the rotation of the trigger 607 to slow the operational stroke of the axially moveable member 606. As the plunger 622 translates within the barrel 620 the axially moveable member 606 is distally translated and the end effector 610 closes its jaws to capture and transect tissue therebetween with a cutting element 607. As the plunger 622 distally translates within the barrel 620, the spring 624 is compressed to create a stored energy which biases the end effector 610 open at the end of the cycle.

Figure 20:
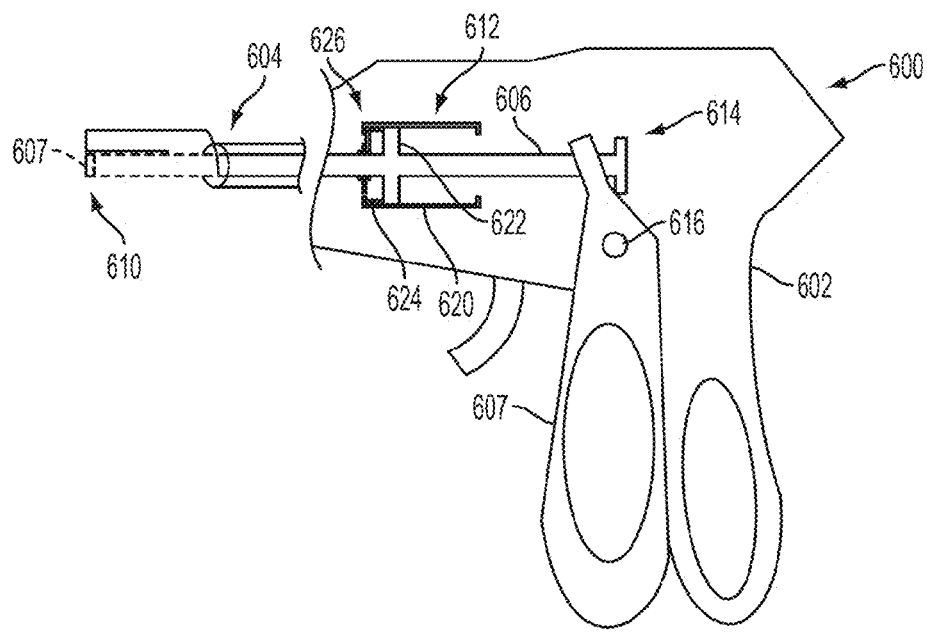
Figure 21:
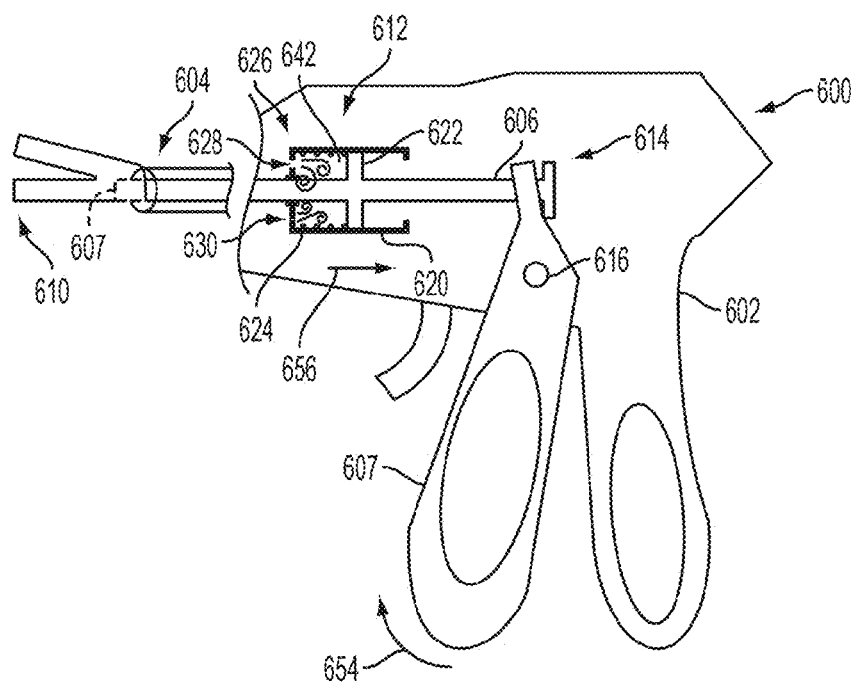

As shown in FIG. 20, the axially moveable member 606 may continue to distally translate to move the plunger 622 toward the distal end 626 of the barrel 620. The spring 624 is compressed between the plunger 622 and the distal end 626 of the barrel 620. As is to be appreciated, energy may be introduced into the captured tissue to sufficiently weld the tissue prior to and during the operational stroke. As illustrated in FIG. 21, rotation of the trigger 607 in the direction indicated by arrow 654 translates the plunger 622 in the direction indicated by arrow 656 (e.g., proximally). As the plunger 622 is translated proximally, the volume of the variable volume cavity 642 is increased. The increase in volume generates a low pressure which draws air (or other fluid) into the variable volume cavity 642. Due to the operation of the check valve 632 (FIG. 18A), air is permitted to enter the variable volume cavity 642 through both the inlet port 628 and the outlet port 630. Therefore, the plunger 622 may translate proximally with less resistance as compared to distal translation.

FIGS. 22-25 illustrates the electrosurgical instrument 600 with a damper 660 having two check valves. The spring 624 is positioned external to the damper 660 such that it provides a biasing force to the trigger 607. FIG. 22A is an enlarged cross-sectional view of the damper 660. The damper 660 comprises a barrel 662 which receives the plunger 622. A variable volume cavity 664 is formed between the plunger 622 and the distal end 666 of the barrel 662. The damper 660 further has a first orifice 668 and a second orifice 670 positioned in the distal end 666 of the barrel 662. A first check valve 672 is positioned proximate the first orifice 668 and a second check valve 674 is positioned proximate the second orifice 670. The first check valve 672 defines a first outlet 676 and the second check valve 674 defines a second outlet 678. When the plunger 622 is translated in the distal direction, air is forced from the variable volume cavity 664 through the first outlet 676 and the second outlet 678. When the plunger 622 is translated in the proximal direction, the check valves 672, 674 open and air is drawn into the variable volume cavity 664 through the first orifice 668 and the second orifice 670. The total cross-sectional area of the first and second orifices 668, 670 may be greater than the total cross-sectional area of the first and second outlets 676, 678.

A damper may be coupled to the trigger and/or axially moveable member of an electrosurgical instrument using any suitable configuration. FIG. 26 illustrates an embodiment of a damper 680 that is coupled to a tab 682 of the trigger 607 via a shaft 686. The damper 680 comprises a barrel 688 that may have an inlet port 681 and outlet port 683 arrangement similar to the configuration illustrated in FIG. 18A. As is to be appreciated, however, any suitable configuration of orifices may be used. The shaft 686 is coupled to a plunger 684. In some embodiments, the shaft 686 and/or the plunger 684 may be integral with the trigger 607. Rotation of the trigger 607 in the direction indicated by arrow 650 drives the plunger 684 into the barrel 688. As the plunger 684 drives into the barrel 688, the volume of a variable volume cavity 690 inside the barrel 688 is reduced. Fluid inside the variable volume cavity 690 is expelled through outlet port 683. Thus, the damper 680 regulates the translation of axially moveable member 606 by providing resistance to the trigger 607 when the user attempts to squeeze the trigger too fast. FIG. 26A is an illustration of the damper 680 in accordance with another non-limiting embodiment. A sealing member 694 (e.g., an o-ring) may establish a seal between the shaft 686 and an orifice 695 of the barrel 688. The barrel 688 may be filled with a highly viscous fluid 692. The plunger 684 may separate the barrel 688 into a first cavity 691 and a second cavity 693. As the plunger 684 is translated within the barrel 688, one of the cavities increases in volume while the other cavity decreases in volume. The highly viscous fluid 692 may flow between the two cavities via a gap 696 between the plunger 684 and the inner wall of the barrel 688. In some embodiments, the plunger 684 may have orifices that fluidly couple the first cavity 691 to the second cavity 693. During the operational stroke, the plunger 684 is translated in the barrel 688 and the highly viscous fluid 692 generally opposes the motion of the plunger 684 to ultimately regulate the translation of the axially moveable member.

As is to be appreciated, any type of damper may be used. As illustrated in FIG. 27, in some embodiments, a rotary damper 700 may be used to regulate the movement of an axially moveable member 702. The rotary damper 700 may comprise a sealed volume 704. In one embodiment, the sealed volume 704 is a cavity formed within a trigger 706. The trigger may be rotatable about a pivot 708. At least one fin 710 may be fixed with respect to the trigger 706. As illustrated, the fins 710 may radiate from the pivot 708. While two fins 710 are illustrated in FIG. 27, it is to be appreciated that any number of fins 710 may be used. Furthermore, the fins 710 may be straight, curved, or a combination of straight and curved sections. In some embodiments, the fins may be attached to inner surface of the 712 of the sealed volume 704 and extend toward the pivot 708. In any event, the sealed volume 704 may be filled with a fluid 714, such as a highly viscous silicone fluid, for example. Protrusions 713 may extend into the sealed volume 704 and move relative with respect to the fins 710 during rotation of the trigger 706. The protrusions 713 may be any size or shape. As the trigger 706 is rotated in the direction indicated by arrow 716, the interaction of the viscous fluid 714, the fins 710, and the protrusions 713 will provide a resistive force to slow the rotation of the trigger. FIG. 27A is a cross-sectional view of the damper 700 taken along line 27A-27A. The damper 700 is rotatable about a central axis 701. While the fins 710 are illustrated in FIG. 27A as being generally rectangular, it is to be appreciated that any suitable shape may be used. Furthermore, the fins 710 and/or protrusions 713 may be solid, as illustrated, or may be discontinuous (e.g., vented or perforated) to achieve the desired fluid flow during rotation of the damper 700.

Referring again to FIG. 27, a return spring 720, or other biasing element, may be coupled to the trigger 706 and the handle 722 in order to urge the trigger 706 to its starting position after it is moved in the direction indicated by arrow 724. During an operational stroke, the amount of counter force the trigger 706 experiences, (e.g., the dampening effect) will depend at least partially on the size of a gap 718 between the pivot 708 and protrusions 713. As with the other dampers described herein, the faster the trigger 706 is rotated, the higher the resistive force supplied by the rotary damper 700 will be. In other words, the resistive force may be proportional to the velocity of the trigger actuation. If the user actuates the trigger 706 in a slow and controlled manner, the rotary damper 700 will provide relatively little resistive force. If, however, the user actuates the trigger 706 aggressively, the rotary damper 700 will provide a higher resistive force to slow the trigger actuation 716.

As is to be appreciated, any suitable type of damper may be used to regulate the stroke of the trigger. For example, in some embodiments, the damper may comprise a magnetorheological fluid damper or a solenoid having a variable resistance.

In some embodiments, other techniques may be used to regulate the translation of the axially moveable member. FIG. 28 illustrates an electrosurgical instrument 800 incorporating an electromagnetic brake assembly 802 in accordance with one non-limiting embodiment. The electrosurgical instrument 800 may have an end effector (not illustrated) similar to the end effector 110 illustrated in FIG. 3 coupled to the distal end of an elongate shaft 804. An axially moveable member 806 may extend from the distal end of the elongate shaft 804 into the handle 808. A trigger 810 is coupled to the axially moveable member 806. In one embodiment, the trigger 810 comprises a toothed section 812 and the axially moveable member 806 comprises a rack 814. The toothed section 812 of the trigger 810 is engaged to the rack 814 such that rotational movement of the trigger 810 about a pivot 816 is transferred into distal and proximal linear movement of the axially moveable member 806. The rack 814 may have two general sections 818, 820. During an operational stroke, the toothed section 812 first engages a first section 818 and the end effector captures and clamps tissue between two jaws, for example. As a second section 820 of the rack 814 engages the toothed section 812, a cutting element may be driven through the captured tissue as described in greater detail below. The electromagnetic brake assembly 802 may regulate the stroke of the moveable cutting element 806 when the second section 820 of the rack 814 is engaged to the toothed section 812. By regulating this portion of the stroke, the likelihood of advancing the moveable cutting element 806 too quickly (e.g., before the captured tissue has been sufficiently welded) is reduced. Some embodiments may comprise other implementations of electrically actuated brake assemblies. For example, the brake assembly may comprise an element that responds to external electrical stimulation by displaying a significant shape or size displacement, such as an electroactive polymer (EAP), for example. In some embodiments, the brake assembly may comprise a other components, such as a solenoid, a magnetorheological fluid damper, a reed relay, and/or a stepper motor, for example. All such embodiments are intended to be included in this disclosure.

FIG. 29 is an illustration of the electromagnetic brake assembly 802 in accordance with one non-limiting embodiment. The electromagnetic brake assembly 802 may comprise a collar 830. When a controller 832 supplies current from a power source 834 a magnetic field around the collar 830 is generated. The axially moveable member 806 is positioned proximate the collar 830 and is has a ferrous component, for example, that is attracted to or repulsed by magnetic fields. The controller 832 may receive information via an input 836 to determine if a magnetic field should be generated and/or the strength of the magnetic field. The input 836 may be an indication of tissue temperature, tissue impedance, or time, for example. In one embodiment, if the captured tissue has not reached suitable temperature to sufficiently weld tissue, the electromagnetic brake 802 may be activated. Specifically, a magnetic field may be generated to attract the axially moveable member 806 to the collar 830. When the axially moveable member 806 is attracted to the collar 830, the distal progression of the axially moveable member 806 is halted or slowed depending on the intensity of the magnetic field generated. Once the temperature of the captured tissue has reached a sufficient level, the magnetic field of the collar 830 may be reduced or eliminated to allow the axially moveable member 806 to continue its distal translation.

As is to be appreciated, while the collar 830 is illustrated as having a ringed cross-sectional shape, any suitable cross-sectional shape may be used. For example, the collar 830 may have a rectangular, triangular, trapezoidal, or other closed-form shape. In some embodiments, multiple collars 830 having the same or different shapes may be used. This disclosure is not limited to any particular size, shape, or arrangement of the collar(s) 830. FIG. 30 is an illustration of an electromagnetic brake assembly 840 in accordance with another non-limiting embodiment. In this embodiment, a brake element 842 is positioned proximate the trigger 810. When the brake element 842 is energized by the controller 832 a magnetic field is generated which attracts the trigger 810. Similar to the collar 830 illustrated in FIG. 29, the brake element 842 may serve to regulate to movement of axially moveable member 806 by selectively engaging the trigger 810. When the trigger 810 is attracted to the brake element 842, the distal progression of the axially moveable member 806 is halted or slowed depending on the intensity of the magnetic field generated.

FIG. 31 is a partial cut-away view of an electrosurgical instrument 900 having an electromagnetic brake assembly in accordance with one non-limiting embodiment. A partial cross-section is provided to illustrate an electromagnetic brake assembly 902. For the sake of clarity, various components have been omitted from the electrosurgical instrument 900. The electrosurgical instrument 900 may have an end effector (not illustrated) similar to the end effector 110 illustrated in FIG. 3 coupled to the distal end of an elongate shaft 904. An axially moveable member 906 may extend from the distal end of the elongate shaft 904 into the handle 908. A trigger 910 is coupled to the axially moveable member 906. In one embodiment, the trigger 910 comprises a pivot 912. A surface 914 of the trigger 910 may comprise a series of trigger ridges 916. In one embodiment, the trigger ridges 916 radiate outward from the pivot 912. The trigger ridges 916 are dimensioned to engage a brake pad 918. FIG. 32 illustrates an enlarged view of the brake pad 918. The brake pad 918 may comprise pad ridges 920 with troughs 922 positioned intermediate adjacent pad ridges 920. The troughs 922 are dimensioned to receive the trigger ridges 916.

Referring again to FIG. 31, the brake pad 918 may be coupled to an electromagnetic solenoid 924, or other component capable of selectably translating the brake pad 918 between a disengaged position and an engaged position (e.g., an electroactive polymer actuator). The solenoid 924 may be energized by a controller 832 (FIG. 30). When the solenoid 924 is activated, the brake pad 918 is driven toward the trigger ridges 916 such that they engage with the pad ridges 920. When the ridges 916, 920 are engaged, the trigger 910 is locked and may not be further rotated by the user. When the solenoid 924 is de-activated, the brake pad 918 is retracted and the trigger ridges 916 disengage from the pad ridges 920 to allow the trigger 910 to continue its rotation. During operation, the user may simply apply pressure to the trigger 910 and the electromagnetic brake assembly 902 will continually lock and un-lock the trigger 910 in order to regulate the stroke. Similar to the embodiments illustrated in FIGS. 29 and 30, a controller may use information from various inputs to determine if the trigger 910 should be locked or unlocked. As is to be appreciated, the trigger ridges 916 and the brake pad 918 may be made from any suitable material or polymer, such as a thermal set rigid plastic, for example. In some embodiments, the polymer is a nylon or rubber polymer, for example. In other embodiments, the trigger ridges 916 and the brake pad 918 are made from a metal alloy, such as medical grade stainless steel, for example.

FIGS. 33A and 33B, illustrate the electromagnetic brake assembly 902 in various stages of operation. The brake pad 918 is coupled to a pad housing 926 that is coupled to the solenoid 924. While the ridges 916, 920 are illustrated in a saw tooth configuration, it is appreciated that any suitable type of ridge shapes may be implemented. As illustrated, the operation of the solenoid may be controlled by a controller 932. The controller 932 may receive information from a sensor 934. The information may be, for example, tissue temperature information or tissue impedance information. In FIG. 33A, the brake pad 918 is separated (i.e., disengaged) from the trigger ridges 916 of the trigger 910. In this position, the trigger 910 may rotate with respect to the brake pad 918. In FIG. 33B, the solenoid 924 has translated the brake pad 918 in the direction indicated by arrow 930. In this position, the brake pad 918 is engaged to the trigger ridges 916 of the trigger 910 to inhibit the rotation of the trigger 910 with respect to the brake pad 918. This position may be maintained until any number of conditions are satisfied, such as a tissue temperature condition or a time-based condition. In at least one embodiment, the brake pad 918 can lock the trigger 910 in position until the temperature and/or impedance of the tissue being treated has exceeded a certain temperature and/or impedance. In such an embodiment, the advancement of movable member 906, and cutting member associated therewith, can be delayed until a sufficient quantity of energy has been supplied to the tissue, as indicated by the sensed temperature and/or impedance. In such circumstances, the tissue may not be incised until the tissue has received a minimum amount of energy. In some embodiments, the brake can be operated on a time delay, i.e., an amount of time between the initial application of energy to the tissue and the release of the brake.

FIG. 34 is a partial cut-away view of an electrosurgical instrument having an electromagnetic brake assembly 902 in accordance with one non-limiting embodiment. As illustrated, the trigger ridges 916 are positioned around a periphery of the trigger 910. The brake pad 918 is positioned to engage the trigger ridges 916 when the brake pad 918 is moved toward the trigger 910 by the solenoid 924. The brake pad 918 may have a curved portion 920 to mate with the periphery of the trigger 910. As is to be appreciated, while FIG. 31 and FIG. 34 illustrate two embodiments of the brake pad 918, the present disclosure is not limited to any particular brake pad configuration.

FIG. 35 illustrates an electrosurgical instrument 1000 having electromagnetic gates to regulate the operational stroke. The electrosurgical instrument 1000 may have an end effector 1010 similar to the end effector 110 illustrated in FIG. 3 that is coupled to the distal end of an elongate shaft 1004. An axially moveable member 1006 may extend from the distal end of the elongate shaft 1004 into a handle 1002. A trigger 1007 is coupled to the axially moveable member 1006. In one embodiment, the trigger 1007 comprises a trigger web 1008 that is received by the handle 1002 during a trigger stroke. The electrosurgical instrument 1000 may be electrically coupled to an electrical source 1045. The electrical source 1045 may be connected to the electrosurgical instrument 1000 via a suitable transmission medium such as a cable 1052. In one embodiment, the electrical source 1045 is coupled to a controller 1046.

The electrosurgical instrument 1000 may comprise an electromagnet engaging surface 1014 positioned proximate the trigger 1007 in the handle 1002. In various embodiments, the electromagnet engaging surface 1014 may be ferrous. The electrosurgical instrument 1000 may also comprise a plurality of electromagnetic gates 1012 positioned proximate to the trigger 1007. In one embodiment, the plurality of electromagnetic gates 1012 are coupled to the trigger web 1008 such that they pass proximate the electromagnet engaging surface 1014 during a trigger stroke. The electromagnetic gates 1012 may be selectively magnetized and de-magnetized by the controller 1046 in order to control the trigger actuation during the operational stroke.

FIGS. 36A-C are enlarged side views of the trigger web 1008 and the electromagnet engaging surface 1014 during an operational stroke in accordance with one non-limiting embodiment. As illustrated in FIG. 36A, electromagnetic gates 1012a-c are coupled to the trigger web 1008 and are in electrical communication with the controller 1046 via signal lines. In one embodiment, at the start of an operational stroke, all of the electromagnetic gates 1012a-c are energized such that they create a corresponding magnetic field. The electromagnet engaging surface 1014 is attracted to the magnetic field of first electromagnetic gate 1012a. The trigger 1007 will remain in this position until the first electromagnetic gate 1012a is deactivated. Once the first electromagnetic gate 1012a is deactivated, the user may actuate the trigger 1007 to move the trigger 1007 in the direction indicated by arrow 1016. The electromagnet engaging surface 1014 will then be attracted to the magnetic field of the second electromagnetic gate 1012b (FIG. 36B). The trigger 1007 will remain in this position until the second electromagnetic gate 1012b is deactivated. Once the second electromagnetic gate 1012b is deactivated, the user may actuate the trigger 1007 to move the trigger 1007 in the direction indicated by arrow 1016. The electromagnet engaging surface 1014 will then be attracted to the magnetic field of the third electromagnetic gate 1012c (FIG. 36C). The trigger 1007 will remain in this position until the third electromagnetic gate 1012c is deactivated. Once the third electromagnetic gate 1012c is deactivated, the user may actuate the trigger 1007 to move the trigger 1007 in the direction indicated by arrow 1016 to complete the operational stroke, if the operational stroke has not yet been completed.

While FIGS. 36A-C illustrate three electromagnetic gates 1012a-c, it is to be appreciated that any number of electromagnetic gates may be used. For example, in some embodiments, two electromagnetic gates may be used, while in other embodiments, thirty electromagnetic gates may be used, for example. Additionally, similar to embodiments illustrated in FIG. 33A-B, various sensors 934 may supply information to the controller 1046 which is used to determine which electromagnetic gates to activate or deactivate. Such information may include, for example, tissue temperature information, tissue impedance information, or time delay information. Furthermore, in some embodiments, the electromagnet engaging surface 1014 may be coupled to the trigger 1007 and the electromagnetic gates 1012 may be coupled to the handle 1002. In either event, the advancement of the axially moveable member 1006 can be staggered such that the axially moveable member 1006 can be moved incrementally in the distal direction. In at least one such embodiment, the movement of the axially movable member 1006, and a cutting member associated therewith, can be delayed until a significant amount of energy has been applied to the tissue being treated. In some circumstances, the tissue may not be incised until the tissue has received a minimum amount of energy. In certain circumstances, the rate in which the axially movable member 1006 may be moved distally may be impeded, or slowed, until a certain amount of energy has been applied, and/or a certain temperature or impedance of the tissue has been reached, wherein, thereafter the axially movable member 1006 may be permitted to move distally at a faster rate or at a rate which is unimpeded by the gates. Thus, in certain embodiments, the trigger may be sequentially held at every gate for the same amount of time while, in other embodiments, the trigger may be held at different gates for different amounts of time.

In various embodiments, feedback signals may be provided to the user during the operational stroke of the electrosurgical instrument. FIG. 37 is a cut-away view of an electrosurgical instrument 1100 having a feedback indicator 1102 in accordance with one non-limiting embodiment. For the sake of clarity, various components have been omitted from the electrosurgical instrument 1100. The electrosurgical instrument 1100 may have an end effector (not illustrated) similar to the end effector 110 illustrated in FIG. 3 coupled to the distal end of an elongate shaft 1104. An axially moveable member 1106 may extend from the distal end of the elongate shaft 1104 into the handle 1108. A trigger 1110 is coupled to axially moveable member 1106.

The trigger 1110 may be a ratcheting trigger that has multiple positions along the operational stroke. As illustrated, the trigger 1110 may comprise a hub 1164 that rotates about a pivot 1166 during an operational stroke. The hub may define a plurality of notches or detents 1168 that rotate past a pawl 1160 during an operational stroke. The pawl 1160 may be biased toward the hub by a spring 1162. The pawl 1160 may comprise, for example, a ball bearing to engage the individual detents 1168, for example. The number of detents 1168 may correspond to the number of discrete trigger positions along the operational stroke. The detents 1168 may be evenly spaced around the periphery of the hub 1168 or the distance separating adjacent detents may vary. When the user actuates the trigger, the engagement of the pawl 1160 with the detent 1168 provides tactile feedback to the user. The discrete positions may be implemented using a pawl and ratchet, or any other suitable technique. In one embodiment, the trigger has at five positions (e.g., five detents), for example, although any suitable number of positions may be used.

Still referring to FIG. 37, in a first position 1112, the trigger 1110 is un-actuated and the jaws on the end effector are open and capable of grasping tissue. At a second position 1114, the axially moveable member 1106 is distally advanced to close the jaws of the end effector. At this point in the operational stroke, energy may be applied to the captured tissue. At a third position 1116, the axially moveable member 1106 has started to transect the captured tissue. At a fourth position 1118, the axially moveable member 1106 has continued to travel through the captured tissue and at the fifth position 1120 the tissue has been completely transected. As is to be appreciated, various embodiments the operational stroke may have more or less discrete positions, as determined by the number of detents 1168.

The feedback indicator 1102 is configured to convey operational information to the user. In one embodiment, the feedback indicator 1102 is a series of lights (e.g., light emitting diodes). In one embodiment, the feedback indicator 1102 is positioned proximate the trigger 1110 and provides a vibratory signal to the hand of the user. In one embodiment, the feedback indicator 1102 is a sound-emitting device that provided audio signals to the user. In one embodiment, the feedback indicator 1102 is a combination of multiple forms of feedback, such as a tactile and audio, for example. In one embodiment, the feedback indicator 1102 is located in a position remote from the electrosurgical device 1100, such as on an external power supply, for example. For illustration purposes only, the operation of the feedback indicator 1102 will be described in the context of a series of lights mounted on the handle 1108 of the electrosurgical instrument 1100.

Figure 38A:
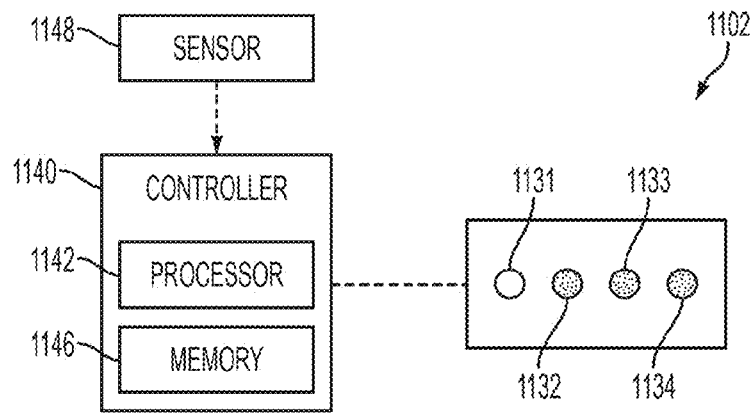

FIGS. 38A-D illustrate the progression of feedback signals provided by the feedback indicator 1102 in accordance with one non-limiting embodiment. The feedback indicator comprises a first indicator 1131, a second indicator 1132, a third indicator 1133, and a fourth indicator 1134. In one embodiment indicators, 1131-1134 are light emitting diodes (LEDs) which may be toggled between a green indication and a red indication during the operational stroke. In some embodiments, the LEDs may be white LEDs that are toggled between an on and an off state during an operational stroke. In other embodiments, other forms of visual indicators may be used, such as an LCD screen, for example. As illustrated in FIG. 33A, the feedback indicator 1102 may be electrically coupled to a controller 1140. The controller 1140 may receive information from a sensor 1148, such as a tissue impedance sensor. The controller 1140 may comprise one or more processors 1142 and one or more computer memories 1146. For convenience, only one processor 1142 and only one memory 1146 are shown in FIG. 38A. The processor 1142 may be implemented as an integrated circuit (IC) having one or multiple cores. The memory 1146 may comprise volatile and/or non-volatile memory units. Volatile memory units may comprise random access memory (RAM), for example. Non-volatile memory units may comprise read only memory (ROM), for example, as well as mechanical non-volatile memory systems, such as, for example, a hard disk drive, an optical disk drive, etc. The RAM and/or ROM memory units may be implemented as discrete memory ICs, for example.

Figure 38B:
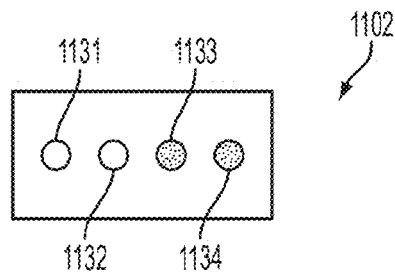
Figure 38C:
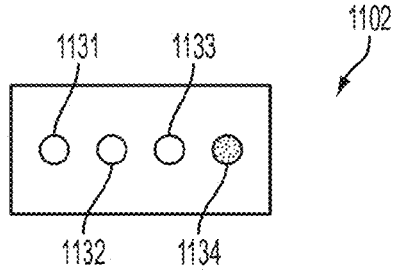
Figure 38D:
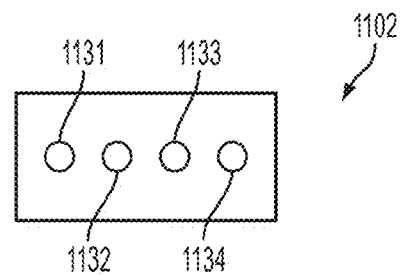

The feedback indicator 1102 may provide information to the user during various stages in the operational stroke. For example, it may provide information to the user which helps the user control the pacing of the operational stroke to increase the likelihood that an adequate tissue seal has been created. In one embodiment, the feedback indicator 1102 provides feedback when the jaws are closed and the axially moveable member is about to transect the captured tissue (e.g., the second position 1114). The movement of the trigger 1110 into the second position can be detected by the controller. Upon detecting the change in the position, the controller may illuminate the first indicator 1131. When the first indicator 1131 is illuminated, the user may apply energy to the captured tissue. For example, the user may depress a button 1150 (FIG. 37) positioned on the trigger 1110. The sensor 1148 may monitor a characteristic or property the captured tissue, such as impedance, and when the tissue has reached a certain impedance level, the second indicator 1132 may be illuminated, as illustrated in FIG. 38B. When the user sees the second indicator 1132 illuminate (or otherwise toggle its state), the user may actuate the trigger 1110 to the next position (e.g., the third position 1116) to begin the cutting stroke. The sensor 1148 may continue monitor the characteristic or property the captured tissue, such as impedance, for example, and when the tissue has reached a certain impedance level, the third indicator 1133 may be illuminated, as illustrated in FIG. 38C. When the user sees the third indicator 1133 illuminate (or otherwise toggle its state), the user may actuate the trigger 1110 to the next position (e.g., the fourth position 1118) to continue its cutting stroke. The sensor 1148 may continue monitor the characteristic or property the captured tissue, such as impedance, for example, and when the tissue has reached a certain impedance level, the fourth indicator 1134 may be illuminated, as illustrated in FIG. 38D. When the user sees the fourth indicator 1134 illuminate (or otherwise toggle its state), the user may actuate the trigger 1110 to the next position (e.g., the fifth position 1120) to complete its cutting stroke.

The embodiments of the devices described herein may be introduced inside a patient using minimally invasive or open surgical techniques. In some instances it may be advantageous to introduce the devices inside the patient using a combination of minimally invasive and open surgical techniques. Minimally invasive techniques may provide more accurate and effective access to the treatment region for diagnostic and treatment procedures. To reach internal treatment regions within the patient, the devices described herein may be inserted through natural openings of the body such as the mouth, anus, and/or vagina, for example. Minimally invasive procedures performed by the introduction of various medical devices into the patient through a natural opening of the patient are known in the art as NOTES™ procedures. Some portions of the devices may be introduced to the tissue treatment region percutaneously or through small—keyhole—incisions.

Endoscopic minimally invasive surgical and diagnostic medical procedures are used to evaluate and treat internal organs by inserting a small tube into the body. The endoscope may have a rigid or a flexible tube. A flexible endoscope may be introduced either through a natural body opening (e.g., mouth, anus, and/or vagina) or via a trocar through a relatively small—keyhole—incision incisions (usually 0.5-1.5 cm). The endoscope can be used to observe surface conditions of internal organs, including abnormal or diseased tissue such as lesions and other surface conditions and capture images for visual inspection and photography. The endoscope may be adapted and configured with working channels for introducing medical instruments to the treatment region for taking biopsies, retrieving foreign objects, and/or performing surgical procedures.

The devices disclosed herein may be designed to be disposed of after a single use, or they may be designed to be used multiple times. In either case, however, the device may be reconditioned for reuse after at least one use. Reconditioning may include a combination of the steps of disassembly of the device, followed by cleaning or replacement of particular pieces, and subsequent reassembly. In particular, the device may be disassembled, and any number of particular pieces or parts of the device may be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of this application.

Preferably, the various embodiments of the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. Other sterilization techniques can be done by any number of ways known to those skilled in the art including beta or gamma radiation, ethylene oxide, and/or steam.

Although the various embodiments of the devices have been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An electrosurgical instrument, comprising:
a handle;
an elongate shaft extending distally from the handle;
an end effector coupled to a distal end of the elongate shaft, comprising:
a first jaw member;
a second jaw member, wherein the first jaw member is moveable relative to the second jaw member between an open and a closed position;
a tissue-cutting element configured to translate with respect to the first jaw member and the second jaw member; and
an electrode;
an axially moveable cutting member configured to move the first jaw member to the closed position, the tissue-cutting element positioned at a distal end of the axially moveable cutting member, wherein the tissue-cutting element is configured to cut tissue captured by the end effector;
a trigger coupled to the axially moveable cutting member, wherein the trigger is moveable through a first range of motion to advance the axially moveable cutting member to move the first jaw member to the closed position, and wherein the trigger is moveable through a second range of motion to advance the axially moveable cutting member to translate the tissue-cutting element to cut the captured tissue; and
a powered linear actuator coupled to the axially moveable cutting member, wherein the axially moveable cutting member is manually advanced without the powered linear actuator to move the first jaw member to the closed position during the first range of motion of the trigger, and wherein the axially moveable cutting member is advanced with the powered linear actuator to translate the tissue-cutting element to cut the captured tissue during the second range of motion of the trigger.

2. The electrosurgical instrument of claim 1, wherein the powered linear actuator comprises a motor and a lead screw.

3. The electrosurgical instrument of claim 2, comprising a nut assembly in threaded engagement with the lead screw.

4. The electrosurgical instrument of claim 1, wherein the powered linear actuator distally drives the axially moveable cutting member in the second range of motion of the trigger.

5. The electrosurgical instrument of claim 4, wherein the first jaw member moves from the open position to the closed position in the first range of motion of the trigger.

6. The electrosurgical instrument of claim 1, further comprising:
a force transducer coupled to the axially moveable cutting member; and
a linear actuator controller in electrical communication with the powered linear actuator and the force transducer.

7. The electrosurgical instrument of claim 6, wherein the linear actuator controller is configured to drive the powered linear actuator at an adjustable speed.

8. The electrosurgical instrument of claim 7, wherein the linear actuator controller is configured to determine the adjustable speed based at least on a signal from the force transducer.

9. The electrosurgical instrument of claim 1, further comprising:
a pressure sensor coupled to the trigger; and
a linear actuator controller in electrical communication with the powered linear actuator and the pressure sensor, wherein the linear actuator controller is configured to drive the powered linear actuator at an adjustable speed, wherein the linear actuator controller is configured to determine the adjustable speed based at least on a signal from the pressure sensor.

10. The electrosurgical instrument of claim 9, further comprising
an electrical input; and
a switch moveable between an unactuated position and an actuated position, wherein the electrical input is electrically coupled to the electrode when the switch is in the actuated position.

11. The electrosurgical instrument of claim 10, further comprising a trigger sensor, wherein the trigger sensor supplies a trigger signal to the linear actuator controller in the second range of motion of the trigger.

12. The electrosurgical instrument of claim 11, wherein the linear actuator controller actuates the powered linear actuator when the switch is in the actuated position and the trigger sensor supplies the trigger signal.

13. An electrosurgical instrument, comprising:
a handle;
an elongate shaft extending distally from the handle, an end effector coupled to a distal end of the elongate shaft, comprising:
a first jaw member;
a second jaw member, wherein the first jaw member is moveable relative to the second jaw member between an open and a closed position;
a tissue-cutting element configured to translate with respect to the first jaw member and the second jaw member; and
an electrode;
an axially moveable cutting member configured to move the first jaw member to the closed position, the tissue-cutting element positioned at a distal end of the axially moveable cutting member, wherein the axially moveable cutting member comprises a distal stop and a proximate stop, and wherein the tissue-cutting element is configured to cut tissue captured by the end effector;
a trigger coupled to the axially moveable cutting member moveable between a first position, a second position, and a third position, wherein the trigger is moveable from the first position to the second position to advance the axially moveable cutting member to move the first jaw member to the closed position, and wherein the trigger is moveable from the second position to the third position to advance the axially moveable cutting member to translate the tissue-cutting element to cut the captured tissue; and
a powered linear actuator coupled to a nut, wherein the nut is coupled to the axially moveable cutting member intermediate the distal stop and the proximate stop, wherein the trigger is configured to manually advance the proximate stop towards the nut without the powered linear actuator as the trigger moves from the first position to the second position, and wherein the trigger is configured to advance the nut away from the proximate stop with the powered linear actuator as the trigger is moved from the second position to the third position.

14. The electrosurgical instrument of claim 13, wherein the proximate stop engages the nut when the trigger is in the second position.

15. The electrosurgical instrument of claim 13, wherein the powered linear actuator comprises a lead screw in threaded engagement with the nut.

16. The electrosurgical instrument of claim 13, wherein the powered linear actuator distally drives the axially moveable cutting member when the trigger moves from the second position to the third position.

17. The electrosurgical instrument of claim 13, further comprising:
an electrical input; and
a switch moveable between an unactuated position and an actuated position, wherein the electrical input is electrically coupled to the electrode when the switch is in the actuated position.

18. The electrosurgical instrument of claim 17, wherein the powered linear actuator distally drives the axially moveable cutting member when the switch is in the actuated position and the trigger is in the third position.

19. An electrosurgical instrument, comprising:
a handle;
an elongate shaft extending distally from the handle;
an end effector coupled to a distal end of the elongate shaft, comprising:
a first jaw member,
a second jaw member, wherein the first jaw member is moveable relative to the second jaw member between an open and a closed position;
a tissue-cutting element configured to translate with respect to the first jaw member and the second jaw member; and
an electrode;
an axially moveable cutting member configured to move the first jaw member to the closed position, the tissue-cutting element positioned at a distal end of the axially moveable cutting member;
a trigger coupled to the axially moveable cutting member, wherein the trigger is moveable between a first position and a second position to advance the axially moveable cutting member to sequentially move the first jaw member to the closed position and cut tissue captured by the end effector;
a motor coupled to the axially moveable cutting member;
a load cell coupled to the axially moveable cutting member; wherein the load cell is configured to output a load signal; and
wherein the motor distally drives the axially moveable cutting member at a variable speed, wherein the variable speed is at least partially based on the load signal, wherein the trigger is configured to advance the axially moveable cutting member without the motor to move the first jaw member to the closed position, and wherein the trigger is configured to advance the axially moveable cutting member with the motor to cut the captured tissue.

* * * * *